United States Patent
Dellamano et al.

(10) Patent No.: US 9,757,575 B2
(45) Date of Patent: Sep. 12, 2017

(54) CHARGING SYSTEM INCLUDING TRANSMIT COIL CURRENT SENSING CIRCUITRY

(71) Applicant: SYNTILLA MEDICAL LLC, Dallas, TX (US)

(72) Inventors: Harry Dellamano, Santa Rosa Valley, CA (US); Paul Griffith, Santa Rosa Valley, CA (US); Francis M. Menezes, Simi Valley, CA (US)

(73) Assignee: Syntilla Medical LLC, Southlake, TX (US)

( * ) Notice: Subject to any disclaimer, the term of this patent is extended or adjusted under 35 U.S.C. 154(b) by 0 days.

(21) Appl. No.: 15/347,740

(22) Filed: Nov. 9, 2016

(65) Prior Publication Data

US 2017/0189696 A1     Jul. 6, 2017

Related U.S. Application Data

(63) Continuation of application No. 14/989,706, filed on Jan. 6, 2016.

(51) Int. Cl.
*A61N 1/378* (2006.01)
*A61N 1/36* (2006.01)
(Continued)

(52) U.S. Cl.
CPC ......... *A61N 1/3787* (2013.01); *A61N 1/0526* (2013.01); *A61N 1/36071* (2013.01);
(Continued)

(58) Field of Classification Search
CPC ............... A61N 1/3787; A61N 1/0526; A61N 1/36071; A61N 1/36075; A61N 1/36125; A61N 1/37229; A61N 1/37247
See application file for complete search history.

(56) References Cited

U.S. PATENT DOCUMENTS 3,727,616 A     4/1973   Lenzkes
4,612,934 A     9/1986   Borkan
(Continued)

FOREIGN PATENT DOCUMENTS

| CA | 2734775 | 2/2015 |
|---|---|---|
| EP | 0007157 | 1/1980 |
| WO | 2009158389 | 12/2009 |

OTHER PUBLICATIONS

PCT: International Search Report and Written Opinion of PCT/US2014/51235; Feb. 19, 2015; 24 pages.
(Continued)

*Primary Examiner* — Catherine Voorhees
(74) *Attorney, Agent, or Firm* — Munck Wilson Mandala, LLP

(57) ABSTRACT

A system for transferring power to, and communicating with, at least one body-implantable active device includes an external power transfer system associated with an external device disposed outside of a body, operable to transfer power through a dermis layer to each body-implantable active device, and communicate data to and from each body-implantable active device, and also includes a power receiving system associated with each body-implantable active device, operable to receive power transferred from the external power transfer system, and communicate data to and from the external power transfer system. The body-implantable active device may include an implantable neurostimulation system.

20 Claims, 23 Drawing Sheets

(51) Int. Cl.
*A61N 1/372* (2006.01)
*A61N 1/05* (2006.01)

(52) U.S. Cl.
CPC ..... *A61N 1/36075* (2013.01); *A61N 1/36125* (2013.01); *A61N 1/37229* (2013.01); *A61N 1/37247* (2013.01)

(56) References Cited

U.S. PATENT DOCUMENTS

| | | |
|---|---|---|
| 4,793,353 A | 12/1988 | Borkan |
| 4,819,647 A | 4/1989 | Byers |
| 5,000,194 A | 3/1991 | Van Den Honert et al. |
| 5,037,497 A | 8/1991 | Stypulkowski |
| 5,215,086 A | 6/1993 | Terry, Jr. et al. |
| 5,279,292 A | 1/1994 | Baumann et al. |
| 5,545,219 A | 8/1996 | Kuzma |
| 5,615,100 A | 3/1997 | Radecker et al. |
| 5,733,313 A | 3/1998 | Barreras, Sr. |
| 5,876,425 A | 3/1999 | Gord et al. |
| 5,905,646 A | 5/1999 | Crewson et al. |
| 6,016,449 A | 1/2000 | Fischell et al. |
| 6,088,619 A | 7/2000 | Hein et al. |
| 6,178,353 B1 | 1/2001 | Griffith et al. |
| 6,236,892 B1 | 5/2001 | Feler |
| 6,246,911 B1 | 6/2001 | Seligman |
| 6,456,883 B1 | 9/2002 | Torgerson et al. |
| 6,516,227 B1 | 2/2003 | Meadows |
| 6,529,774 B1 | 3/2003 | Greene |
| 6,597,954 B1 | 7/2003 | Fischell et al. |
| 6,606,521 B2 | 8/2003 | Paspa et al. |
| 6,618,623 B1 | 9/2003 | Pless et al. |
| 6,895,283 B2 | 5/2005 | Erickson et al. |
| 6,920,359 B2 | 7/2005 | Meadows et al. |
| 7,127,298 B1 | 10/2006 | He et al. |
| 7,319,906 B2 | 1/2008 | Kuzma et al. |
| 7,437,197 B2 | 10/2008 | Harris et al. |
| 7,499,755 B2 | 3/2009 | Cross, Jr. |
| 7,599,743 B2 * | 10/2009 | Hassler, Jr. .......... A61N 1/3787 607/40 |
| 7,676,273 B2 | 3/2010 | Goetz et al. |
| 7,706,892 B2 | 4/2010 | Colvin et al. |
| 7,729,781 B2 | 6/2010 | Swoyer et al. |
| 7,769,461 B2 | 8/2010 | Whitehurst et al. |
| 7,894,905 B2 | 2/2011 | Pless et al. |
| 8,027,735 B1 | 9/2011 | Tziviskos et al. |
| 8,030,798 B2 | 10/2011 | Seligman |
| 8,140,152 B2 | 3/2012 | John et al. |
| 8,165,678 B2 | 4/2012 | Forsberg |
| 8,412,334 B2 | 4/2013 | Whitehurst et al. |
| 8,504,163 B1 | 8/2013 | Meadows |
| 8,509,876 B2 | 8/2013 | Karmarkar |
| 8,538,545 B2 | 9/2013 | Meskens |
| 8,543,212 B2 | 9/2013 | Merfeld et al. |
| 8,634,909 B2 | 1/2014 | Zimmerling et al. |
| 8,639,344 B2 | 1/2014 | Greenberg et al. |
| 8,639,391 B1 | 1/2014 | Alberth, Jr. et al. |
| 8,649,880 B1 | 2/2014 | Parker |
| 8,718,779 B2 | 5/2014 | Whitehurst et al. |
| 8,774,924 B2 | 7/2014 | Weiner |
| 8,958,880 B2 | 2/2015 | De Giorgio |
| 8,972,015 B2 | 3/2015 | Stack et al. |
| 9,020,589 B2 | 4/2015 | Torgerson |
| 9,095,699 B2 | 8/2015 | Rosenberg et al. |
| 9,101,732 B2 | 8/2015 | Dadd et al. |
| 9,498,635 B2 | 11/2016 | Dellamano et al. |
| 2002/0032471 A1 | 3/2002 | Loftin et al. |
| 2002/0116042 A1 | 8/2002 | Boling |
| 2005/0027192 A1 | 2/2005 | Govari et al. |
| 2005/0030774 A1 | 2/2005 | Vazquez Carazo |
| 2005/0075696 A1 | 4/2005 | Forsberg et al. |
| 2005/0102006 A1 | 5/2005 | Whitehurst et al. |
| 2005/0182470 A1 | 8/2005 | Cross |
| 2005/0209667 A1 | 9/2005 | Erickson et al. |
| 2005/0288741 A1* | 12/2005 | Hassler, Jr. .......... A61N 1/3787 607/61 |
| 2006/0241717 A1 | 10/2006 | Whitehurst et al. |
| 2006/0247754 A1 | 11/2006 | Greenberg et al. |
| 2006/0293723 A1 | 12/2006 | Whitehurst et al. |
| 2007/0073357 A1 | 3/2007 | Rooney et al. |
| 2007/0112404 A1 | 5/2007 | Mann et al. |
| 2007/0203545 A1 | 8/2007 | Stone et al. |
| 2008/0039916 A1 | 2/2008 | Colliou |
| 2008/0183253 A1 | 7/2008 | Bly |
| 2008/0269716 A1 | 10/2008 | Bonde |
| 2008/0300657 A1 | 12/2008 | Stultz |
| 2009/0018619 A1 | 1/2009 | Skelton et al. |
| 2009/0058635 A1 | 3/2009 | LaLonde et al. |
| 2009/0209945 A1 | 8/2009 | Lobl et al. |
| 2009/0210028 A1 | 8/2009 | Rigaux |
| 2009/0312769 A1 | 12/2009 | Dadd |
| 2010/0110741 A1 | 5/2010 | Lin et al. |
| 2010/0161004 A1 | 6/2010 | Najafi |
| 2010/0274313 A1 | 10/2010 | Boling et al. |
| 2010/0331922 A1 | 12/2010 | DiGiore et al. |
| 2011/0009925 A1 | 1/2011 | Leigh et al. |
| 2011/0046699 A1 | 2/2011 | Mazanec |
| 2011/0093047 A1 | 4/2011 | Davis et al. |
| 2011/0112603 A1 | 5/2011 | DeGiorgio et al. |
| 2011/0172736 A1 | 7/2011 | Gefen et al. |
| 2011/0190849 A1 | 8/2011 | Faltys et al. |
| 2012/0078327 A1 | 3/2012 | Sloan et al. |
| 2012/0112556 A1 | 5/2012 | Forsell |
| 2012/0215218 A1 | 8/2012 | Lipani |
| 2012/0274270 A1 | 11/2012 | Dinsmoor |
| 2012/0277823 A1 | 11/2012 | Gerber et al. |
| 2013/0057364 A1 | 3/2013 | Kesler et al. |
| 2013/0085542 A1 | 4/2013 | Mashiach |
| 2013/0085561 A1 | 4/2013 | Mashiach |
| 2013/0131754 A1 | 5/2013 | Sarvazyan |
| 2013/0197613 A1 | 8/2013 | Kelly |
| 2013/0198531 A1 | 8/2013 | Hansen |
| 2013/0238067 A1 | 9/2013 | Baudino |
| 2013/0282086 A1 | 10/2013 | McDonald et al. |
| 2013/0289662 A1 | 10/2013 | Olson et al. |
| 2013/0333918 A1 | 12/2013 | Lotfi |
| 2014/0012349 A1 | 1/2014 | Zimmerling et al. |
| 2014/0070808 A1 | 3/2014 | Reykowski et al. |
| 2014/0142669 A1 | 5/2014 | Cook et al. |
| 2014/0148883 A1 | 5/2014 | Stack et al. |
| 2014/0222125 A1 | 8/2014 | Glenn et al. |
| 2014/0292327 A1 | 10/2014 | Griswold et al. |
| 2014/0303685 A1 | 10/2014 | Rosenberg et al. |
| 2014/0343626 A1 | 11/2014 | Thenuwara et al. |
| 2015/0025613 A1 | 1/2015 | Nyberg, II et al. |
| 2015/0087892 A1 | 3/2015 | Tourrel et al. |
| 2015/0157862 A1 | 6/2015 | Greenberg et al. |
| 2015/0280444 A1 | 10/2015 | Smith et al. |
| 2015/0303806 A1 | 10/2015 | Madsen et al. |
| 2016/0008602 A1 | 1/2016 | Perryman et al. |
| 2016/0036244 A1 | 2/2016 | Griffith |
| 2016/0114174 A1 | 4/2016 | Colvin et al. |
| 2016/0242685 A1 | 8/2016 | DeHennis et al. |

OTHER PUBLICATIONS

Weiner RL and Reed KL. Peripheral neurostimulation for control of intractable occipital neuralgia. Neuromodulation: Journal of the International Neuromodulation Society. Jan. 1, 1999; 2: 217-21.

Goadsby PJ and Spencer T. Current practice and future directions in the prevention and acute management of migraine. The Lancet Neurology. Jan. 1, 2010; 9: 285-98.

Dodick DW. Occipital nerve stimulation for chronic cluster headache. Advanced Studies in Medicine. Jan. 1, 2003; 3: S569-S71.

Saper JR, Dodick DW, Silberstein SD, McCARVILLE S, Sun M and Goadsby PJ. Occipital nerve stimulation for the treatment of intractable chronic migraine headache: ONSTIM feasibility study. Cephalalgia: an international journal of headache. Jan. 1, 2011; 31:271-85.

Silberstein S, Dodick DW, Reed KL, et al. Safety and efficacy of peripheral nerve stimulation of the occiptial nerves for the management of chronic migraine. Cephalalgia: an international journal of headache. Jan. 1, 2012.

(56) References Cited

OTHER PUBLICATIONS

Slavin KV, Colpan ME, Munawar N, Wess C and Nersesyan H. Trigeminal and occipital peripheral nerve stimulation for craniofacial pain: a single-institution experience and review of the literature. Neurosurgical focus. Jan. 1, 2006; 21: E5.

Schwedt TJ, Dodick DW, Hentz J, Trentman TL and Zimmerman RS. Occipital nerve stimulation for chronic headache—long-term safety and efficacy. Cephalagia: an international journal of headache. Jan. 1, 2007; 27: 153-7.

Reed KL, Black SB, Banta CJ, 2nd and Will KR. Combined occipital and supraorbital neurostimulation for the treatment of chronic migraine headaches: initial experience. Cephalalgia: an international journal of headache. Jan. 1, 2010; 30: 260-71.

Reed KL, Will KR, Chapman J and Richter E. Combined occipital and supraorbital neurostimulation for chronic migraine headaches [abst]. 15th Congress of the International Headache Society. Berlin, Germany: Cephalalgia, Jan. 1, 2011, p. 98-9.

Lipton RB, Goadsby PJ, Cady RK, et al. Prism study: occipital nerve stimulation for treatment-refractory migraine (p abs). Cephalalgia: an international journal of headache. Jan. 1, 2009; 29: 30.

Reed KL. Peripheral neuromodulation and headaches: history, clinical approach, and considerations on underlying mechanisms. Current pain and headache reports. Jan. 1, 2012; 17: 25-35.

Mueller OM, Gaul C, Katsarava Z, Diener HC, Sure U and Gasser T. Occipital nerve stimulation for the treatment of chronic cluster headache—lessons learned from 18 months experience. Central European neurosurgery. Jan. 1, 2011; 72: 84-9.

Medtronic, Inc. Peripheral Nerve Stimulation: Percutaneous Lead Implantation Guide for Treatment of Chronic Pain; Jan. 1, 1999.

Redl, Richard. Fundamental Considerations for Very High Frequency Power Conversion. Electronic Feasibility Investigations. Jan. 1, 2008.

Sreelakshmi V, Menon R, Sheela G. An RF-FC Converter with Wide Dynamic Range Input Matching for Power Recovery Applications. International Journal of Advanced Research in Electrical, Electronics and Instrumentation Engineering. Dec. 1, 2014.

Rooij M. eGaN FET based Wireless Energy Transfer Topology Performance Comparisons, Jan. 1, 2015.

* cited by examiner

CHARGING SYSTEM INCLUDING TRANSMIT COIL CURRENT SENSING CIRCUITRY

CROSS-REFERENCE TO RELATED APPLICATIONS

This application is a continuation of U.S. patent application Ser. No. 14/989,706, filed Jan. 6, 2016, entitled CHARGING SYSTEM INCORPORATING INDEPENDENT CHARGING AND COMMUNICATION WITH MULTIPLE IMPLANTED DEVICES, the specification of which is incorporated by reference herein in its entirety.

TECHNICAL FIELD

The present disclosure relates to systems and methods for wirelessly charging/powering and communicating with body-implantable active medical devices, and particularly for a body-implantable neurostimulation device.

BACKGROUND

Neurostimulation systems that include implantable neurostimulation leads are used to treat chronic pain. Such systems may include an implantable pulse generator (IPG) from which one or more neurostimulating leads may extend to a length sufficient to provide therapeutic neurostimulation over desired regions of the body, such as regions of the head and back. The IPG may include a rechargeable battery, an antenna coil, and circuitry to control the neurostimulating leads. The IPG may also be configured for functionally connecting with an external radiofrequency unit that may be operable to perform various functions including recharging the rechargeable battery, diagnostically evaluating the IPG, and programming the IPG.

Improved techniques are desired for wirelessly charging/powering and communicating with such implantable neurostimulation systems and other body-implantable active devices, especially when such systems are implanted fully beneath the skin.

SUMMARY

In one aspect, a system is provided for transferring power to, and communicating with, at least one body-implantable active device. In some embodiments the system includes an external power transfer system associated with an external device disposed outside of a body, operable to transfer power through a dermis layer to each body-implantable active device, and communicate data to and from each body-implantable active device, and also includes a power receiving system associated with each body-implantable active device, operable to receive power transferred from the external power transfer system, and communicate data to and from the external power transfer system.

In another aspect, a system is provided for charging and communicating with at least two body-implantable active devices, each with a battery. In some embodiments, the system includes an external charging system disposed outside of the body for transferring charging energy to the body and facilitating transmission of data to, and reception of data from, the body-implanted active devices, and also includes a charge receiving system associated with each of the body-implanted active devices for receiving energy transferred from the external charging system and facilitating transmission of data to, and reception of data from, the external charging system.

In various implementations, the body-implanted active device may include an implantable head-located, unibody peripheral nerve stimulation system that is configured for implantation of substantially all electronics, including an on-site battery, at or near the implanted electrodes on the skull. The system may include an implantable pulse generator (IPG) from which two neurostimulating leads may extend to a length sufficient to provide therapeutic neurostimulation unilaterally over the frontal, parietal and occipital regions of the hemicranium. The system may be operable to provide medically acceptable therapeutic neurostimulation to multiple regions of the head, including the frontal, parietal and occipital regions of the hemicranium, substantially simultaneously.

Each of the leads may include an extended lead body, a plurality of surface metal electrodes disposed along the lead body, which electrodes may be divided into two or more electrode arrays, and a plurality of internal electrically conducting metal wires running along at least a portion of the length of the lead body and individually connecting an internal circuit of the IPG to individual surface metal electrodes. The extended lead body may comprise a medical grade plastic. The IPG may include a rechargeable battery, an antenna coil, and an application specific integrated circuit (ASIC). The IPG may be configured for functionally connecting with an external radiofrequency control device. The external radiofrequency control device may be operable to perform various functions including recharging the rechargeable battery, diagnostically evaluating the IPG, and programming the IPG.

The foregoing is a summary and thus contains, by necessity, simplifications, generalizations and omissions of detail. The details of various implementations are set forth in the accompanying drawings and the description below. Consequently, those skilled in the art will appreciate that the foregoing summary is illustrative only and is not intended to be in any way limiting of the invention. It is only the claims, including all equivalents, in this or any non-provisional application claiming priority to this application, that are intended to define the scope of the invention(s) supported by this application.

BRIEF DESCRIPTION OF THE DRAWINGS

For a more complete understanding of this disclosure, reference is now made to the following description, taken in conjunction with the accompanying drawings.

In the drawings, like reference numbers are used herein to designate like elements throughout. The drawings are not necessarily drawn to scale, and in some instances the drawings have been exaggerated and/or simplified in places for illustrative purposes only.

DETAILED DESCRIPTION

Embodiments will now be described more fully hereinafter with reference to the accompanying drawings, in which various embodiments of the invention are shown. This invention may, however, be embodied in many different forms and should not be construed as limited to the embodiments set forth herein; rather, these embodiments are provided so that this disclosure will be thorough and complete. One of ordinary skill in the art will appreciate the many possible applications and variations based on the following examples of possible embodiments.

Figure 1:
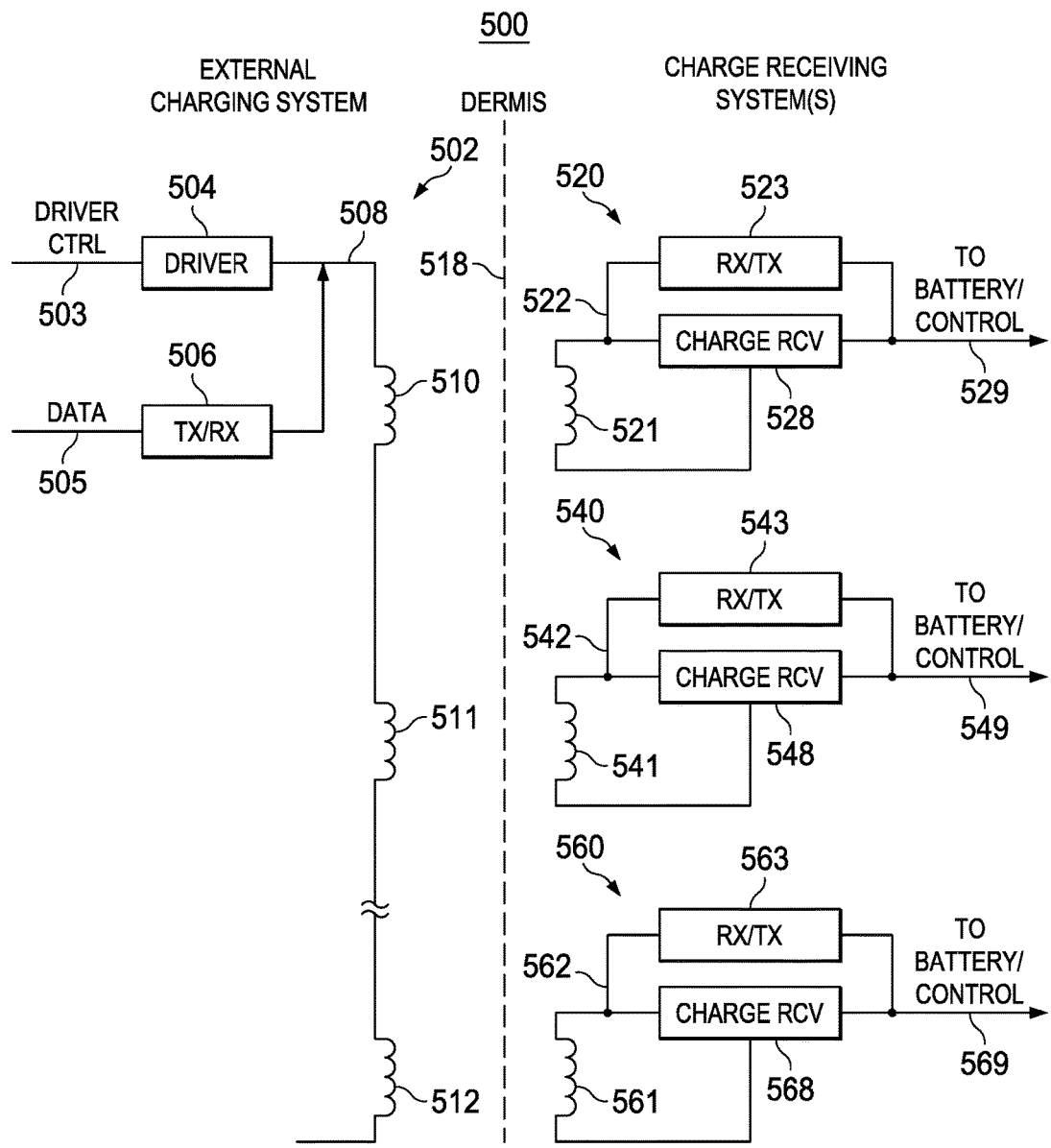
FIG. 1 is a block diagram of a system that provides for independent charging and communication with multiple implanted devices, in accordance with some embodiments of the invention.

FIG. 1 depicts a conceptual diagram of a system 500 that provides for independent charging/powering and communication with multiple body-implanted devices requiring external power to power the body-implanted devices directly or to charge an internal battery (or other charge storage device) associated with the body-implanted devices, or a hybrid thereof. For the purposes of this disclosure, charge provided to the body-implanted devices will be referred to as "charging," but it should be understood that this could mean charging of a battery or other charge storage device, or delivering charge to power a circuit block or element associated with the body-implanted devices, or a combination of both. Three charge receiving systems 520, 540, 560 are shown, each disposed within a corresponding body-implanted device (not shown). An external charging system 502 disposed outside a dermis layer 518 includes series-connected transmit coils, of which three are shown, being series-connected transmit coils 510, 511, 512, each of which corresponds to a respective one of receive coils 521, 541, 561 of respective ones of a plurality of charge receiving systems, of which three are shown, being charge receiving systems 520, 540, 560. Preferably each receive coil 521, 541, 561 is tuned to the resonant frequency of the respective transmit coil 510, 511, 512 within the external charging system 502. While three transmit coils 510, 511, 512 are shown, one for each charge receiving system 520, 540, 560, other embodiments may utilize one transmit coil, two transmit coils, or another number of transmit coils, depending upon the number of body-implanted devices.

The external charging system 502 includes a driver 504, responsive to a DRIVER CTRL signal on node 503, for driving the series-connected coils 510, 511, 512 with an AC signal. A TX/RX telemetry block 506 includes a transmitter for transmitting a forward telemetry data signal within the AC signal driven across the transmit coils (i.e., on node 508), and a receiver to detect and receive a back telemetry data signal within the AC signal. The forward/back telemetry data signals, both as represented by the DATA signal on node 505, are coupled from/to telemetry circuitry within remaining portions of the external charging system (not shown). As used herein, data communication from an external charging system to a body-implanted device is referred to as forward telemetry, and data communication from a body-implanted device to an external charging system is referred to as back telemetry.

Within the first body-implanted device, the charge receiving system 520 includes a receive coil 521 that is tuned to the resonant frequency of the associated transmit coil 510 within the external charging system 502, so that receive coil 521 may receive energy transferred from the transmit coil 510 when in close proximity thereto. The receive coil 521 is coupled to a charge receiving block 528 that includes circuitry for receiving energy in a first mode of operation, and for de-tuning the receive coil 521 in a second mode of operation to inhibit transfer of energy. The receive coil 521 is also coupled (via node 522) to an RX/TX telemetry block 523 that includes a receiver for receiving a forward telemetry data signal from the receive coil 521, and a transmitter for transmitting a back telemetry data signal to the receive coil 521. The received energy is coupled to battery charging circuitry, and the forward/back telemetry data signals are coupled to/from data circuitry within the first body-implanted device, both as represented by node 529. As can be appreciated, the receive coil 521 serves as a "shared antenna" for both the charging system and the telemetry system.

Similarly, the charge receiving system 540 includes a receive coil 541 that is tuned to the resonant frequency of the associated transmit coil 511, so that receive coil 541 may receive energy transferred from the transmit coil 511 when in close proximity thereto. The receive coil 541 is coupled to a charge receiving block 548 that includes circuitry for receiving energy in the first mode of operation, and for de-tuning the receive coil 541 in the second mode of operation to inhibit transfer of energy. The receive coil 541 is also coupled (via node 542) to an RX/TX telemetry block 543 that includes a receiver for receiving a forward telemetry data signal from the receive coil 541, and a transmitter for transmitting a back telemetry data signal to the receive coil 541. The received energy is coupled to battery charging circuitry (or a charge delivering circuit when no battery is present), and the forward/back telemetry data signals are coupled to/from data circuitry within the second body-implanted device, both as represented by node 549.

Likewise, the charge receiving system 560 includes a receive coil 561 that is tuned to the resonant frequency of the associated transmit coil 512, so that receive coil 561 may receive energy transferred from the transmit coil 512 when in close proximity thereto. The receive coil 561 is coupled to a charge receiving block 568 that includes circuitry for receiving energy in the first mode of operation, and for de-tuning the receive coil 561 in the second mode of operation to inhibit transfer of energy. The receive coil 561 is also coupled (via node 562) to an RX/TX telemetry block 563 that includes a receiver for receiving a forward telemetry data signal from the receive coil 561, and a transmitter for transmitting a back telemetry data signal to the receive coil 561. The received energy is coupled to battery charging circuitry, and the forward/back telemetry data signals are coupled to/from data circuitry within the third body-implanted device, both as represented by node 569.

Even though a single driver circuit 504 is utilized to drive all three series-connected transmit coils 510, 511, 512, the system 500 provides for independent charging (or charge delivery) of multiple body-implanted devices. When such charging of one of the body-implanted devices is complete (or delivery of charge), the corresponding de-tuning circuitry within the respective charge receiving circuit 528, 548, 568 may be activated to de-tune its respective receive coil 521, 541, 561 and thereby inhibit further transfer of energy to the respective charge receiving circuit 528, 548, 568. Each body-implanted device may de-tune its receive coil when charging is complete, independently of the other body-implanted devices, to limit needless power loss and undesirable heating within a fully-charged body-implanted device (or a non-battery device that requires no delivery of charge), without affecting energy transfer to the remaining charge receiving systems 520, 540, 560.

Moreover, even though a single driver circuit 504 is utilized to drive all three series-connected transmit coils 510, 511, 512, the system 500 also provides for independent communication with multiple body-implanted devices. Since the forward telemetry (transmit) data signal within the AC signal is driven across all three series-connected transmit coils 510, 511, 512, each of the charge receiving systems 520, 540, 560 can independently receive such a transmitted data signal. As for receiving data independently from each charge receiving system, the external charging system 502 can coordinate the operation of each charge receiving system 520, 540, 560 so that only one such charge receiving system at a time attempts to communicate back telemetry data to the external charging system 502. Such coordination may be achieved by forward telemetry commands instructing a selected charge receiving system to communicate back telemetry data to the external charging system 502, so that the non-selected charge receiving systems will forego attempted back telemetry during such times. Embodiments described below provide detailed examples of forward and back telemetry circuitry and operation.

Figure 2:
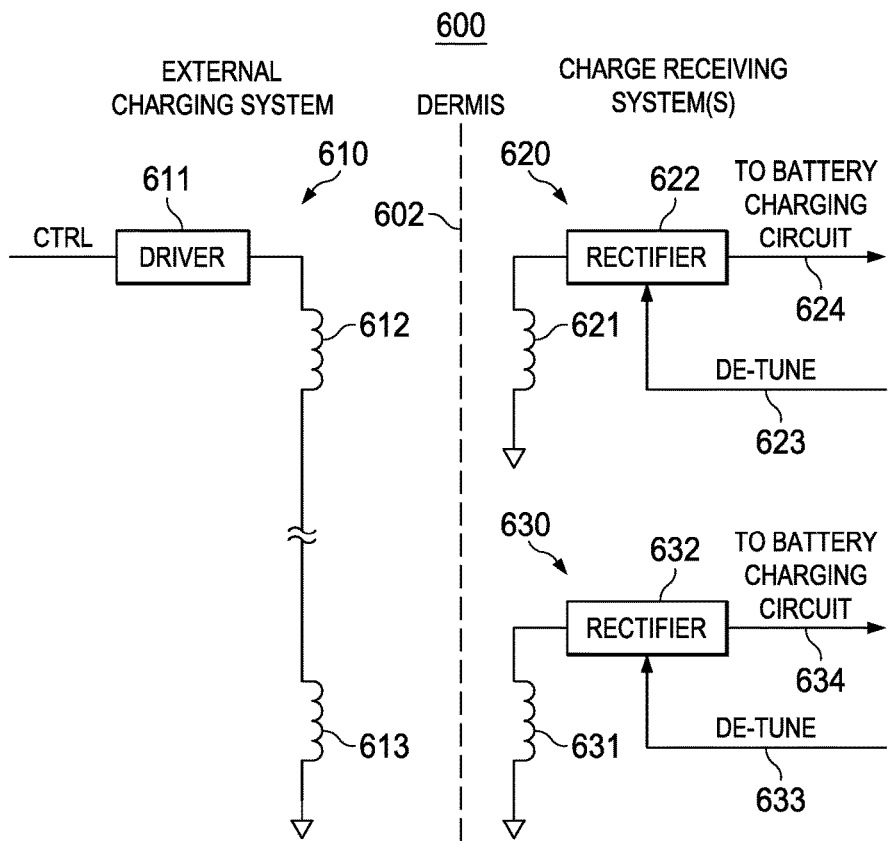
FIG. 2 is a block diagram of a system depicting the de-tuning of a receive coil within an implanted device to selectively turn off charging, in accordance with some embodiments of the invention.

FIG. 2 is a block diagram of a system 600 that provides for the de-tuning of a receive coil within a given body-implanted device to selectively turn off charging (charge delivery) of the given device without affecting battery charging (charge delivery) in one or more other such body-implanted devices. Two charge receiving systems 620, 630 are shown, each disposed within a corresponding body-implanted device. An external charging (charge delivery) system 610 disposed outside a dermis layer 602 includes series-connected transmit coils 612, 613, each of which corresponds to a respective one of receive coils 621, 631 of respective charge receiving systems 620, 630. In this embodiment, two such transmit coils 612, 613 are shown, one for each charge receiving system 620, 630, but other embodiments may utilize one transmit coil or another number of transmit coils, depending upon the number of body-implanted devices.

The external charging system 610 includes a driver 611, responsive to a CTRL signal, for driving the series-connected transmit coils 612, 613 with an AC signal. Within the first body-implanted device, the charge receiving system 620 includes a receive coil 621 that is preferably tuned to the resonant frequency of the associated transmit coil 612 within the external charging system 610, so that receive coil 621 may receive energy transferred from the transmit coil 612 when in close proximity thereto. The receive coil 621 is coupled to a rectifier block 622 for receiving energy in a first mode of operation and generating a rectified voltage on node 624, and for de-tuning the receive coil 621 in a second mode of operation, responsive to a DE-TUNE signal on node 623, to inhibit transfer of energy. The rectified voltage on node 624 is coupled to battery charging (charge delivery) circuitry within the first body-implanted device (not shown).

Within the second body-implanted device, the charge receiving system 630 includes a receive coil 631 that is preferably tuned to the resonant frequency of the associated transmit coil 613 within the external charging system 610, so that receive coil 631 may receive energy transferred from the transmit coil 613 when in close proximity thereto. The receive coil 631 is coupled to a rectifier block 632 for receiving energy in the first mode of operation and generating a rectified voltage on node 634, and for de-tuning the receive coil 631 in the second mode of operation, responsive to a DE-TUNE signal on node 633, to inhibit transfer of energy. The rectified voltage on node 634 is coupled to battery charging (charge delivery) circuitry within the second body-implanted device (not shown).

Even though a single driver circuit 611 is utilized to drive both series-connected transmit coils 612, 613, the system 600 provides for de-tuning of a receive coil within a given body-implanted device to selectively turn off charging of the given device without affecting charging of one or more other such body-implanted devices. As such, independent charging (charge delivery) of multiple body-implanted devices is provided. When such charging (charge delivery) of one of the body-implanted devices is complete, the corresponding DE-TUNE signal may be activated within the respective charge receiving system 620, 630 to de-tune its respective receive coil 621, 631 and thereby inhibit transfer of energy to the respective charge receiving system 620, 630. Each body-implanted device may de-tune its receive coil when charging (charge delivery) is complete, independently of the other body-implanted devices, to limit needless power loss and undesirable heating within a fully-charged body-implanted device, without affecting energy transfer to the remaining charge receiving systems 620, 630. Such completion of charging (charge delivery) may be determined within the charge receiving system of the respective body-implanted device, with or without any communication to the external charging system.

Figure 3:
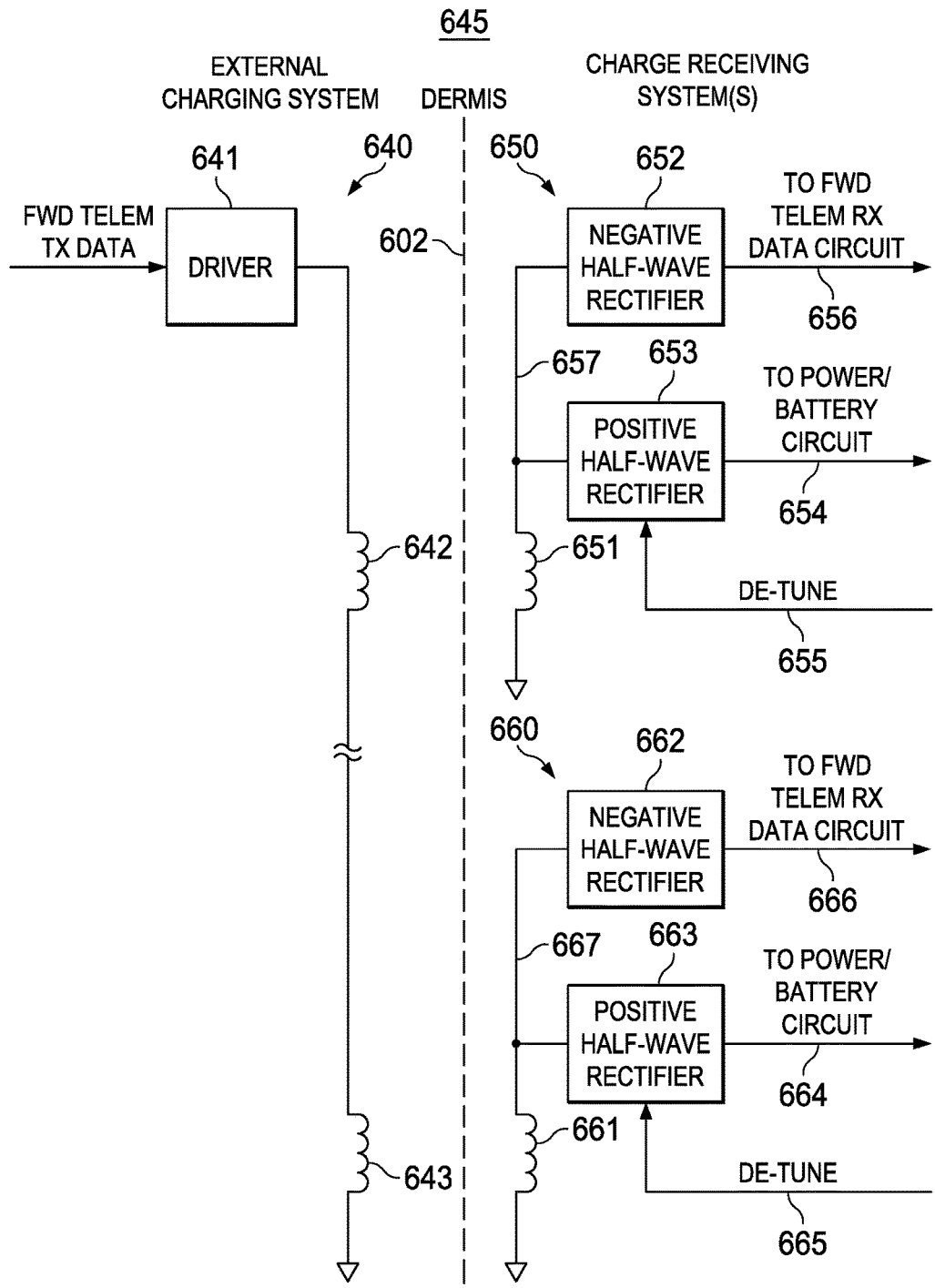
FIG. 3 is a block diagram of a system which provides for data communication (forward telemetry) and power transmission to an implanted device using opposite polarity half-wave rectified signals received by the implanted device, in accordance with some embodiments of the invention.

FIG. 3 is a block diagram of a system 645 which provides for power transmission and data communication to a body-implanted device using opposite-polarity half-wave rectified signals received by the implanted device. Two charge receiving systems 650, 660 are shown, each disposed within a corresponding body-implanted device. An external charging system 640 disposed outside a dermis layer 602 includes series-connected transmit coils 642, 643, each of which corresponds to a respective one of receive coils 651, 661 of respective charge receiving systems 650, 660. Preferably each receive coil 651, 661 is tuned to the resonant frequency of the respective transmit coil 642, 643 within the external charging system 640. In this embodiment, two such transmit coils 642, 643 are shown, one for each charge receiving system 650, 660, but other embodiments may utilize one transmit coil or another number of transmit coils.

The external charging system 640 includes a driver 641 that is responsive to a forward telemetry transmit data signal FWD TELEM TX DATA. When the FWD TELEM TX DATA signal has a first logic state (e.g., logic high), the driver 641 drives the series-connected transmit coils 642, 643 with an AC signal, and when the FWD TELEM TX DATA signal has a second logic state (e.g., logic low), the driver 641 is disabled. In some embodiments, the driver 641 together with the series-connected transmit coils 642, 643 may be configured as a resonant amplifier. When such a resonant amplifier is disabled, the AC signal is allowed to decay and eventually cease.

Such operation may be viewed as providing a 100% amplitude-modulated AC signal driven across the series-connected transmit coils 642, 643, controlled by a bit-serial forward telemetry data signal FWD TELEM TX DATA. Significant charge transfer to one or both charge receiving systems 650, 660 is still readily provided for battery charging (or charge delivery) by limiting the duration of time that the forward telemetry transmit data signal FWD TELEM TX DATA is allowed to "disable" the coil driver 641. Consequently, such a signal also functions as an enable/disable signal for the driver 641 if maintained in the second logic state.

Within a first body-implanted device, the charge receiving system 650 includes a receive coil 651 for receiving energy transferred from the associated transmit coil 642 when in close proximity thereto. The receive coil 651 is coupled to a positive half-wave rectifier block 653 for receiving energy and generating a rectified voltage on node 654, and responsive to a DE-TUNE signal on node 655, for de-tuning the receive coil 651 to inhibit transfer of energy from the associated transmit coil 642. The rectified voltage on node 654 is coupled to power and battery charging (charge delivery) circuitry within the first body-implanted device (not shown), which circuitry also directly or indirectly controls the DE-TUNE signal on node 655 when charging is complete or charge transfer not desired. The receive coil 651 is also coupled via node 657 to a negative half-wave rectifier block 652 for receiving forward telemetry data and generating on node 656 a respective forward telemetry receive data signal, which is conveyed to forward telemetry receive data FWD TELEM RX DATA circuitry within the first body-implanted device (not shown).

Within a second body-implanted device, the charge receiving system 660 includes a receive coil 661 for receiving energy transferred from the associated transmit coil 643 when in close proximity thereto. The receive coil 661 is coupled to a positive half-wave rectifier block 663 for receiving energy and generating a rectified voltage on node 664, and responsive to a DE-TUNE signal on node 665, for de-tuning the receive coil 661 to inhibit transfer of energy from the associated transmit coil 643. The rectified voltage on node 664 is coupled to power and battery charging circuitry within the second body-implanted device (not shown), which circuitry also directly or indirectly controls the DE-TUNE signal on node 665 when charging is complete or charge transfer not desired. The receive coil 661 is also coupled via node 667 to a negative half-wave rectifier block 662 for receiving forward telemetry data and generating on node 666 a respective forward telemetry receive data signal, which is conveyed to forward telemetry receive data FWD TELEM RX DATA circuitry within the first body-implanted device (not shown).

As may be appreciated, each body-implanted device can receive forward telemetry data independently, irrespective of the charging state (i.e., de-tuned state) of that body-implanted device or the other body-implanted device. For example, the charge receiving system 650 may still receive forward telemetry information by the negative half-wave rectifier 652 irrespective of whether the positive half-wave rectifier 653 is de-tuned or not. Such de-tuning greatly lowers the resonant Q of the combination of transmit coil 642 and receive coil 651 for positive voltage excursions on node 657, and consequently serves to inhibit significant energy transfer to receive coil 651, but does not negatively impact the ability for the negative half-wave rectifier 652 to respond to negative transitions on node 657 and generate the output voltage accordingly on node 656. Similarly, the charge receiving system 650 may still receive forward telemetry information irrespective of whether the positive half-wave rectifier 663 within the other charge receiving system 660 is de-tuned or not.

Figure 4B:
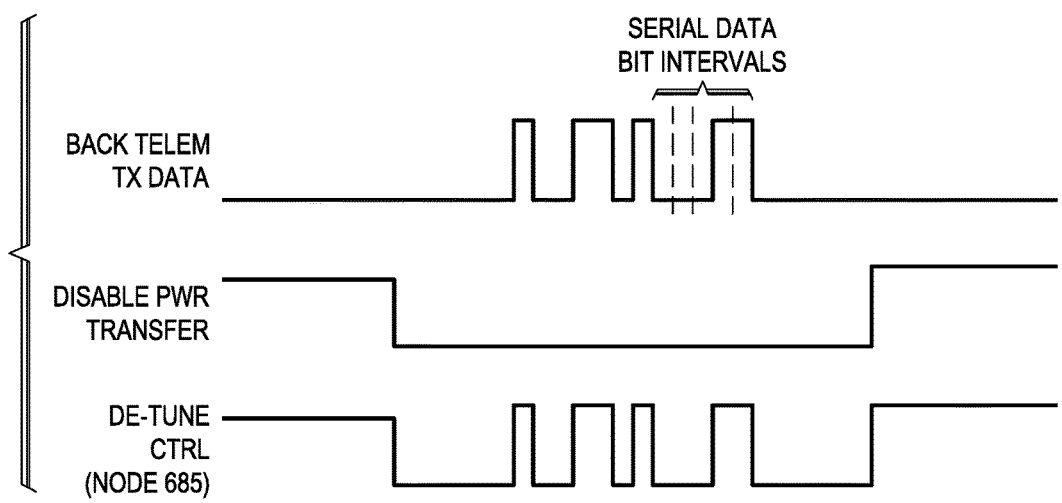
FIG. 4B illustrates voltage waveforms of selected signals depicted in the embodiment shown in FIG. 4A.
Figure 4A:
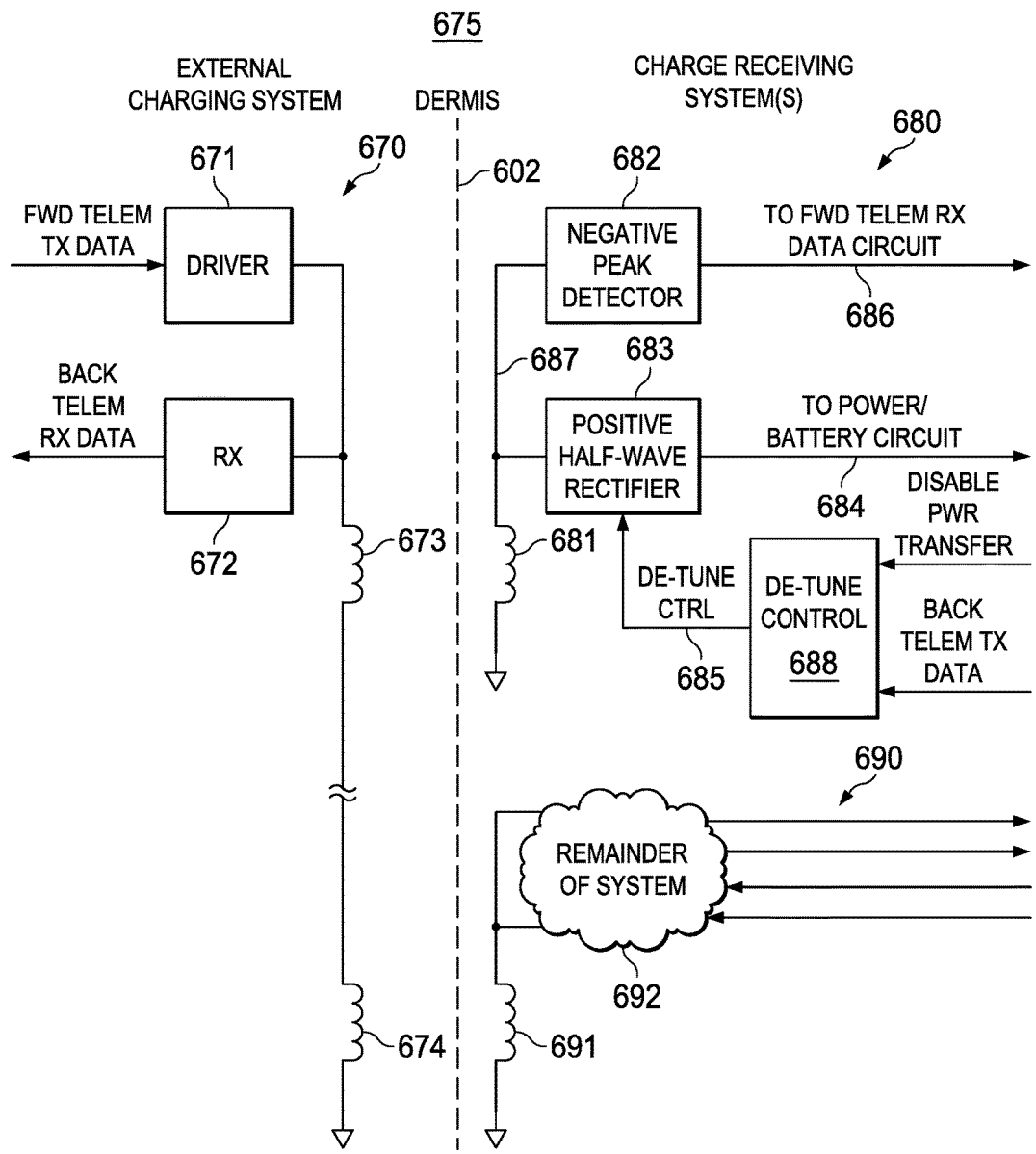
FIG. 4A is a block diagram of a system which provides for bi-directional communication with an implanted device, and particularly illustrates passive communication from an implanted device (back telemetry) when the receive coil is de-tuned, in accordance with some embodiments of the invention.

FIG. 4A is a block diagram of a system 675 which provides for bi-directional communication with a body-implanted device, and particularly illustrates passive communication from an implanted device to the external charging system (i.e., back telemetry) when the receive coil within the implanted device is de-tuned.

Two charge receiving systems 680, 690 are shown, each disposed within a corresponding body-implanted device. An external charging system 670 disposed outside a dermis layer 602 includes series-connected transmit coils 673, 674, each of which corresponds to a respective one of receive coils 681, 691 of respective charge receiving systems 680, 690. As before, preferably each receive coil 681, 691 is tuned to the resonant frequency of the respective transmit coil 673, 674 within the external charging system 670. In this embodiment, two such transmit coils 673, 674 are shown, one for each charge receiving system 680, 690, but other embodiments may utilize one transmit coil or another number of transmit coils, noting that the transmit coils are for delivery of charge to the body-implanted devices. Such charge delivery may be utilized to charge a battery, capacitor, or supercapacitor within the body-implanted device, and/or to power the body-implanted device, particularly if such body-implanted device does not include a battery.

The external charging (charge delivery) system 670 includes a driver 671 that is responsive to a forward telemetry transmit data signal FWD TELEM TX DATA. As described in the embodiment shown in FIG. 3, when the FWD TELEM TX DATA signal is driven to a first logic state (e.g., logic high), the driver 671 drives the series-connected transmit coils 673, 674 with an AC signal, and when the FWD TELEM TX DATA signal is driven to a second logic state (e.g., logic low), the driver 671 is disabled. In some embodiments, the driver 671 together with the series-connected transmit coils 673, 674 may be configured as a resonant amplifier. When such a resonant amplifier is disabled, the AC signal decays and eventually ceases. Such operation may be viewed as providing a 100% amplitude modulation of the AC signal driven onto the series-connected transmit coils 673, 674, which modulation is controlled by a bit-serial forward telemetry data signal that also functions as an enable/disable signal for the driver 671 (if held to the appropriate one of its two logic states). The external charging system 670 also includes a receiver circuit 672 that is responsive to the AC signal on the series-coupled transmit coils 673, 674, and which generates accordingly a back telemetry receive data signal BACK TELEM RX DATA.

Within a first body-implanted device, the charge receiving system 680 includes a receive coil 681 for receiving energy transferred from the associated transmit coil 673 when in close proximity thereto. The receive coil 681 is coupled to a positive half-wave rectifier block 683 for receiving energy and generating a rectified voltage on node 684, and responsive to a DE-TUNE signal on node 685, for de-tuning the receive coil 681 to inhibit transfer of energy from the associated transmit coil 673. The rectified voltage on node 684 is coupled to power and battery charging circuitry within the first body-implanted device (not shown). The receive coil 681 is also coupled via node 687 to a negative peak detector block 682 for receiving forward telemetry data and generating on node 686 a respective forward telemetry receive data signal, which is conveyed to forward telemetry receive data FWD TELEM RX DATA circuitry within the first body-implanted device (not shown).

The charge receiving system 680 also includes a de-tune control block 688 for generating the DE-TUNE control signal on node 685 responsive to a disable power transfer signal DISABLE PWR TRANSFER, and further responsive to a bit-serial back telemetry transmit data signal BACK TELEM TX DATA. In operation, the DISABLE PWR TRANSFER signal may be asserted when charging (or charge transfer) is complete or not desired, which asserts the DE-TUNE control signal to de-tune the receive coil 681 through the positive half-wave rectifier 683. In addition, during normal charging the DE-TUNE control signal may be asserted for each bit-position of the bit-serial BACK TELEM TX DATA signal corresponding to one of its two data states. Since de-tuning the positive half-wave rectifier 683 in concert with the receive coil 681 inhibits energy transfer from the transmit coil 673 to the receive coil 681, the loading of transmit coil 673 is decreased. This decreased loading results in a higher peak current through the series-connected transmit coils 673, 674. In the external charging system 670, the receiver circuit 672 senses the change in peak current through the series-coupled transmit coils 673, 674 as each serial data bit of the BACK TELEM TX DATA signal either tunes or de-tunes the receive coil 681, and generates accordingly a back telemetry receive data signal BACK TELEM RX DATA.

If the DE-TUNE control signal is already asserted (e.g., because the DISABLE PWR TRANSFER signal is asserted to indicate charging/charge transfer is complete or not desired) when the charge receiving system 680 desires to transmit back telemetry data, the DISABLE PWR TRANSFER signal may be briefly de-asserted to allow the BACK TELEM TX DATA signal to control the DE-TUNE control signal, as is shown in FIG. 4B. Thus, the charge receiving system 680 may still transmit back telemetry information irrespective of whether it is generally in a de-tuned state.

Within a second body-implanted device, the charge receiving system 690 includes a receive coil 691 for receiving energy transferred from the associated transmit coil 674 when in close proximity thereto. The remainder 692 of the charge receiving system 690 is identical to the charge receiving system 680, and need not be separately described.

Figure 5A:
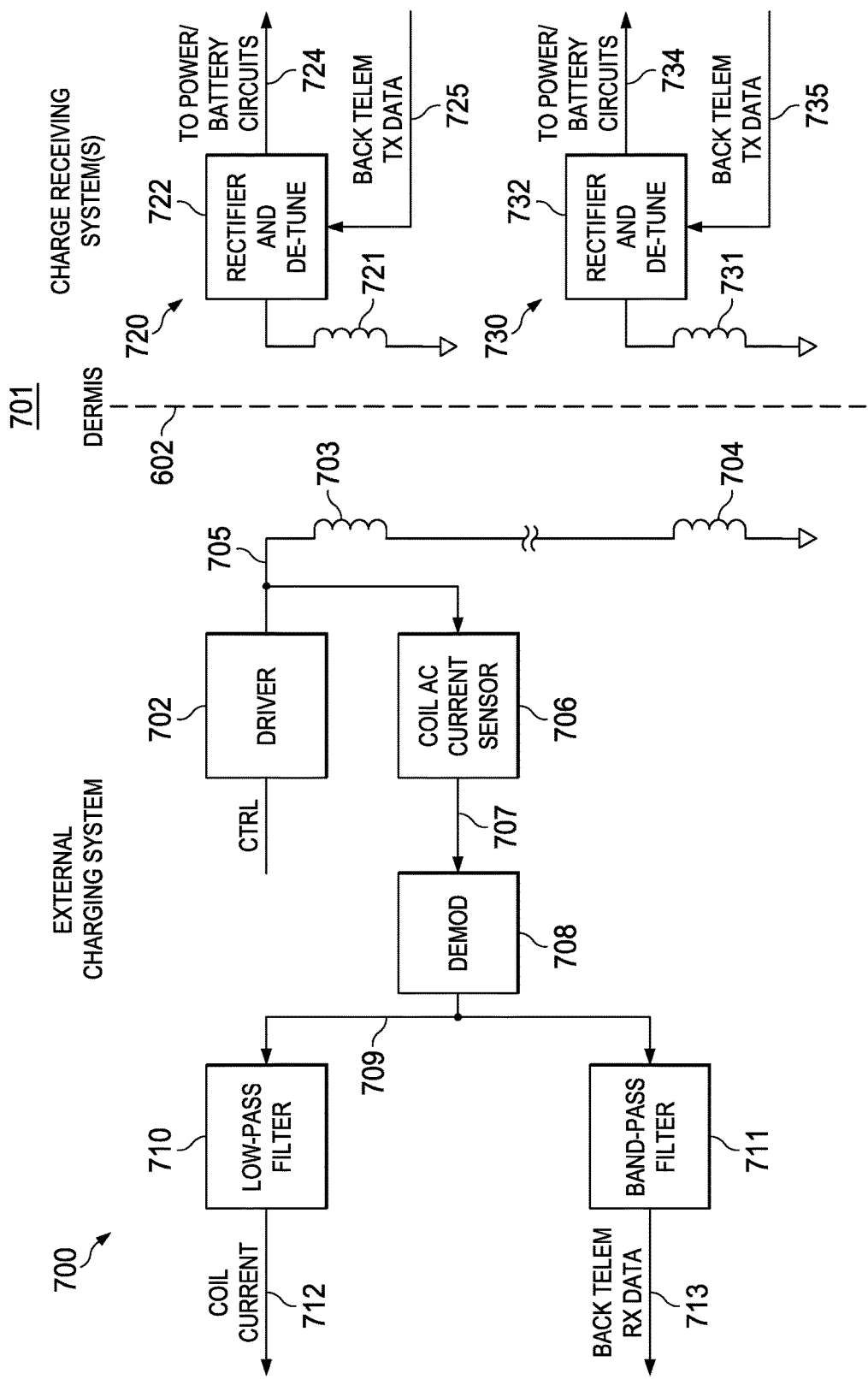
FIG. 5A is a block diagram of a system which includes transmit coil current sensing circuitry to determine back telemetry data received from an implanted device, and to determine de-tuning of an implanted device coil, in accordance with some embodiments of the invention.

FIG. 5A is a block diagram of a system 701 which includes transmit coil ("charging coil") current sensing circuitry, and particularly illustrates sensing such transmit coil current to determine back telemetry data received from an implanted device, and to determine de-tuning of an implanted device receive coil. Two charge receiving systems 720, 730 are shown, each disposed within a corresponding body-implanted active device. An external charging system 700 disposed outside a dermis layer 602 includes series-connected transmit coils 703, 704, each of which corresponds to a respective one of receive coils 721, 731 of respective charge receiving systems 720, 730. Although two such transmit coils 703, 704 are shown, one for each charge receiving system 720, 730, other embodiments may utilize one transmit coil or another number of transmit coils, depending upon the number of body-implanted devices.

The external charging system 700 includes a driver 702, responsive to a CTRL signal, for driving the series-connected transmit coils 703, 704 with an AC signal. Within the first body-implanted device, the charge receiving system 720 includes a receive coil 721 that is preferably tuned to the resonant frequency of the associated transmit coil 703 within the external charging system 700, so that receive coil 721 may receive energy transferred from the transmit coil 703 when in close proximity thereto. The receive coil 721 is coupled to a rectifier/de-tune block 722 for receiving energy at times and generating a rectified output voltage on node 724, and for de-tuning the receive coil 721 at other times, responsive to a respective BACK TELEM TX DATA signal on node 725, to inhibit transfer of energy from the transmit coil 703. The rectified voltage on node 724 is coupled to power/battery charging circuitry within the first body-implanted device (not shown). In this embodiment the BACK TELEM TX DATA signal functions as both a bit-serial data signal and a "disable charge transfer" signal, much like the DE-TUNE signal in the previous embodiment. In order to de-tune the receive coil 721 and disable charging, the BACK TELEM TX DATA signal is driven and held in one of its two logic levels (e.g., a logic high level), while to actually communicate back telemetry data to the external charging system 700, the BACK TELEM TX DATA signal is driven between both its logic levels according to the bit serial data. Any of several encoding formats may be used, but NRZ ("non-return-to-zero") encoding is assumed here.

Within the second body-implanted device, the charge receiving system 730 includes a receive coil 731 that is preferably tuned to the resonant frequency of the associated transmit coil 704 within the external charging system 700, so that receive coil 731 may receive energy transferred from the transmit coil 704 when in close proximity thereto. The receive coil 731 is coupled to a rectifier/de-tune block 732 for receiving energy at times and generating a rectified output voltage on node 734, and for de-tuning the receive coil 731 at other times, responsive to a respective BACK TELEM TX DATA signal on node 735, to inhibit transfer of energy from the transmit coil 704. The rectified voltage on node 734 is coupled to power/battery charging circuitry within the second body-implanted device (not shown).

The external charging system 700 includes circuitry to generate a COIL CURRENT signal corresponding to the magnitude of the transmit coil current, and to generate a BACK TELEM RX DATA signal corresponding to the back telemetry data received from one of the charge receiving systems 720, 730. The back telemetry data is communicated passively by a given one of the charge receiving systems 720, 730 by modulating the amount of energy transferred from the external transmit coils and received by a given charge receiving system. Such modulation occurs by changing whether the corresponding receive coil is tuned or de-tuned. De-tuning the receive coil may occur when battery charging (charge transfer) is complete or not desired, in which case the transferred energy will decrease and remain at the decreased value, but may also occur in response to a bit-serial BACK TELEM TX DATA signal, in which case the variations or changes in transferred energy will have a frequency component matching the bit rate of the BACK TELEM TX DATA signal. The back telemetry data is received by the external charging system by sensing the variation in transmit coil current that corresponds to changes in the amount of energy transferred to the given charge receiving system.

In this embodiment, the circuitry to accomplish this includes a transmit coil AC current sensor 706 having an input coupled to the output node 705 of driver 702, which generates on its output node 707 an AC voltage signal corresponding to the instantaneous current through the series-connected transmit coils 703, 704. This AC voltage signal on node 707 is coupled to a demodulator 708 which generates on its output node 709 a demodulated signal corresponding to the peak value of the AC voltage signal on node 707, which corresponds to the peak value of the instantaneous current through the transmit coils 703, 704. This demodulated signal on node 709 is filtered by low-pass filter 710 to generate the COIL CURRENT signal on node 712. The COIL CURRENT signal is a generally DC-like signal that is reflective of the low-frequency changes in the peak transmit coil current, such as would occur when charging is complete (i.e., charge transfer no longer desired) and its corresponding receive coil is de-tuned and remains de-tuned for some time.

Figure 5B:
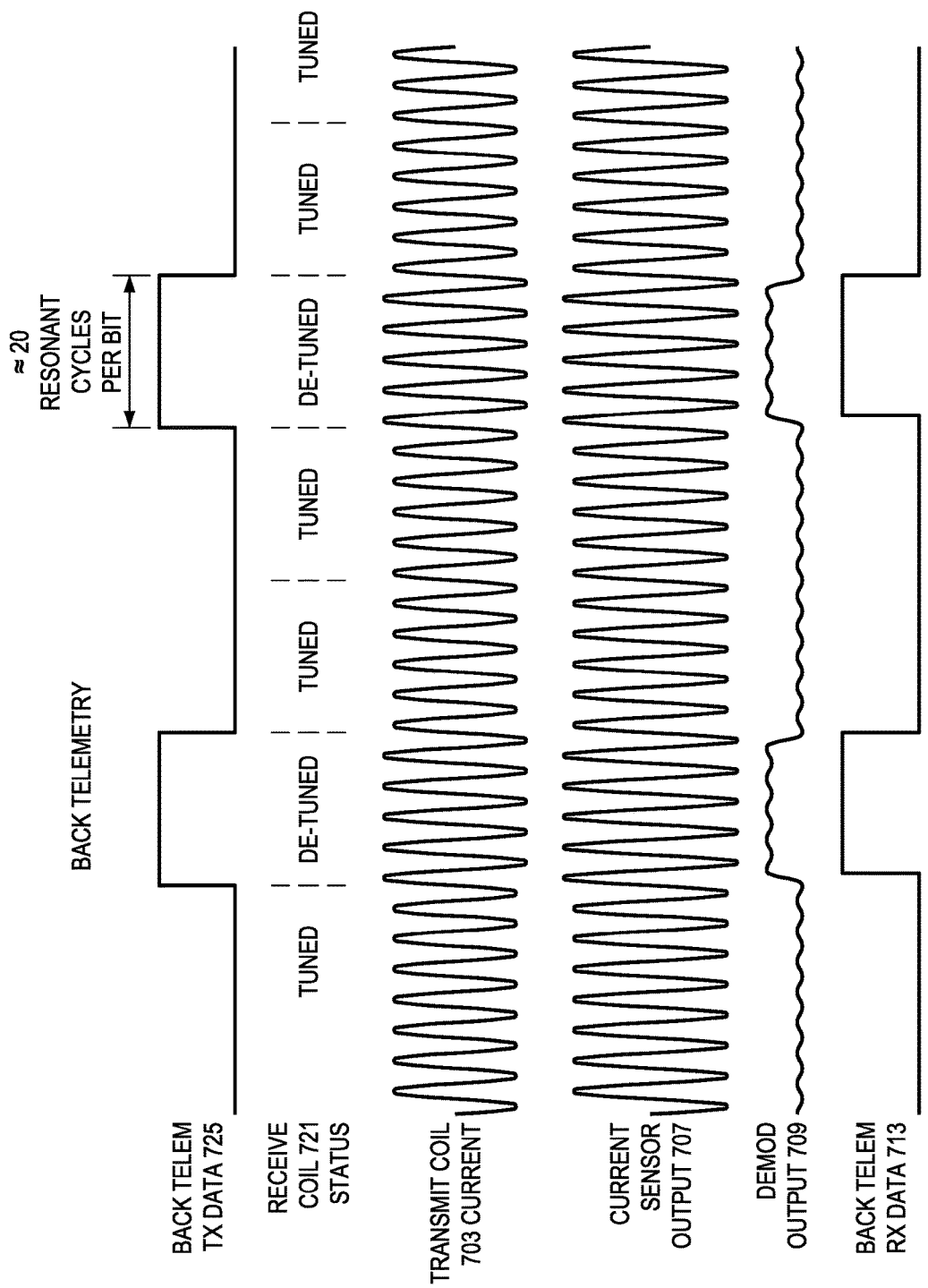
FIG. 5B illustrates voltage waveforms of selected signals depicted in the embodiment shown in FIG. 5A.

The demodulated signal on node 709 is also coupled to a band-pass filter 711 to generate the BACK TELEM RX DATA signal on node 713. This BACK TELEM RX DATA signal is reflective of higher-frequency changes in the peak transmit coil current, such as would occur when back telemetry data is being communicated and the corresponding receive coil is de-tuned and tuned responsive to the bit-serial BACK TELEM TX DATA signal. Illustrative waveforms of these signals are shown in FIG. 5B. In some embodiments the data rate for the back telemetry need not be identical to the data rate for the forward telemetry. For example, the back telemetry data rate, relative to the resonant frequency of the transmit coils in the external charging system, may be result in each bit interval (i.e., bit position) corresponding to as few as 20 cycles of the resonant amplifier, as noted in FIG. 5B. Additional examples and other embodiments of such current sensing and receive data circuits are described below.

As noted above, FIG. 5B shows waveforms of selected signals illustrating back telemetry operation in the embodiment shown in FIG. 5A. In particular, the bit-serial BACK TELEM TX DATA signal (node 725) is shown representing several bits of information to be communicated from the charge receiving system 720 to the external charging system 700, along with the corresponding tuned or de-tuned status of the receive coil 721. The peak current through the transmit coil 703 is higher corresponding to the de-tuned state of the receive coil 721. A voltage signal is generated at the output 707 of the current sensor 706, which voltage signal corresponds to the instantaneous current through the transmit coil 703. This output signal 707 is demodulated to produce the demodulated output signal on node 709, which is then filtered by band-pass filter 711 to produce the BACK TELEM RX DATA signal on node 713.

Figure 6:
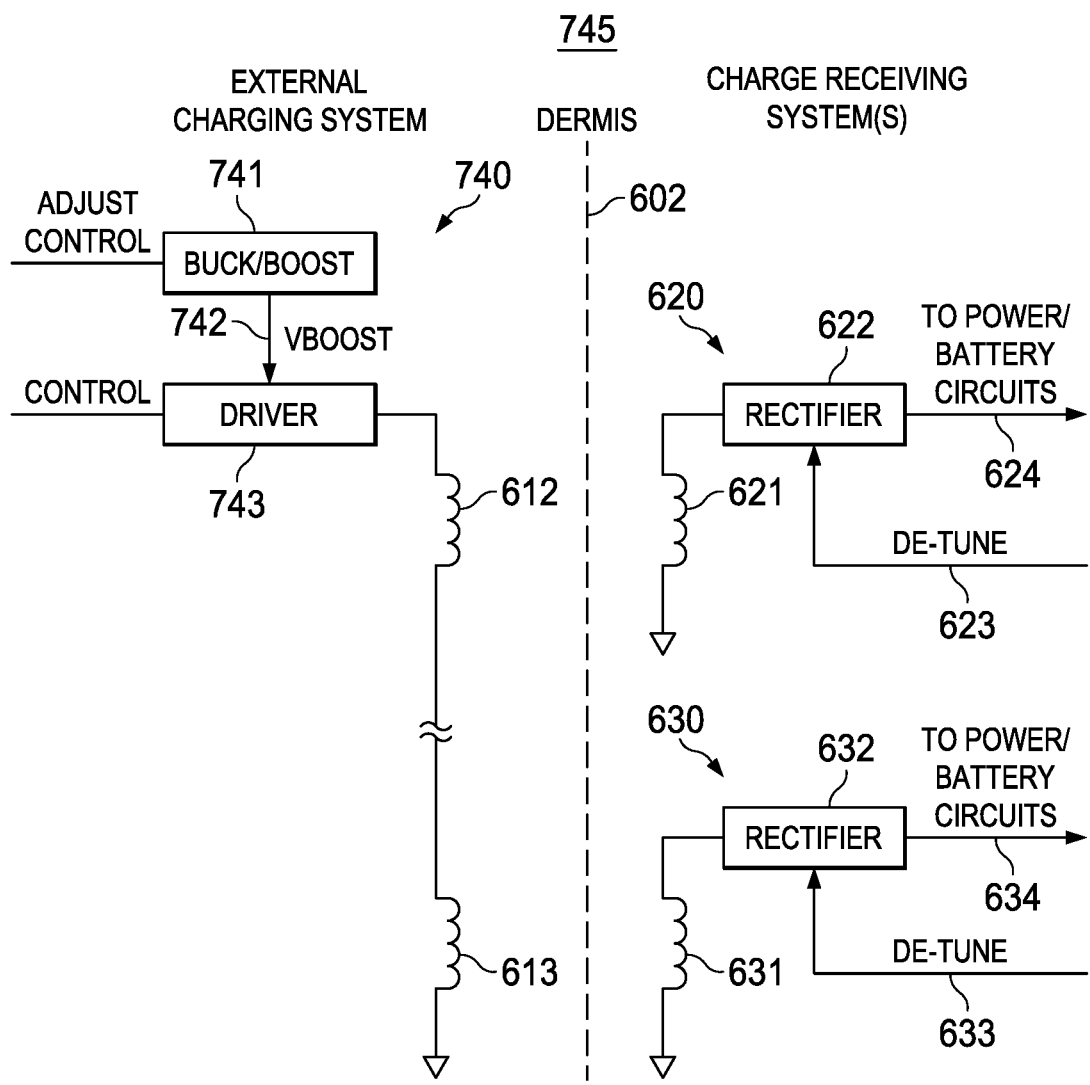
FIG. 6 is a block diagram of a system which provides for adjustable transmitted power to improve power efficiency within an implanted device, in accordance with some embodiments of the invention.

FIG. 6 is a block diagram of an exemplary charging system 745 which provides for adjustable transmitted power to improve power efficiency within an implanted device. Two charge receiving systems 620, 630 are shown, each disposed within a corresponding body-implanted device, which are identical to those described in FIG. 2, and need not be described here. An external charging system 740 disposed outside a dermis layer 602 includes series-connected transmit coils 612, 613, each of which corresponds to a respective one of receive coils 621, 631 of respective charge receiving systems 620, 630. Two such transmit coils 612, 613 are shown, one for each charge receiving system 620, 630, but other embodiments may utilize one transmit coil or another number of transmit coils, depending upon the number of body-implanted devices.

The external charging system 740 includes a resonant driver 743 for driving the series-connected transmit coils 612, 613 with an AC signal, and a buck/boost circuit 741 that provides on node 742 a variable DC voltage for use by the driver 743 as an upper power supply node. By varying this VBOOST voltage on node 742, the amount of energy stored each resonant cycle in the transmit coils and ultimately transferred to the corresponding receive coil may be varied, for example, to achieve better charging (charge delivery) efficiency and coupling within the implanted device. The resonant driver 743 is responsive to a CTRL signal, such as described above regarding other embodiments, which may function as both a data signal and as an enable signal.

The VBOOST voltage on node 742 may be varied as battery charging progresses (or the charge delivery requirements change) within each body-implanted device. For example, during an early phase of charging when the battery voltage is relatively low, it may be desirable to limit the rectified voltage on node 624 so that any voltage drop across the charging circuit within the body-implanted device is kept to a minimum necessary to achieve proper voltage regulation, or to provide a particular constant magnitude of battery charging current, to efficiently charge the battery. Later, as battery charging progresses and the battery is charged to a higher voltage, the rectified voltage on node 624 may be increased to maintain a desired voltage drop across such charging circuitry or to maintain the desired battery charging current. When one of the body-implanted devices is fully charged and its receive coil (e.g., 621) is de-tuned, the other body-implanted device may still be charging and its receive coil (e.g., 631) still tuned for resonant energy transfer from the external charge system. The VBOOST voltage may then be adjusted to optimize the amount of energy transfer into the remaining body-implanted device.

The buck/boost circuit 741 is shown as being responsive to an ADJUST CTRL signal, which may be controlled within the external charging system in response to detecting a decrease in energy transfer to one or more body-implanted devices (e.g., using the COIL CURRENT signal described above), by receiving back telemetry information from one or both body-implanted devices regarding internal voltage levels, internal current levels, and/or internal temperatures, or by one or more temperature sensors within the external charging system (e.g., a sensor placed near each transmit coil), or by any other useful means, such as information from one or both body-implanted devices conveyed using a Bluetooth connection to the external charging system. This adjustability of the VBOOST voltage provides for adjustable control of the energy coupled to one or both of the charge receiving systems within the body-implanted devices, even though both series-connected transmit coils 612, 613 are driven by a single driver circuit 743. However, it should be noted that changing of the amount of energy that can be coupled to any of the body-implanted devices will change the amount of energy transfer to all the body-implanted devices. Thus, although not disclosed herein, the body-implanted devices must operate such that charge delivered is governed by the one of the body-implanted devices that requires the most charge. Each of the body-implanted devices, for example, will send information back to the external charging (charge delivery) system in the form of a request to indicate an increased need for charge, and the amount of charge transfer will be increased until the body-implanted device requiring the most charge has that request satisfied.

Figure 7A:
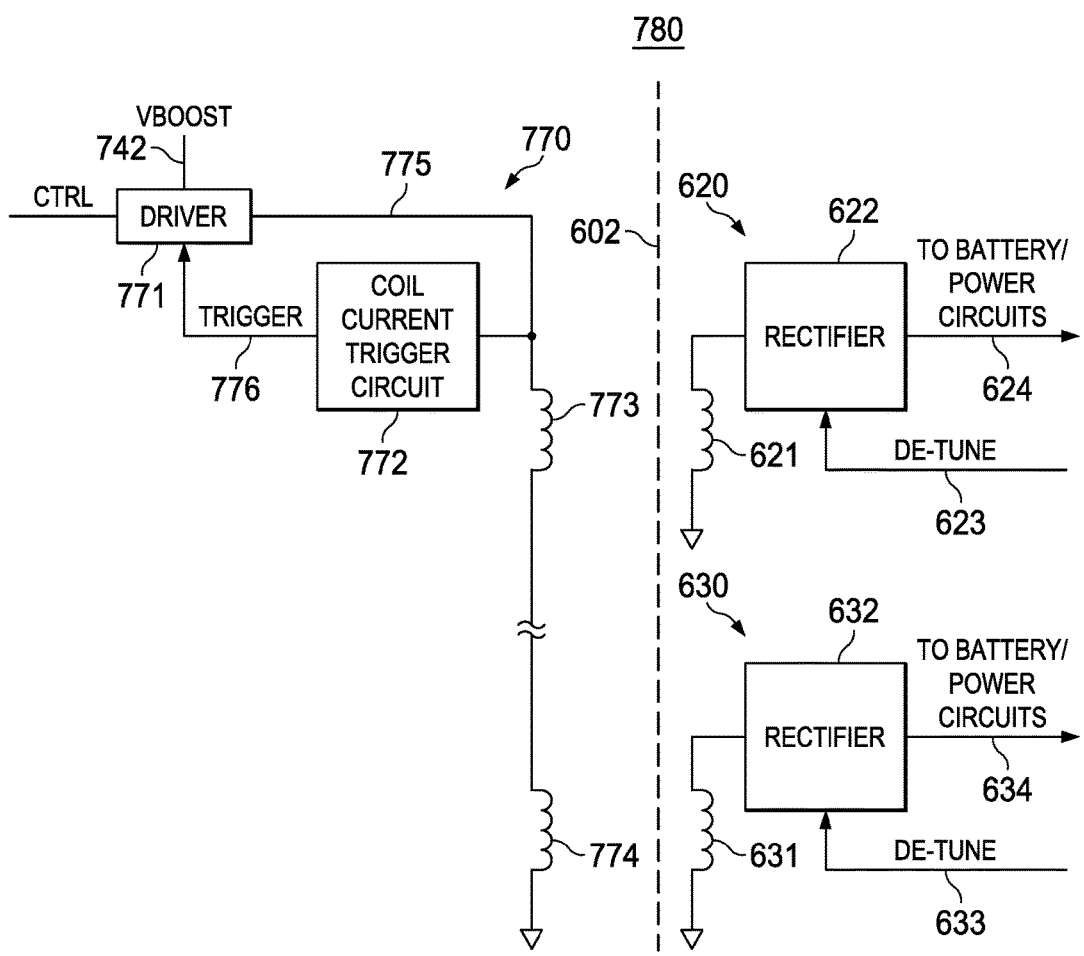
FIG. 7A is a block diagram of a system which includes feedback excitation control of a resonant coil driver amplifier, in accordance with some embodiments of the invention.

FIG. 7A is a block diagram of an exemplary system 780 which includes feedback excitation control of a resonant coil driver amplifier. Two charge receiving systems 620, 630 are shown, each disposed within a corresponding body-implanted device, which are identical to those described in FIG. 2, and need not be described here. An external charging (charge delivery) system 770 disposed outside a dermis layer 602 includes series-connected transmit coils 773, 774, each of which corresponds to a respective one of receive coils 621, 631 of respective charge receiving systems 620, 630. While two such charging (charge delivery) coils 773, 774 are shown, one for each charge receiving system 620, 630, other embodiments may utilize one transmit coil or another number of transmit coils, depending upon the number of body-implanted devices.

Figure 7B:
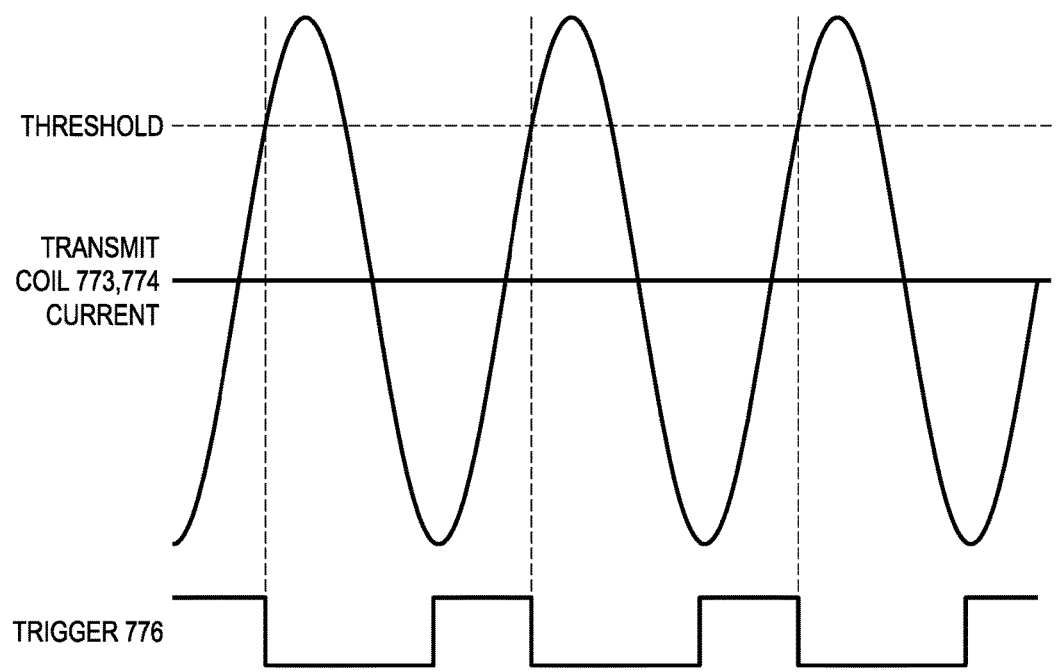
FIG. 7B illustrates voltage waveforms of selected signals depicted in the embodiment shown in FIG. 7A.

The external charging system 770 includes a resonant driver 771 for driving the series-connected transmit coils 773, 774 with an AC signal. An adjustable VBOOST voltage is conveyed on node 742 to provide a variable DC voltage for use by the driver 771 as an upper power supply node. The resonant driver 771 is responsive to a CTRL signal, such as described above, which may enable/disable the driver 771 when appropriate (e.g., after battery charging is complete within both body-implanted devices), and may also convey forward telemetry information to one or both body-implanted devices, both as described above. The external charging system 770 also includes a coil current trigger circuit 772 for generating on node 776 a TRIGGER signal conveyed to the resonant driver 771 to provide a periodic "excitation" signal to periodically pump additional energy into the resonant driver 771, which is helpful to maintain a high degree of efficiency of the resonant operation of the driver 771 in concert with the series-connected transmit coils 773, 774 connected to the output node 775 of the resonant driver 771. The coil current trigger circuit 772 preferably is configured to assert the TRIGGER signal when the instantaneous transmit coil current, during each resonant cycle, crosses a predetermined threshold that is proportional to the peak instantaneous transmit coil current. In other words, when the instantaneous transmit coil current crosses a value that is a predetermined percentage of the maximum current (e.g., 60% of peak current), the TRIGGER signal is asserted to pump the additional energy into the resonant amplifier (i.e., driver 771 and transmit coils 773, 774). Illustrative waveforms of the instantaneous transmit coil current and the TRIGGER signal are shown in FIG. 7B.

By generating a feedback-controlled TRIGGER signal in this manner, high efficiency resonant operation may be achieved even as the transmit coil current may vary. Such variation in transmit coil current may result from changes in the VBOOST voltage, from changes in transferred energy due to receive coil de-tuning within an associated charge receiving system, from forward telemetry which modulates the transmit coil (i.e., "charging coil") current, from variations in component parameters, and from changes in voltage, temperature, or other environmental conditions.

Headset Charging (Charge Delivery) System

Figures 8, 9, 9A, 9B:
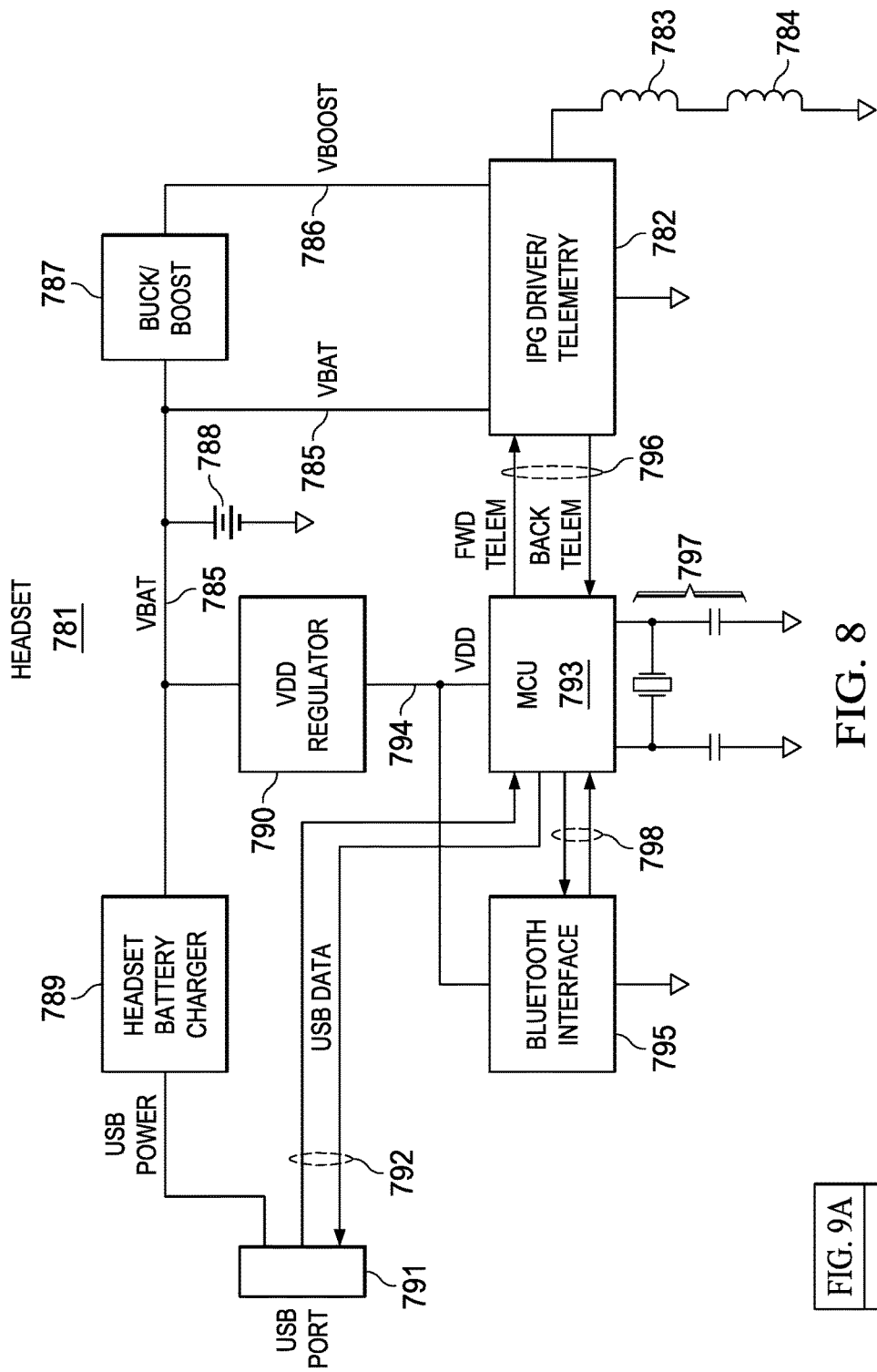
FIG. 8 is a block diagram of a headset that includes an external charging system for two implanted devices, in accordance with some embodiments of the invention.
FIG. 9, which includes
FIGS. 9A and 9B, is a schematic diagram of an exemplary IPG driver and telemetry circuitry block, such as that shown in FIG. 8, in accordance with some embodiments of the invention.
Figure 9A:
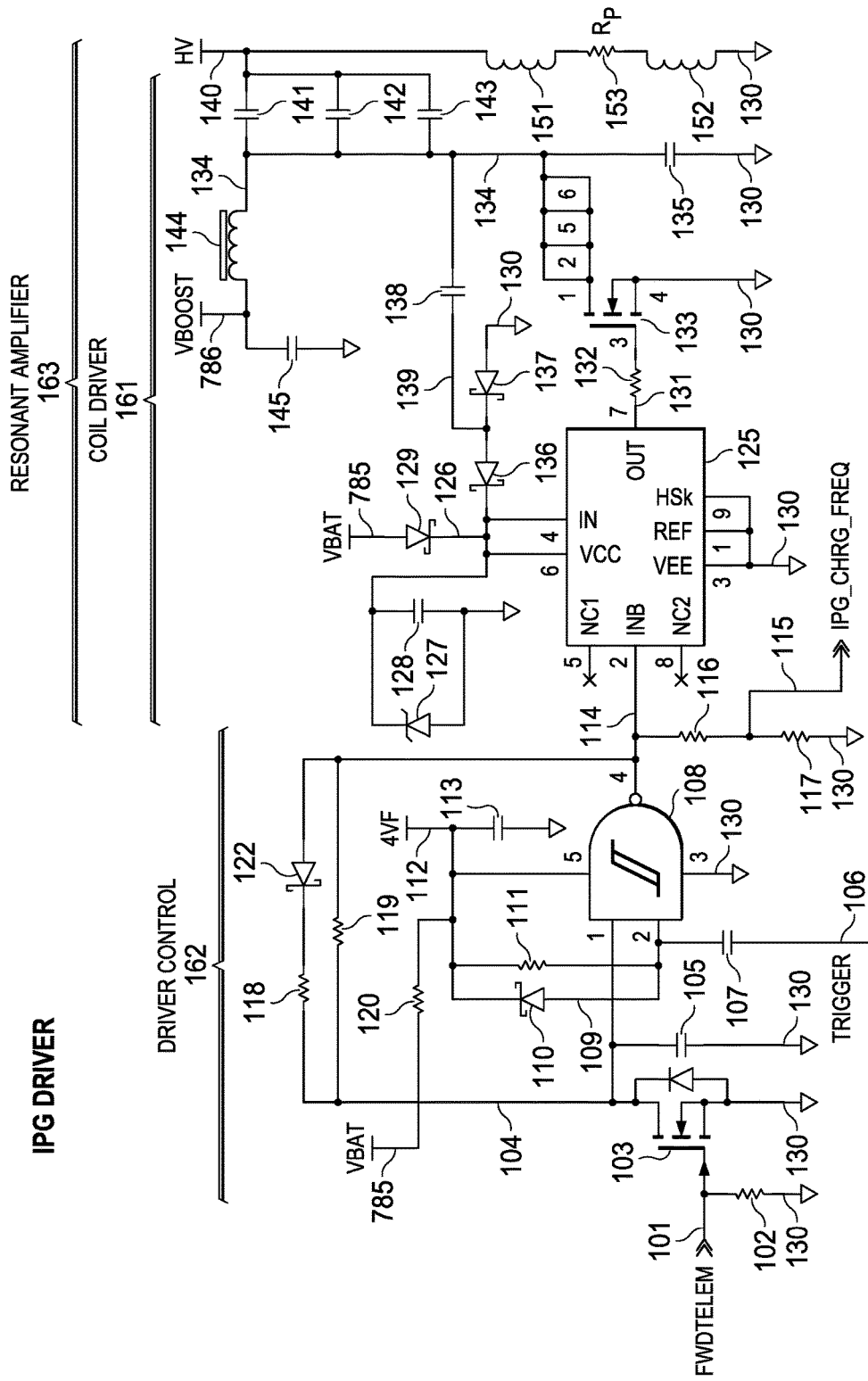
Figure 9B:
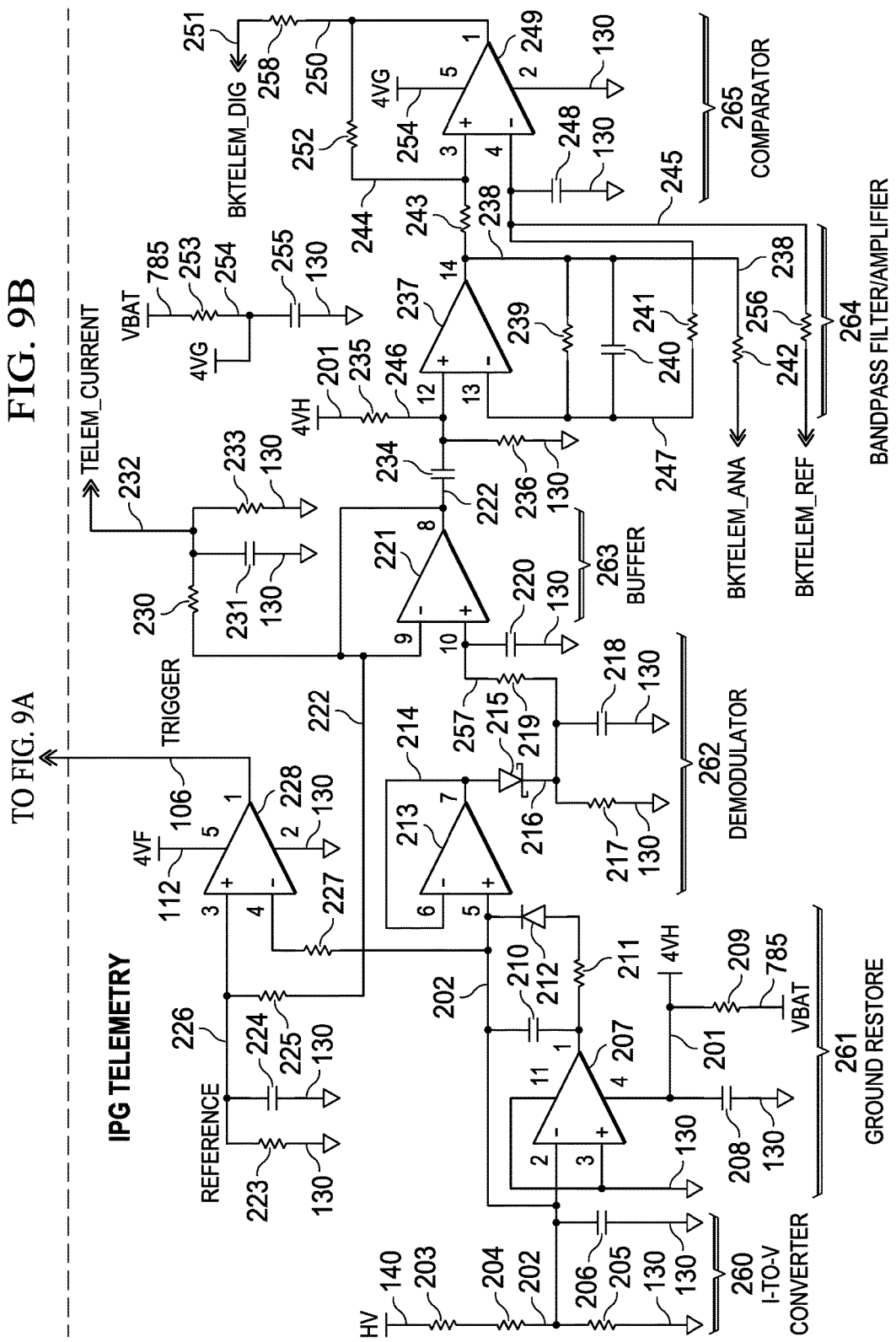

FIG. 8 is a block diagram of an exemplary headset 781 that includes an external charging system for two head-located body-implanted devices, such as two implantable pulse generator (IPG) devices. The headset includes an IPG Driver and Telemetry block 782 that drives two transmit coils 783, 784, and which is powered by a battery voltage VBAT conveyed on node 785 by headset battery 788, and an adjustable voltage VBOOST conveyed on node 786. A buck/boost circuit 787 receives the VBAT voltage on node 785 and generates the VBOOST voltage on node 786. The headset battery 788 is charged by a Headset Battery Charger 789 which receives USB power from USB port 791. A VDD regulator 790 also receives the VBAT voltage on node 785 and generates a VDD voltage (e.g., regulated to 3.0 volts) on node 794, which is generally used as a power supply voltage for certain circuitry within the headset.

A microcontroller (MCU) 793 provides general configuration control and intelligence for the headset 781, and communicates with the IPG Driver and Telemetry block 782 via a forward telemetry signal FWD TELEM and a back telemetry signal BACK TELEM via a pair of data lines 796. The MCU 793 can also communicate with an external device (e.g., a smartphone or personal digital assistant (PDA), a controller, a diagnostic tester, a programmer) that is connected to the USB port 791 via a pair of USB data lines 792. The MCU 793 is connected to an external crystal resonant tank circuit 797 for providing an accurate timing source to coordinate its various circuitry and data communication interfaces. A Bluetooth interface 795 provides wireless interface capability to an external device, such as a smartphone or other host controller, and is connected to the VDD voltage on node 794. The Bluetooth interface 795 communicates with the MCU 793 using data/control signals 798. In general, MCU 793 is utilized to store configuration information in an on-chip Flash memory for both the overall headset and charging system and also provide configuration information that can be transferred to one or more of the body-implanted devices. The overall operation of the headset is that of a state machine, wherein the IPG driver/telemetry block 782 and the other surrounding circuitry, such as the buck/boost circuit 787 and the headset battery charger 789, all function as state machines, typically implemented within an ASIC. Thus, when communication information is received that requires the MCU 793 to transfer configuration information to the body-implanted device or, alternatively, to configure the headset state machine, the MCU 793 will be activated. In this embodiment a state machine is utilized for most functionality because it has lower power operation, whereas an instruction-based processor, such as the MCU 793, requires more power. It should be understood, however, that such a headset can utilize any type of processor, state machine or combinatorial logic device.

FIG. 9, which includes FIGS. 9A and 9B, is a schematic diagram of an exemplary IPG driver and IPG telemetry circuit, such as the IPG Driver and Telemetry block 782 shown in FIG. 8. While these FIGS. 9A and 9B each represent a portion of the complete FIG. 9 and may be arranged above and below each other (aligned at the dotted line on each figure) to view the entire FIG. 9, the portion shown on FIG. 9A may be generally referred to as the IPG driver circuit, even though certain portions of the IPG driver circuit is shown in FIG. 9B, and the portion shown on FIG. 9B may be generally referred to as the IPG telemetry circuit, even though certain portions of the IPG telemetry circuit is shown in FIG. 9A.

Referring now to the complete FIG. 9, a portion of a charging (charge delivery) system is depicted which includes a coil driver 161 for a pair of series-connected transmit coils 151, 152, and a driver control circuit 162 for the coil driver 161. The coil driver 161 together with the transmit coils 151, 152 may be viewed as a resonant amplifier circuit 163. The driver control circuit 162 provides a control signal on node 114 that serves to turn off the coil driver 161 at times, and to periodically cause energy to be pumped into the resonant amplifier 163 at other times, as will be explained below.

Figure 10A:
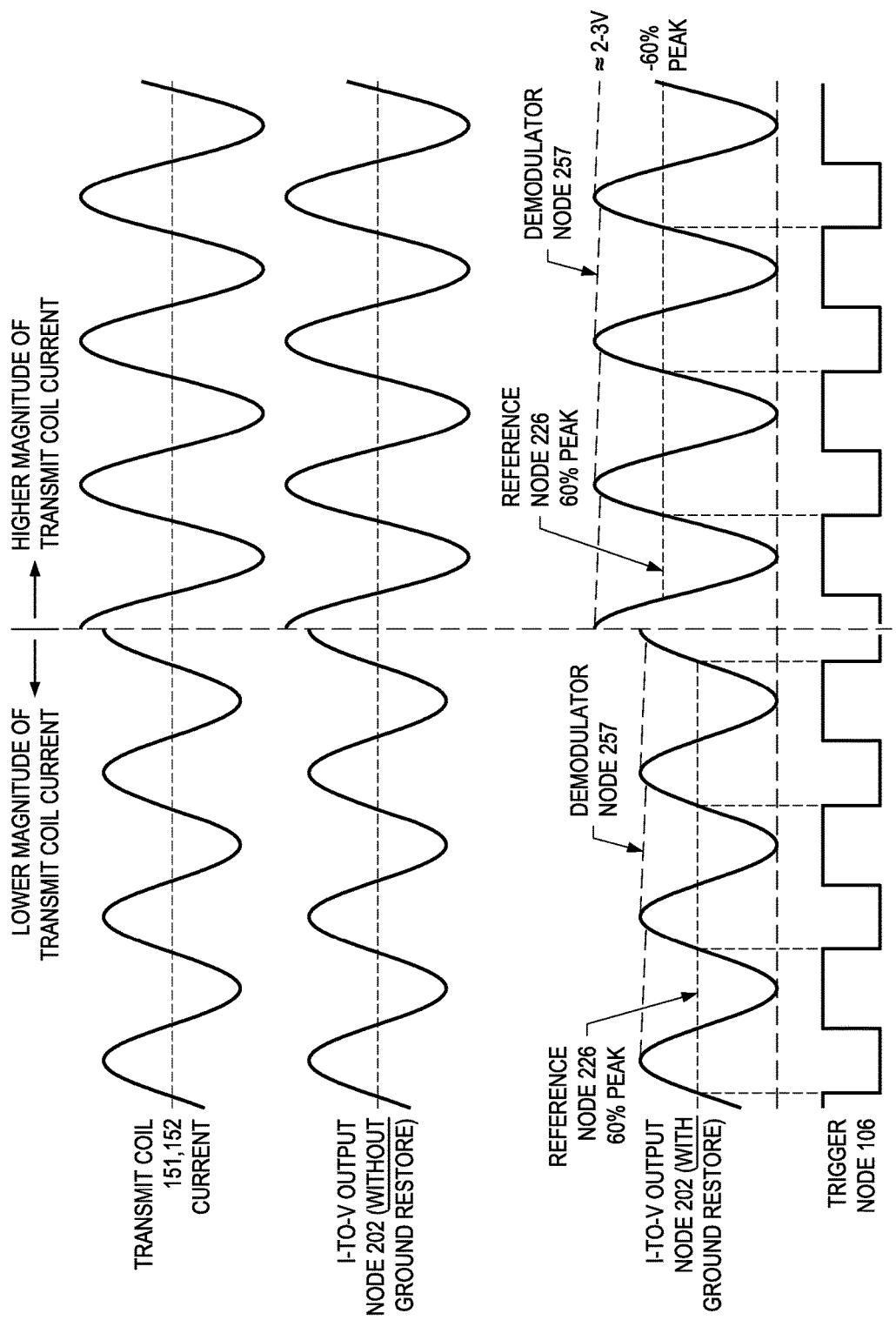
FIGS. 10A, 10B, and 10C illustrate voltage waveforms of selected signals depicted in the embodiment shown in FIG. 9 and FIG. 13A.
Figure 10B:
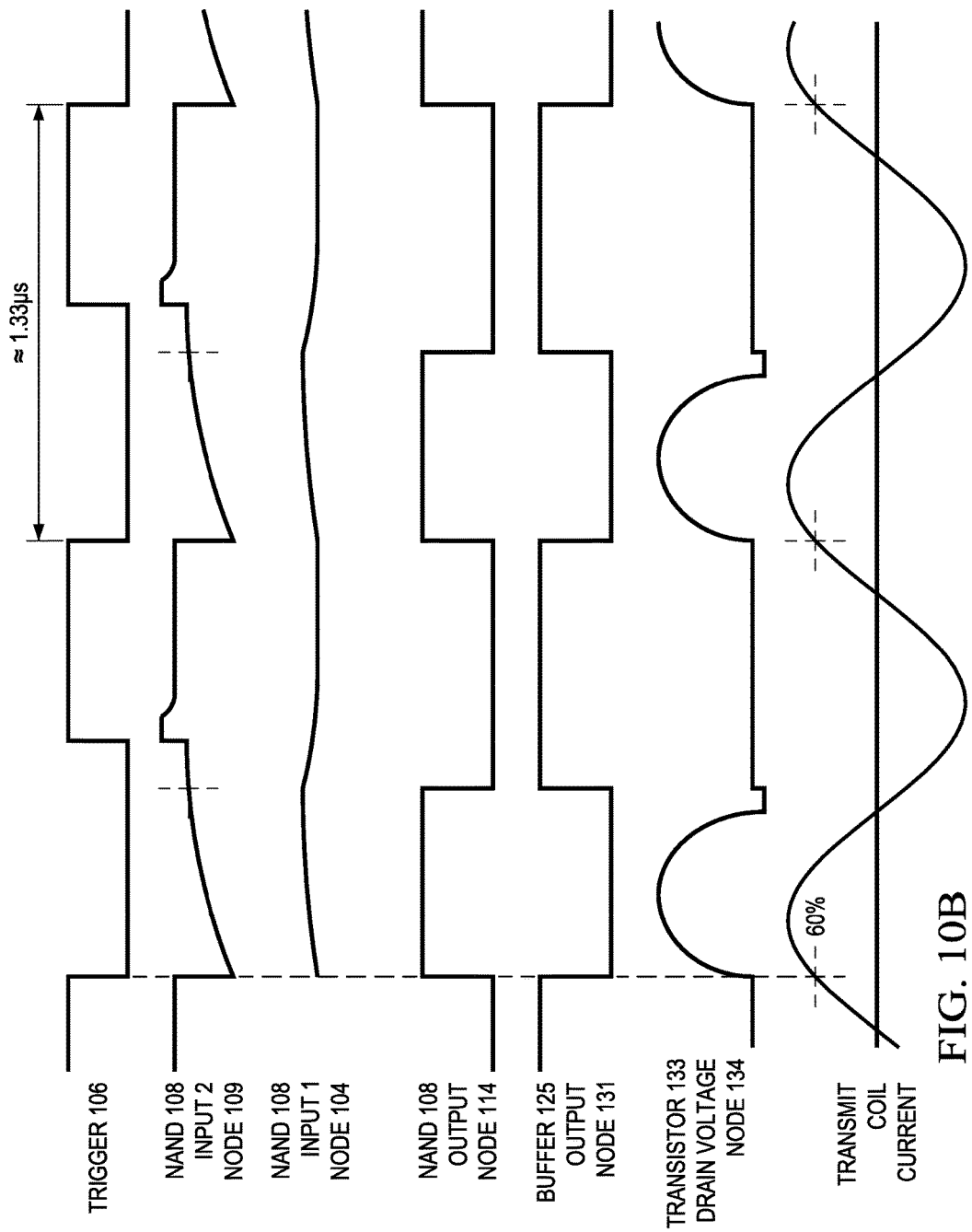
Figure 10C:
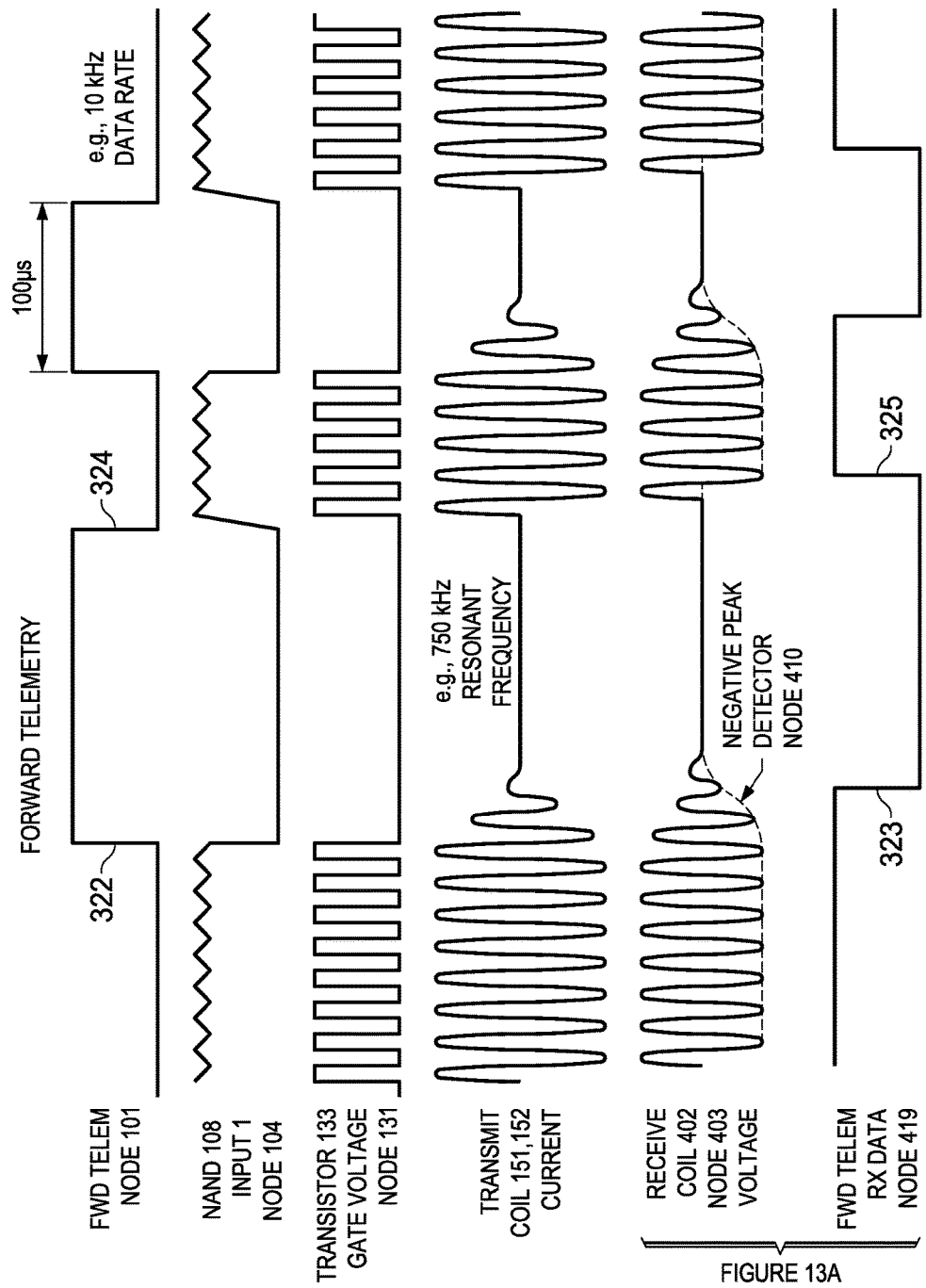

The coil driver 161 may be understood by looking first at excitation coil 144 and driver transistor 133. In resonant operation, the driver transistor 133 is periodically turned on, which drives the voltage of node 134 to ground (labeled 130). Since the excitation coil 144 is connected between node 786, which conveys a VBOOST voltage, and node 134, which is now grounded by transistor 133, the VBOOST voltage is impressed across the excitation coil 144 and consequently a current flows through the excitation coil 144, which current stores energy in the excitation coil 144. The magnitude of the VBOOST voltage may be varied (e.g., between 1.0 and 5.5 volts) to vary the amount of energy stored in the excitation coil 144 per cycle, to thus vary the amount of energy coupled to the receive coils (also referred to as "secondary coils"). Capacitor 145 provides local filtering for the VBOOST voltage conveyed on node 786. When the driver transistor 133 is then turned off, the energy in excitation coil 144 is "pumped" into the LC resonant circuit formed by parallel-connected capacitors 141, 142, 143 connected in series with the transmit coils 151, 152. Resistor 153 represents the parasitic resistance of the transmit coils 151, 152 and their associated wiring. Illustrative waveforms are shown in FIGS. 10A, 10B, and 10C. In certain embodiments, the resonant frequency is preferably on the order of 750 kHz.

Three separate capacitors 141, 142, 143 are used to distribute the peak current that would otherwise flow through the leads, solder joints, and structure of a single capacitor, to instead achieve a lower peak current through each of capacitors 141, 142, 143. But in understanding the operation of this circuit, these three capacitors 141, 142, 143 may be viewed as effectively providing a single resonant capacitor. When driver transistor 133 is turned on, it is desirable to drive node 134 to a voltage as close to ground as possible, to reduce losses that would otherwise result from a large drain-to-source current and a non-zero drain-to-source voltage across driver transistor 133. Consequently, the drain terminal of driver transistor 133 is connected by several distinct package pins to node 134.

Driver transistor 133 is controlled by the output 131 of buffer 125, which is coupled to the gate of driver transistor 133 through resistor 132. The buffer 125 is connected to operate as an inverting buffer since the non-inverting input IN (pin 4) is connected to VCC (pin 6), and the inverting input INB (pin 2) is utilized as the buffer input that is connected to node 114, which is the control signal generated by driver control circuit 162. Thus, when node 114 is low, the output node 131 of buffer 125 is high, and driver transistor 133 is turned on. The output node 131 is coupled to the gate of driver transistor 133 through resistor 132 to limit the peak current charging and discharging the gate terminal of driver transistor 133, and to also provide (together with the parasitic gate capacitance of driver transistor 133) an RC filter for the signal actually coupled to the gate terminal of driver transistor 133.

As mentioned above, when driver transistor 133 is turned on, it is desirable for node 134 to be driven to a voltage as close to ground as possible. To help achieve this, it may be likewise desirable to drive the gate terminal of driver transistor 133 to a voltage higher than the battery voltage VBAT conveyed on node 785. To accomplish this, a local power circuit including diodes 127, 129, 136, 137, and capacitors 128, 138, may be utilized.

During circuit startup, the buffer circuit 125 operates with its "VCC voltage" (conveyed on local power node 126) essentially at the battery voltage VBAT, less a small diode drop through diode 129. The VBAT voltage may be 3.5-4.0 volts, which is sufficient to operate the buffer 125 to provide adequate output voltage levels on node 131 to sufficiently turn on/off driver transistor 133 to initiate and maintain resonant operation. In such resonant operation, driver transistor 133 is preferably turned off at a particular time in each resonant cycle to pump energy into the resonant circuit, as will be explained further below. Each time that the driver transistor 133 is turned off, the voltage on node 134 rises quickly as the current through excitation coil 144 continues to flow into node 134 and charges capacitor 135. This rising voltage is coupled through capacitor 138 onto node 139, through diode 136, and onto the local power node 126 for buffer 125. The magnitude of the positive-transition of the voltage on node 134 results in a voltage on local power node 126 that may be as high as 8.0 volts, which is higher than the VBAT voltage, especially when operating in the lower range of battery voltage (e.g., as the battery discharges). When the voltage of local power node 126 rises above the VBAT voltage, diode 129 prevents any back-current into the VBAT node 785, and Zener diode 127 operates to limit, for safety reasons, the maximum voltage developed on local power node 126. Capacitor 128 provides local filtering on the local power node 126 irrespective of whether the buffer 125 is powered by the battery (through diode 129) or by resonant operation of the coil driver circuit 161 (through diode 136).

The driver control circuit 162 generates on output node 114 a driver control signal that controls when driver transistor 133 is turned on/off. In resonant operation, the driver control signal 114 is preferably a periodic signal that causes the driver transistor 133 to turn off at a predetermined time during each resonant cycle, and to turn back on at a later time during each resonant cycle, to thereby cause energy to be pumped into the resonant amplifier 163 during each resonant cycle. In addition, at certain times the driver control signal 114 is preferably driven high to cause the driver transistor 133 to turn off and remain off for a time duration longer than a resonant cycle, which prevents energy from being pumped into the resonant amplifier, and thus allows the resonant amplifier operation to decay and eventually cease.

The driver control circuit 162 includes a Schmitt-trigger NAND gate 108 having a local power supply node 112 (also labeled 4VF) which is coupled to the battery voltage VBAT using a small noise-isolation resistor 120 and a local filter capacitor 113. An input circuit includes capacitor 107, diode 110, and resistor 111, which together generate a first input signal on node 109 (NAND input pin 2) responsive to a TRIGGER signal conveyed on node 106. A feedback circuit includes diode 122, resistors 118, 119, and capacitor 105, which together generate a second input signal on node 104 (NAND input pin 1) responsive to the driver control signal generated on the output node 114.

To understand operation of the driver control circuit 162 during normal operation of the resonant amplifier circuit 163, assume that the TRIGGER signal 106 is high, both inputs of NAND 108 (nodes 104, 109) are high, and the output of NAND 108 (driver control signal 114) is low. Consequently, node 131 is high (due to inverting buffer 125) and driver transistor 133 is turned on, driving node 134 to ground and causing current to flow from VBOOST (node 786) through the excitation coil 144 to ground.

As will be explained in detail below, the TRIGGER signal on node 106 is then driven low, thus creating a falling-edge (i.e., negative transition) on the voltage of node 106. Capacitor 107 couples this negative transition to node 109, which is coupled to a voltage below the lower input threshold of Schmitt NAND gate 108. As a result, the output node 114 is driven high, node 131 is driven low, and transistor 133 is turned off. This happens almost immediately after the falling edge of the TRIGGER signal 106.

With the TRIGGER signal 106 still low, the resistor 111 will charge node 109 until its voltage reaches the upper input threshold of Schmitt NAND gate 108, at which time the NAND gate 108 output node 114 is again driven back low, node 131 is driven high, and transistor 133 is turned on. The values of resistor 111 and capacitor 107 are chosen, in concert with the upper and lower input thresholds of the Schmitt NAND gate 108, to determine the output high pulse width of output node 114, and thus determine the length of time that transistor 133 is turned off.

When the TRIGGER signal 106 is driven back high, this positive transition is coupled by capacitor 107 to node 109, but the coupled charge is snubbed by diode 110 to prevent an excessive positive voltage that would otherwise be generated at node 109, and instead maintain the voltage of node 109 at essentially the VBAT voltage.

If there are no transitions of the TRIGGER signal 106, the voltage of node 109 (NAND input pin 2) remains high, and the feedback circuit (diode 122, resistors 118, 119, and capacitor 105) causes the output node 114 to oscillate. This occurs because the voltage of node 104 (NAND input pin 1) slowly follows the voltage of the output node 114 due to the RC circuit formed by the feedback resistors 118, 119 (and diode 122) coupled between the output node 114 and input node 104, and the capacitor 105 coupled to node 104 itself. Diode 122 is included so that the parallel combination of resistors 118, 119 charges node 104 after a positive-going output transition, while only resistor 119 discharges node 104 after a negative-going output transition. This asymmetry helps keep node 104 nominally very close to the VBAT level during normal resonant operation, to essentially disable the "watchdog timer" aspect of this circuit as long as periodic TRIGGER signals are received.

The component values of resistors 118, 119 and capacitor 105 are preferably chosen so that the self-oscillation frequency of node 114 is much lower than the resonant frequency of operation (and likewise the expected frequency of the TRIGGER signal 106 during resonant operation, as will be explained in greater detail below). In some embodiments the self-oscillation frequency is approximately 3-4 times lower than the resonant frequency. This self-oscillation provides a suitable periodic conduction path through driver transistor 133 to initiate operation of the resonant amplifier 163 until the TRIGGER signal 106 is generated per cycle, which provides for more efficient operation and greater spectral purity of the resonant amplifier circuit 163. Resistors 116 and resistor 117 form a voltage divider to generate on node 115 an IPG_CHRG_FREQ signal reflective of the actual charger frequency A forward telemetry data signal FWDTELEM conveyed on node 101 is coupled to the gate terminal of NMOS transistor 103, which terminal is coupled to ground 130 by biasing resistor 102. The operation described thus-far above assumes that the FWDTELEM signal remains at ground, and thus transistor 103 remains turned off. If the FWDTELEM signal is driven high, NAND gate 108 input node 104 is driven to ground, which causes the NAND gate 108 output node 114 to be driven high, irrespective of the second NAND input node 109. This, of course, turns off driver transistor 133 for as long a time as FWDTELEM remains high, and causes resonant operation of the resonant amplifier circuit 163 to decay and eventually, if disabled for a long enough time, to cease entirely. Then, when the FWDTELEM signal is driven back low and transistor 103 turns off, the driver control circuit 162 begins to self-oscillate, thus starting operation of the resonant amplifier circuit 163 and the eventual generation of the TRIGGER signal 106 to more precisely control the timing of driver transistor 133. Such resonant "lock-in" occurs fairly quickly, usually in only 1-2 cycles. In some embodiments, the resonant frequency is approximately 750 kHz, and the forward data rate is approximately 10 kHz (i.e., a 100 μS bit interval), and the time required for the resonant amplifier 163 to decay (when FWDTELEM is driven high), and to re-start and lock-in resonant operation (when FWDTELEM is driven low), is a small portion of an individual bit interval. A more detailed description of such forward data transmission, including receiving such transmitted data in a charge receiving system, follows below.

As described above, in normal resonant operation the negative transition of the TRIGGER signal 106 determines when the driver transistor 133 is turned off during each resonant cycle of the amplifier circuit 163, and the RC input circuit on node 109 determines how long the driver transistor 133 remains off. Preferably the driver transistor 133 has a 30% duty cycle (i.e., turned off 30% of the time). In this implementation, feedback circuitry shown in FIG. 9B is utilized that generally tracks the actual current through the transmit coils 151, 153, and generates the negative-going transition of the TRIGGER signal 106 at a time during each resonant cycle when the increasing instantaneous transmit coil current exceeds a predetermined percentage of the peak current through the transmit coils 151, 152. Careful selection of the predetermined percentage improves the efficiency of resonant amplifier operation and reduces unwanted harmonic components of the oscillation frequency.

The generation of the TRIGGER signal 106 begins with a current-to-voltage converter circuit 260 formed by the series-connected resistors 203, 204 and capacitor 206 coupled between the HV node 140 (the same node driving the series-connected transmit coils 151, 152) and ground 130. Resistor 205 is a biasing resistor. With proper selection of component values, the instantaneous voltage generated at node 202 will be proportional to the instantaneous current through the transmit coils 151, 152. Such may be achieved by proper selection of the resistor and capacitor values in the current-to-voltage converter circuit 260 to achieve the same time constant as the inductor and parasitic resistor values in the transmit coils. Specifically, the values are preferably chosen so that R/C=L/R. Referencing the actual components, this relationship is then $(R_{203}+R_{204})/C_{206}=(L_{151}+L_{152})/R_{p153}$ (e.g., where $R_{203}$ means the value of resistor 203). If this relationship is followed, the instantaneous voltage at node 202 is an AC voltage that is proportional to (i.e., corresponds to) the instantaneous AC current through the transmit coils 151, 152. Normally, this AC voltage on node 202 would be symmetric and centered around the ground voltage, as shown in FIG. 10A, but in this embodiment the AC voltage on node 202 is offset to a non-negative voltage range by a ground restore circuit 261.

The ground restore circuit 261 includes an amplifier 207 having a local power supply node 201 (also labeled 4VH) which is coupled to the battery voltage VBAT (conveyed on node 785) using a small noise-isolation resistor 209 and a local filter capacitor 208. The amplifier 207 non-inverting input (pin 3) is coupled to ground, and the inverting input (pin 2) is coupled to node 202. A feedback circuit includes capacitor 210, resistor 211, and diode 212. In operation, this ground restore circuit 261 translates the AC voltage signal on node 202 to a non-negative voltage signal of the same magnitude, whose peak low voltage is ground, and whose peak high voltage is twice that otherwise generated on node 202 in the absence of the ground restore circuit 261. This resulting waveform for node 202 is shown in FIG. 10A. The peak voltage at node 202 may be 2-3 V.

The signal on node 202 is coupled to a demodulator circuit 262 that includes amplifier 213, diode 215, resistors 217, 219, and capacitors 218, 220. Node 202 is coupled to the non-inverting input (pin 5) of amplifier 213. The inverting input (pin 6) of amplifier 213 is coupled to the output node 214 to achieve operation as a voltage follower. Diode 215 and capacitor 218 generate on node 216 a voltage corresponding to the peak voltage driven onto node 214 by amplifier 213 (less a small voltage drop through diode 215), and bleeder resistor 217 reduces the voltage on node 216 if the peak voltage on node 214 assumes a lower value corresponding to a decrease in the current through the transmit coils 151, 152. Such a situation will be more fully described below in the context of back telemetry. Lastly, the peak voltage on node 216 is RC-filtered by resistor 219 and capacitor 220 to generate on node 257 a signal having less ripple than the signal on node 216. This signal on node 257 is then buffered by the buffer 263 which includes an amplifier 221 (also configured as a voltage follower) to generate on node 222 a more robust signal representing the magnitude of the peak current through the transmit coils 151, 152. Resistors 230, 233 and filter capacitor 231 generate a TELEM_CURRENT signal on node 232 having a scaled magnitude relative to the peak transmit coil current represented by node 222. In this implementation, with preferred values of the resistors 230, 233, the TELEM_CURRENT signal has a magnitude that is one-half the magnitude of the peak transmit coil current.

Comparator 228 is configured to essentially "compare" the instantaneous transmit coil current against a percentage of the peak transmit coil current, and generate the falling-edge on the TRIGGER signal 106 during each cycle of resonant operation when the rising edge of the instantaneous transmit coil current rises above a predetermined percentage of the peak transmit coil current.

The voltage signal on node 202 corresponds to the instantaneous transmit coil current, which is coupled through resistor 227 to the inverting input of comparator 228. The peak transmit coil current signal on node 222 is divided by a resistor divider formed by resistors 225, 223 to generate on node 226 a reference signal representing a predetermined percentage of the peak transmit coil current. Capacitor 224 provides local filtering to stabilize this signal on node 226, which is coupled to the non-inverting input of comparator 228. When the inverting input of comparator 228 rises above the non-inverting input, the output signal TRIGGER on node 106 is driven low, as is depicted in FIG. 10A.

The "peak transmit coil current" signal on node 222 varies as one or more secondary coils is de-tuned, such as would occur to indicate that charging is complete (if such de-tuning occurs continuously) or to communicate back telemetry data from one of the body-implanted devices (if such de-tuning is performed corresponding to a bit-serial data stream). The TELEM_CURRENT signal on node 232 is preferably configured to correspond to slowly changing values of the peak transmit coil current, while the remaining circuitry to the right of amplifier 221 is utilized to detect more frequent (i.e., higher frequency) changes in the transmit coil current, as would occur during back telemetry of data from one of the body-implanted devices.

The buffer 263 output signal on node 222 is AC-coupled through capacitor 234 to node 246, which is nominally biased by resistors 235, 236 at one-half the 4VH voltage on node 201, which essentially is the VBAT voltage on node 785. Thus, node 246 has a nominal DC bias equal to VBAT/2, upon which is superimposed an AC signal corresponding to changes in the magnitude of the peak transmit coil current. This node 246 is coupled to an input of a band-pass filter/amplifier 264, which includes an amplifier 237, resistors 239, 241 and capacitors 240, 248. Specifically, node 246 is coupled to the non-inverting input of amplifier 237. Feedback resistor 239 and capacitor 240 are each coupled between the output node 238 of amplifier 237 and the inverting input node 247 of amplifier 237.

The band-pass filter/amplifier 264 generates on its output node 238 an analog signal representing received data. This analog data signal is coupled through resistor 242 to generate an analog "back telemetry" signal BKTELEM_ANA. The band-pass filter/amplifier 264 also generates on node 245 a reference signal corresponding generally to the midpoint of the transitions of the analog data signal on node 238, which is the same bias level (e.g., VBAT/2) as node 246. This signal is coupled through resistor 256 to generate a reference "back telemetry" signal BKTELEM_REF. Both the BKTELEM_ANA and BKTELEM_REF signals may be conveyed to control circuitry (not shown) and may be used as diagnostic test points.

The gain of the band-pass filter/amplifier 264 is determined by the value of resistor 239 divided by the value of resistor 241. In certain preferred implementations, the gain may be equal to 10. The value of capacitor 240 is selected to provide the desired high frequency rolloff, and the value of capacitor 248 is selected to provide the desired low frequency rolloff.

The analog data signal on node 238 and the analog reference signal on node 245 are coupled to a comparator circuit 265 to generate on its output node 250 a digital signal representing the back telemetry data signal. The comparator circuit 265 includes a comparator 249 having a local (4VG) power supply node 254 which is coupled to the battery voltage VBAT (conveyed on node 785) using a small noise-isolation resistor 253 and a local filter capacitor 255. In this implementation, the comparator circuit 265 is preferably configured to provide a voltage gain of 27, which is determined by the input resistor 243 connected between node 238 (i.e., the output node of the band-pass filter/amplifier circuit 264) and the non-inverting input node 244 of comparator 249, and the feedback resistor 252 connected between the output node 250 of comparator 249 and the non-inverting input node 244 of comparator 249. The voltage of this non-inverting input node 244 is compared to the data reference voltage coupled to the inverting input node 245 of comparator 249 to generate on output node 250 the digital signal representing the back telemetry data signal. This digital signal is coupled through resistor 258 to generate on node 251 a digital back telemetry data signal BKTELEM_DIG.

Figure 11:
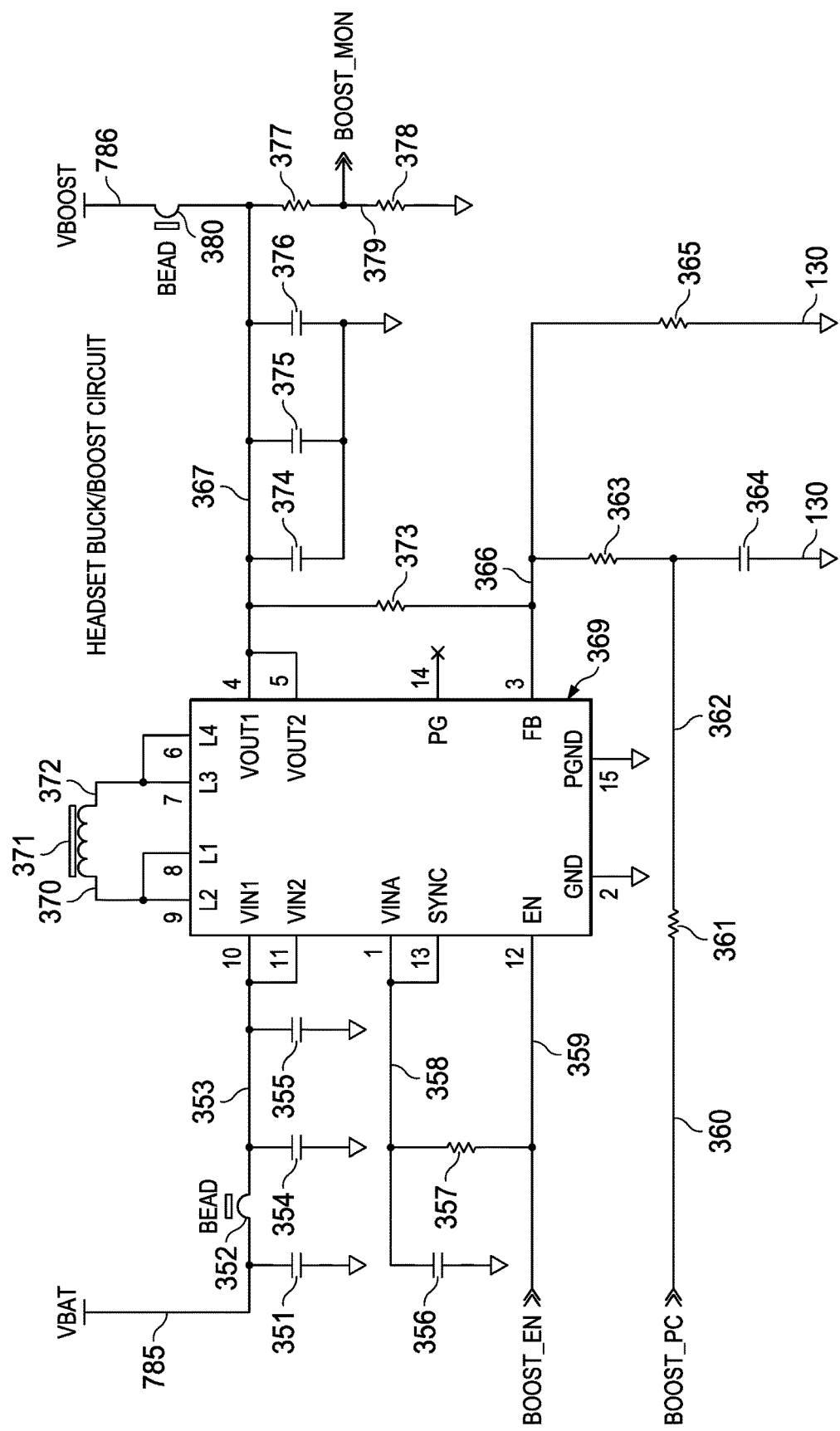
FIG. 11 is a schematic diagram of an exemplary headset buck/boost voltage generator circuit, such as that shown in FIG. 8, in accordance with some embodiments of the invention.

FIG. 11 is a schematic diagram of an exemplary headset buck/boost circuit, such as the buck/boost circuit 787 shown in FIG. 8. In this embodiment, the buck/boost circuit utilizes a commercially available high efficiency single-inductor buck-boost converter circuit 369, such as the TPS63020 from Texas Instruments, Inc. The VBAT voltage conveyed on node 785 is coupled to an input filter circuit that includes capacitor 351, ferrite bead 352, and capacitors 354, 355, whose output on node 353 is coupled to a pair of voltage input pins VIN1, VIN2 of the converter circuit 369. A single inductor 371 is coupled between a first pair of connection pins L1, L2 (node 370) and a second pair of connection pins L3, L4 (node 372). The output of the converter circuit 369 is provided on a pair of output pins VOUT1, VOUT2, which are coupled via node 367 to an output filter circuit that includes capacitors 374, 375, 376 and ferrite bead 380, to provide the VBOOST voltage on node 786. A precision resistor divider 377, 378 provides a monitoring voltage BOOST_MON on node 379.

A boost enable input signal BOOST_EN is coupled via node 359 to an enable input EN of the converter circuit 369, and also coupled to an RC-filter circuit formed by resistor 357 and capacitor 356, whose output on node 358 is coupled to a VINA pin (supply voltage for the control stage) and SYNC pin (enable/disable power save mode; clock signal for synchronization) of the converter circuit 369. The converter output voltage on node 366 is coupled to a voltage divider circuit that includes resistors 373, 365 to generate on node 366 a feedback voltage which is coupled to the FB input of the converter circuit 369. A boost PC input signal BOOST_PC is coupled via node 360 to a voltage divider adjustment circuit that includes resistors 361, 363 and capacitor 364, each coupled to node 362, and whose output is coupled to node 366. In this manner the BOOST_PC signal can essentially alter the voltage divider ratio to adjust the output voltage of the converter 369 and thus alter the VBOOST voltage.

Figure 13A:
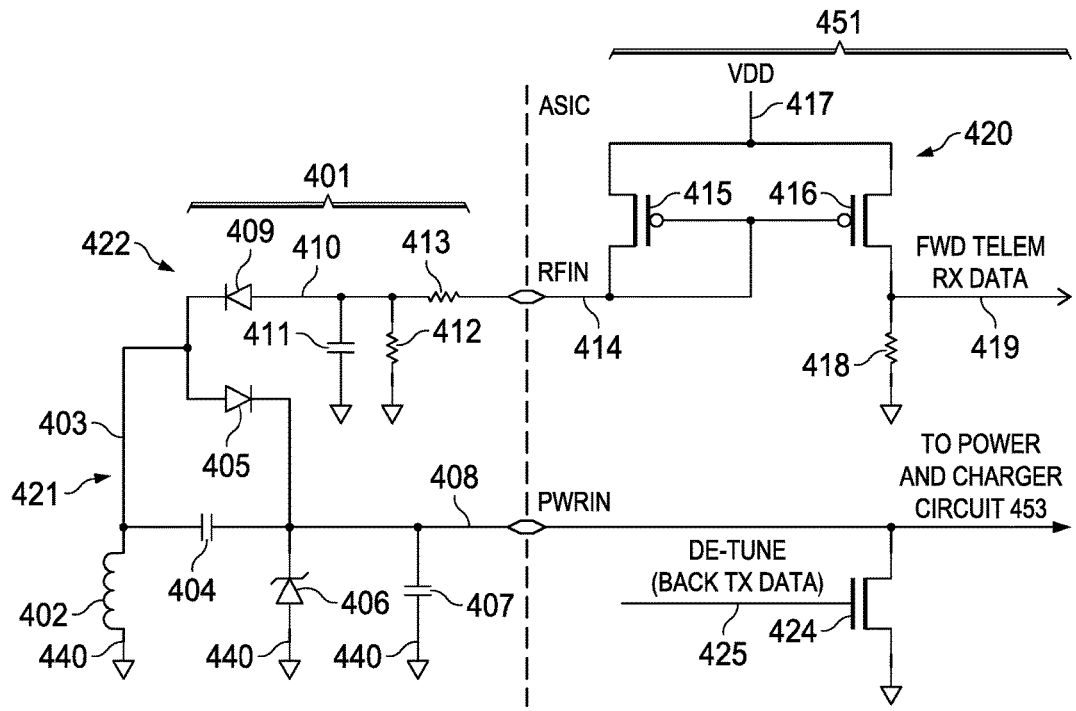
FIG. 13A is a schematic diagram of an exemplary rectifier circuit and telemetry/de-tune circuit, such as those shown in FIG. 12, in accordance with some embodiments of the invention.

As noted above, FIGS. 10A, 10B, and 10C illustrate voltage waveforms of selected signals depicted in the embodiment shown in FIG. 9, and also several signals depicted in FIG. 13A. FIG. 10A generally illustrates waveforms related to sensing the transmit coil current and generating the TRIGGER signal accordingly. The various waveforms show the transmit coil current, the I-to-V Converter 260 output signal on node 202 without the effect of the ground restore circuit 261, the I-to-V Converter 260 output signal on node 202 with the effect of the ground restore circuit 261, the demodulator node 257, the reference node 226 (shown having a value equal to 60% of the peak voltage on node 257), and the resulting TRIGGER signal on node 106. The left half of the figure corresponds to a lower magnitude of transmit coil current, and the right half of the figure corresponds to a higher magnitude of transmit coil current.

FIG. 10B generally illustrates waveforms related to the driver control 162 and the resonant amplifier 163. Shown are the TRIGGER signal on node 106, the resulting waveform on NAND 108 input 2 (node 109), the NAND 108 input 1 (node 104), the resulting waveforms on the NAND 108 output node 114, and the buffer 125 output node 131, the resulting voltage on the drain terminal of transistor 133 (node 134), and the current through the transmit coils 151, 152. The resonant oscillation frequency in this exemplary embodiment corresponds to an oscillation period of about 1.33 microseconds.

FIG. 10C generally illustrates waveforms related to forward telemetry operation. The upper waveform illustrates the FWDTELEM signal on node 101 conveying a serial bit stream data signal conveying several bits of information, with each bit interval, for this exemplary embodiment, being about 100 microseconds long. When the FWDTELEM signal is driven high at transition 322, the NAND 108 input 1 (node 104) is driven to ground, as shown in the second waveform, to disable the transmit coil driver 161. As a result, the previously oscillating signal on the gate node 131 of transistor 133 is likewise driven to ground, as shown in the third waveform, which disables the resonant amplifier 163 and causes the transmit coil 151, 152 current to decay and eventually cease, as shown in the fourth waveform. The fifth and sixth waveforms are described below in detail with regard to FIG. 13A, and illustrate the current in the receive coil 402 likewise decays and ceases, resulting in a corresponding signal on the negative peak detector output node 410, and a resulting falling transition 323 on the FWD TELEM RX DATA signal on node 419. An additional logical inversion of this signal may be easily accomplished to generate a data signal having the same polarity as the FWDTELEM signal on node 101.

When the FWDTELEM signal is driven low at transition 324, the NAND 108 input 1 (node 104) charges back to a high level, which allows the driver control 162 to again oscillate, initially controlled by its own feedback "watchdog timer" operation, and later under control of the TRIGGER signal. As a result, the gate node 131 of transistor 133 again exhibits an oscillating signal causing transistor 133 to periodically "pump" the resonant amplifier 163, and the transmit coil 151, 152 once again oscillates, as shown in the fourth waveform. As described below in detail with regard to FIG. 13A, the current in the receive coil 402 is induced because of the transmit coil current, resulting in a corresponding signal on the negative peak detector output node 410, and a resulting rising transition 325 on the FWD TELEM RX DATA signal on node 419.

Implantable Pulse Generator

Figure 12:
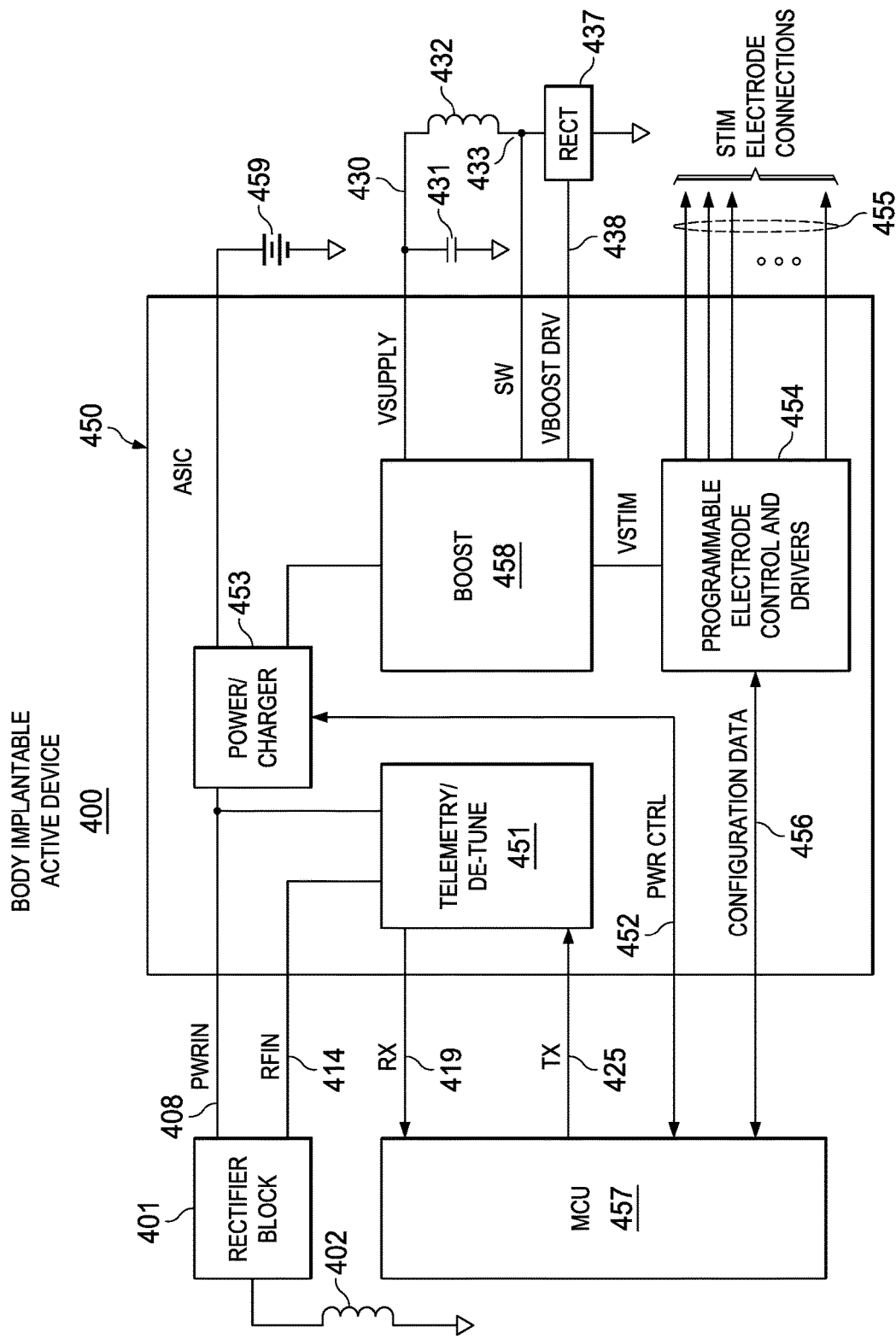
FIG. 12 is a block diagram of a body-implantable active device, in accordance with some embodiments of the invention.

FIG. 12 is a block diagram of an exemplary body-implantable active device 400, such as an implantable pulse generator (IPG) device. A receive coil 402 (also referred to as a secondary coil 402) is connected to a RECTIFIER block 401 that generates a PWRIN signal on node 408 and an RFIN signal on node 414. Both the PWRIN signal on node 408 and the RFIN signal on node 414 are connected to a TELEMETRY/DE-TUNE block 451 that receives a forward telemetry signal on the RFIN node 414, and which interacts with the PWRIN node 408 to de-tune the receive coil 402 to thereby communicate back telemetry information and/or disable further energy transfer to the receive coil 402. The PWRIN node 408 is also connected to a POWER/CHARGER block 453 that is responsible for generating one or more internal voltages for circuitry of the body-implantable device 400, and for charging battery 459.

A microcontroller (MCU) 457 provides overall configuration and communication functionality and communicates forward and back telemetry information via a pair of data lines 419, 425 coupled to the TELEMETRY block 451. Data line 419 conveys a forward telemetry RX signal, and data line 425 conveys a back telemetry TX signal. The MCU 457 receives information from and provides configuration information to/from the POWER/CHARGER block 453 via control signals PWR CTRL conveyed on control lines 452. A programmable electrode control and driver block 454 (DRIVERS 454) generates electrical stimulation signals on each of a group of individual electrodes 455. An adjustable voltage generator circuit BOOST 458, which is coupled via signals VSUPPLY (node 430), SW (node 433), and VBOOST DRV (node 438) to components external to the ASIC 450 (including capacitor 431, inductor 432, and rectifier block 437) provides a power supply voltage VSTIM to the DRIVERS block 454.

The MCU 457 provides configuration information to the DRIVERS block 454 via configuration signals CONFIGURATION DATA conveyed on configuration lines 456. In some embodiments, the POWER/CHARGER block 453, the TELEMETRY block 451, the BOOST circuit 458, and the DRIVERS block 454 are all implemented in a single application specific integrated circuit (ASIC) 450, although such is not required. In the overall operation, the ASIC 450 functions as a state machine that operates independently of the MCU 457. The MCU 457 includes Flash memory for storing configuration data from the external control system (not shown) to allow a user to download configuration data to the MCU 457. The MCU 457 then transfers this configuration data to ASIC 450 in order to configure the state machine therein. In this manner, the MCU 457 does not have to operate to generate the driving signals on the electrodes 455. This reduces the power requirements. Other embodiments may implement these three functional blocks using a combination of multiple ASIC's, off-the-shelf integrated circuits, and discrete components.

Battery charging (charge delivery) is monitored by the ASIC 450 and adjusted to provide the most efficient charging (charge delivery) conditions and limit unnecessary power dissipation. Preferable conditions for charging the battery include a charging voltage of approximately 4.5 V for most efficient energy transfer (with a minimum charging voltage of about 4.0 V). Also, it is particularly desirable to maintain a constant charging current into the battery in a battery charging operation during the entire charging time, even as the battery voltage increases as it charges. Preferably this constant charging current is about C/2, which means a charging current that is one-half the value of the theoretical current draw under which the battery would deliver its nominal rated capacity in one hour. To accomplish this, a variety of sensors and monitors (not shown) may be included within the body-implantable device 400 to measure power levels, voltages (including the battery voltage itself), charging current, and one or more internal temperatures.

FIG. 13A is a schematic diagram of an exemplary RECTIFIER block 401 and TELEMETRY/DE-TUNE block 451, both such as those shown in FIG. 12. The exemplary RECTIFIER block 401 includes a resonant half-wave rectifier circuit 421 and a half-wave data rectifier circuit 422. The resonant half-wave rectifier circuit 421 may be viewed as an "energy receiving circuit" and the half-wave data rectifier circuit 422 may be viewed as a "data receiving circuit." The exemplary TELEMETRY/DE-TUNE block 451 includes a current mirror circuit 420, and a de-tuning transistor 424.

The circuitry depicted in FIG. 13A may be viewed as a portion of a charge receiving system which includes a secondary coil 402, an energy receiving circuit (421), and a data receiving circuit (422). The resonant rectifier circuit 421 includes diode 405, capacitor 404, and capacitor 407, which together with the secondary coil 402, operates as a resonant half-wave rectifier circuit. When the secondary coil 402 is disposed in proximity to its associated transmit coil, such as one of the transmit coils 151, 152 (see FIG. 9), during a time when the resonant amplifier 163 is operating, the transmit coil and the secondary coil may be inductively coupled and may have, with careful design of the coils and reasonably close physical proximity, a Q that approaches 100. Consequently, the resonant amplifier circuit 163 and the resonant rectifier circuit 421 will operate as a resonant Class E DC-to-DC voltage converter. During such operation, energy is coupled to the secondary coil 402 due to magnetic induction.

This induced energy in secondary coil 402 is manifested as a sinusoidal voltage on node 403 that traverses above and below the ground reference level on node 440. This AC voltage on node 403 is half-wave rectified to provide a DC voltage on node 408 that may be used to provide power to both operate and/or to charge the battery (if present) within the body-implanted device. Specifically, because a single diode 405 is used in this circuit, and due to the polarity of this diode, only the positive voltage transitions on node 403 are rectified, thus creating a positive DC voltage on node 408. A zener diode 406 is coupled between node 408 and ground to prevent an excessive positive voltage from being generated at node 408.

The above description of the resonant rectifier circuit 421 and its half-wave rectifier circuit operation has assumed that transistor 424 remains off. This ensures that the Q of the combined primary transmit coil 151 and the secondary coil 402 remains high, and energy is efficiently transferred. However, if transistor 424 is turned on (when the DE-TUNE/BACK TX DATA signal on node 425 is high), the secondary coil 402 is "de-tuned" which significantly reduces the Q of the resonant circuit, and thereby reduces charge transfer and thus reduces coupled power into the secondary coil 402. This may be useful at times to reduce power, such as when the battery has been fully charged or when no charge delivery is required. It is also useful to turn on transistor 424 to communicate back telemetry information to the charging system. Analogous back telemetry operation is described above in reference to FIGS. 5A and 9, and corresponding waveforms are shown in FIGS. 5B and 10A.

The data receiving circuit 422 includes diode 409, capacitor 411, and resistor 412, which together may be viewed as a negative half-wave rectifier circuit or negative peak-detector circuit. Irrespective of whether the de-tune transistor 424 is active, the generated voltage on node 410 corresponds to the peak negative voltage of the sinusoidal voltage signal on node 403. If the peak negative voltage increases in magnitude (i.e., becomes more negative) over multiple cycles, the diode 409 will quickly drive node 410 to a correspondingly more negative voltage, and capacitor 411 serves to maintain this voltage. Conversely, if the peak negative voltage decreases in magnitude (i.e., becomes less negative) over multiple cycles, the resistor 412 will drive node 410 to a correspondingly less negative voltage. The value of resistor 412 and capacitor 411 may be chosen to provide a response time that is consistent with forward telemetry data rates. Exemplary forward telemetry data rates may be on the order of 10 kHz.

The data receiving circuit 422 together with the current mirror circuit 420 generates on node 419 a signal FWD TELEM RX DATA reflecting the forward telemetry received data. The current mirror 420 is powered by a VDD voltage conveyed on node 417, and generates a reference current through resistor 413 and P-channel transistor 415, which is mirrored by P-channel transistor 416 to generate a current through resistor 418 which generates a corresponding voltage signal on node 419. Depending upon the current gain of the current mirror 420, node 419 may be either driven virtually all the way to the VDD voltage (less a $V_{DSSAT}$ voltage of transistor 416), or may be pulled by resistor 418 well toward ground, to generate a "quasi-digital" forward telemetry receive data signal. Additional digital regeneration circuitry (e.g., within the ASIC, and not shown) may be employed to create a truly digital data signal.

Figure 13B:
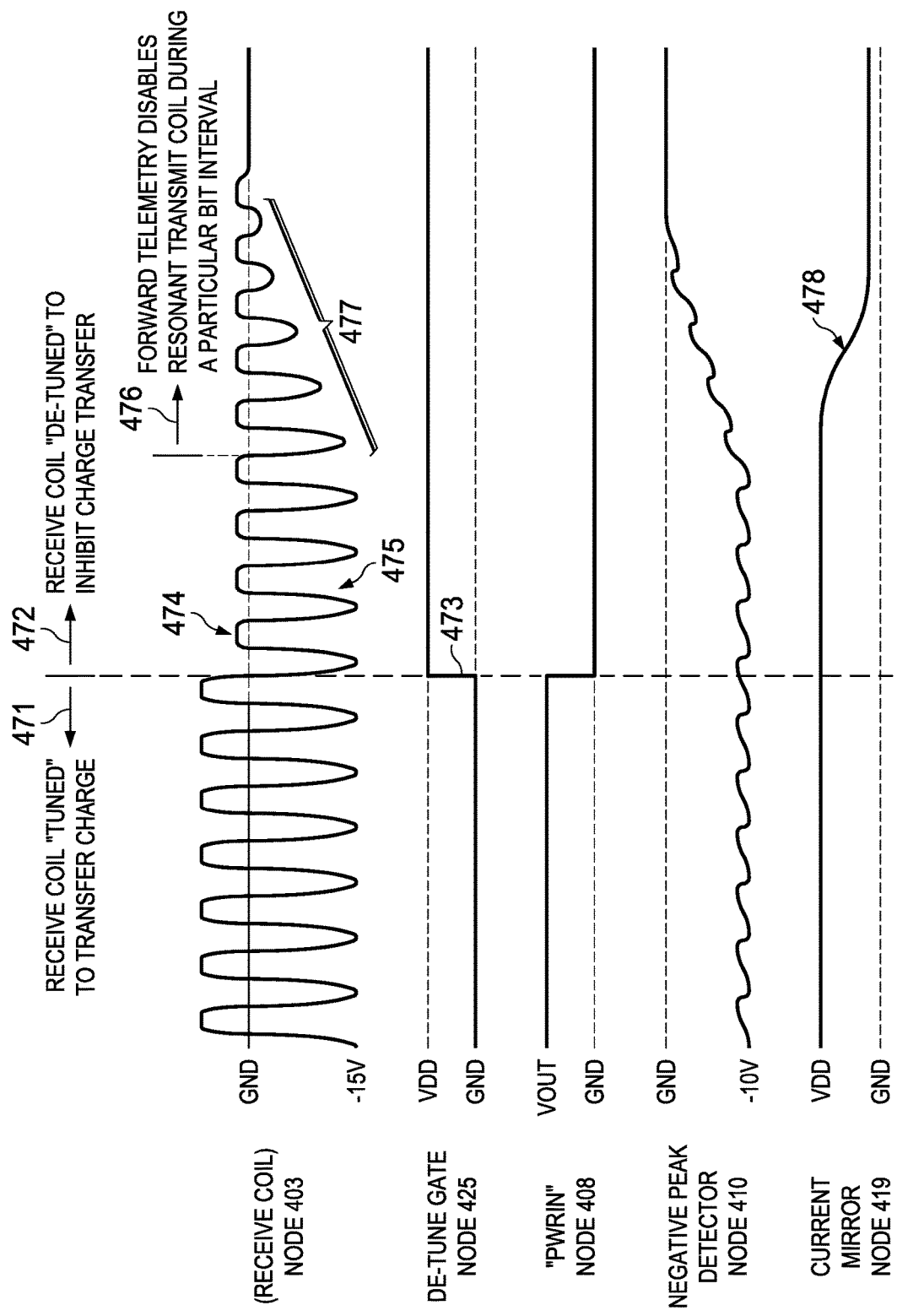
FIG. 13B illustrates voltage waveforms of selected signals depicted in the embodiment shown in FIG. 13A.

FIG. 13B generally illustrates voltage waveforms of selected signals depicted in the embodiment shown in FIG. 13A. In particular, waveforms are shown for the induced voltage at node 403 (one end of the receive coil 402), the DE-TUNE gate signal on node 425, the PWRIN signal on node 408, the negative peak detector signal on node 410, and the current mirror output node 419. The left portion 471 corresponds to the receive coil 402 being "tuned" to transfer charge, the right portion 472 corresponds to the receive coil 402 being "de-tuned" to inhibit charge transfer, in response to the transition 473 of the DE-TUNE gate signal to a high level, as shown in the second waveform. This high voltage level turns on transistor 424, which grounds node PWRIN, as shown in the third waveform, and likewise "clamps" the voltage on node 403 to a small positive voltage 474 due to diode 405, while not affecting the negative induced voltage 475 on node 403, and similarly without affecting the negative peak detector voltage on node 410 and the voltage on current mirror output node 419.

The rightmost portion 476 of the figure shows the induced voltage in receive coil decaying when the resonant amplifier in the external charging system is disabled. This could occur because the external charging system turned off its resonant amplifier in response to detecting a long term de-tuning of the receive coil in the body-implantable active device (i.e., when charge transfer is no longer desired). This could also occur in response to a back telemetry communication calling for charge transfer to cease. This could also occur merely because another bit of forward telemetry information is communicated. In any of such possible situations, the resonant amplifier 163 is disabled, which allows the resonant operation (and AC current through the transmit coils) to decay, and as a result the induced negative voltage at node 403 of the receive coil likewise decays, as shown by waveforms 477. This causes a corresponding decay in the voltage of negative peak detector node 410, and an eventual change of state 478 of the current mirror output node 419.

Figure 14:
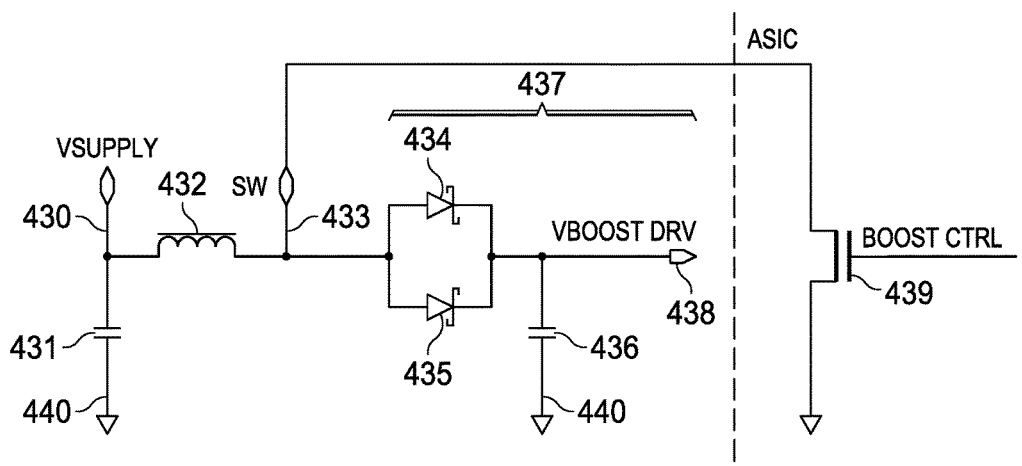
FIG. 14 is a schematic diagram of portions of an exemplary boost circuit, such as that shown in FIG. 12, in accordance with some embodiments of the invention.

FIG. 14 is a schematic diagram of portions of an adjustable voltage generator circuit, such as the adjustable voltage generator circuit BOOST 458 shown in FIG. 13, and particularly highlights the external components to the ASIC 450, in accordance with some embodiments of the invention. In this embodiment, a VSUPPLY voltage generated within the ASIC 450 and conveyed on node 430 is coupled to filter capacitor 431 and inductor 432. The other end of the inductor 432 is coupled via node 433 to the drain terminal of switch transistor 439 within the ASIC 450, which is controlled by a BOOST CTRL signal connected to its gate terminal. A pair of diodes 434, 435 and capacitor 436 together form a rectifier block 437 and serve to rectify the SW signal voltage on node 433 and thus generate the VBOOST DRV voltage on output node 438.

Figure 15:
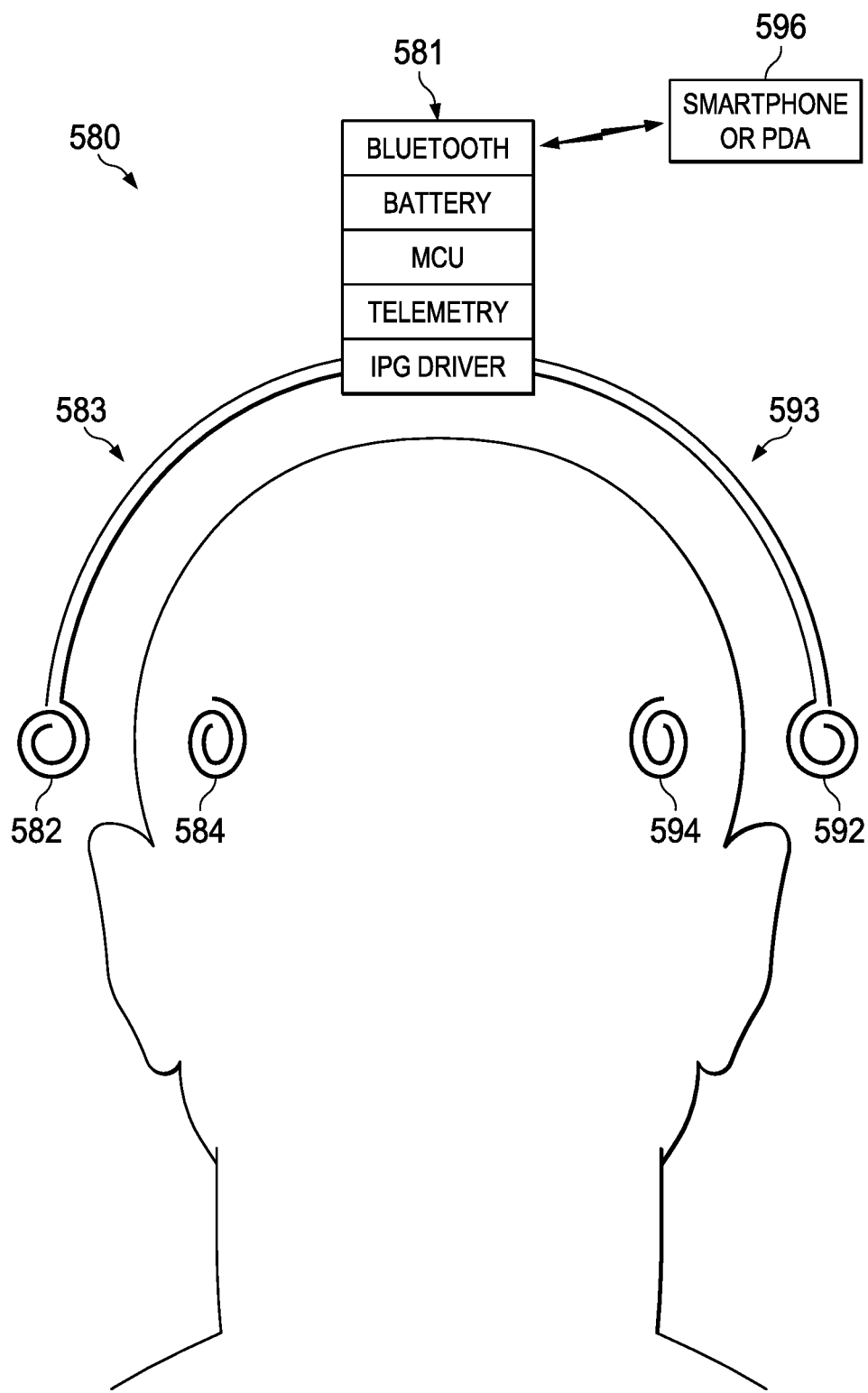
FIG. 15 is a diagram representing an exemplary headset that includes an external charging system for two separate body-implantable devices, each implanted behind a patient's respective left and right ears, and shows an associated headset coil placed in proximity to the corresponding receive coil in each implanted device.

FIG. 15 is a diagram representing a headset 580 that includes an external charging system 581 for two separate body-implantable devices, each implanted behind a patient's respective left and right ears. Each of the body-implantable devices may be a head-located neurostimulator system, such as that described below. The charging system 581 is connected to a pair of headset coils 582, 592 by respective wire pairs 583, 593. When the headset 580 is worn by a patient, the headset coils 582, 592 (transmit coils) are placed in proximity to the corresponding receive coil 584, 594 in each respective body-implanted device.

The exemplary headset 580 includes an IPG driver, telemetry circuitry, a microcontroller (MCU), a battery, and a Bluetooth wireless interface. The headset 580 may also communicate with a smartphone or PDA 596, for monitoring and/or programming operation of the two head-located neurostimulator systems.

Full Head-Located Neurostimulator System

Figure 16:
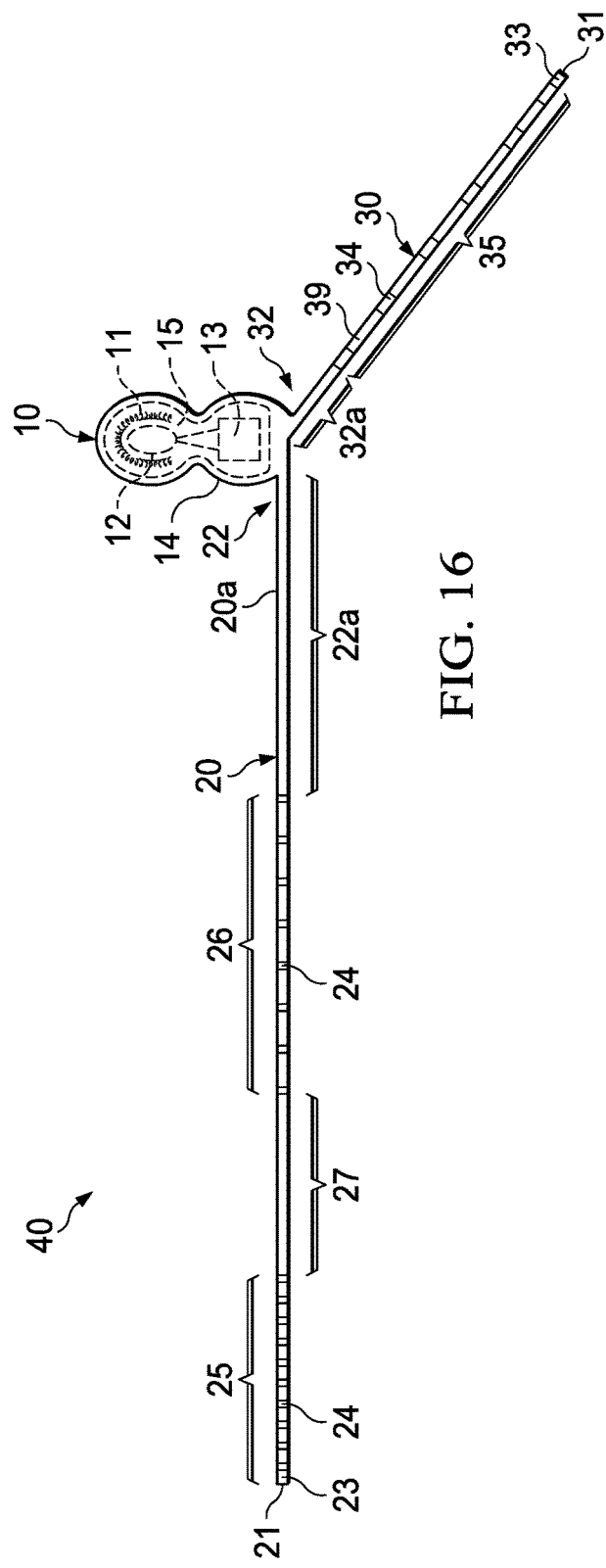
FIG. 16 depicts a side view of a head-located, unibody neurostimulator system for migraine and other head pain. The system includes an implantable pulse generator (IPG) from which two neurostimulating leads extend. Each lead includes a plurality of electrodes in a distribution and over a length to allow full unilateral coverage of the frontal, parietal, and occipital portions of the head.

FIG. 16 depicts a side view of a head-located, unibody neurostimulator system 40 for migraine and other head pain, which includes an implantable pulse generator (IPG) 10 and two unibody plastic lead extensions—a Frontal-Parietal Lead (FPL) 20 and an Occipital Lead (OL) 30 of adequate length to extend to roughly the midline of the forehead and to the midline at the cervico-cranial junction, respectively. Each lead includes a plurality of electrodes in a distribution and over a length to allow full unilateral coverage of the frontal, parietal, and occipital portions of the head. The system 40 may include a unibody construction to provide physical and functional continuity of the related components and sub-components.

The FPL 20, as part of the unibody construction, extends from the IPG 10. The FPL 20 comprises a plastic body member 20a and a set of internal conducting wires 29. The lead internal wires 29 pass along the interior of the plastic body member 20a. The plastic body member 20a is an elongated, cylindrical, flexible member, which may be formed of a medical grade plastic polymer. It has a proximal end 22, a distal end 21, and may be conceptually divided into five segments along its linear dimension. Progressing from the proximal end 22, these segments sequentially include a proximal lead segment (PLS) 22a, a parietal electrode array (PEA) 26, an inter-array interval 27, a frontal electrode array (FEA) 25, and a distal non-stimulating tip 23.

Figure 17:
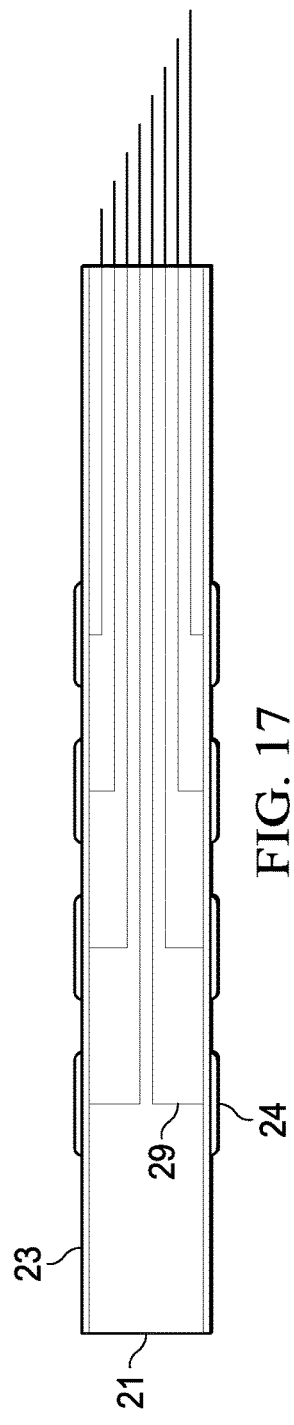
FIG. 17 depicts a side view of one of the neurostimulating leads shown in FIG. 16, and illustrates a surface electrode array. Each electrode of the array is connected to a corresponding internal wire within the neurostimulating lead.

The FEA 25 consists of a plurality of surface metal electrodes (SME) 24 uniformly disposed over a portion of the distal aspect of the FPL 20. Lead internal wires 29 connect to the SME 24 as depicted in FIG. 17, which represents the distal four SME 24 of the lead.

Returning to FIG. 16, the PEA 26 consists of a plurality of SME 24 uniformly disposed along a linear portion of the FPL 20. The PEA 26 is separated along the FPL 20 from the FEA 25 by an inter-array interval 27. It is separated from the IPG by the PLS 22a. The lead internal wires 29 connect to the individual SME 24 of the PEA 26 in the same fashion as they do with the SME 24 of the FEA 25.

The occipital lead (OL) 30, as part of the unibody construction, extends from the IPG 10. It comprises a plastic body member 39 and a set of lead internal wires 38 that pass through the central cylinder of the lead to connect to a series of SME 34 that are uniformly disposed along a portion of the length of the lead. These lead internal wires 38 pass and connect in the same manner as described above for the SME 24 of the FEA 25 as depicted in FIG. 17.

The plastic body member 39 is an elongated, cylindrical, flexible member, which may be formed of a medical grade plastic polymer. It has a proximal end 32 and a distal end 31. Progressing along the lead from the proximal end 32, these segments sequentially include a proximal lead segment (PLS) 32a, an occipital electrode array (OEA) 35, and a distal non-stimulating tip 33.

The OEA 35 consists of a plurality of surface metal electrodes (SME) 34 uniformly disposed over a portion of OL 30. Lead internal wires 38 connect to the SME 34 in the same fashion as depicted for the FEA as shown in FIG. 17.

Figure 18:
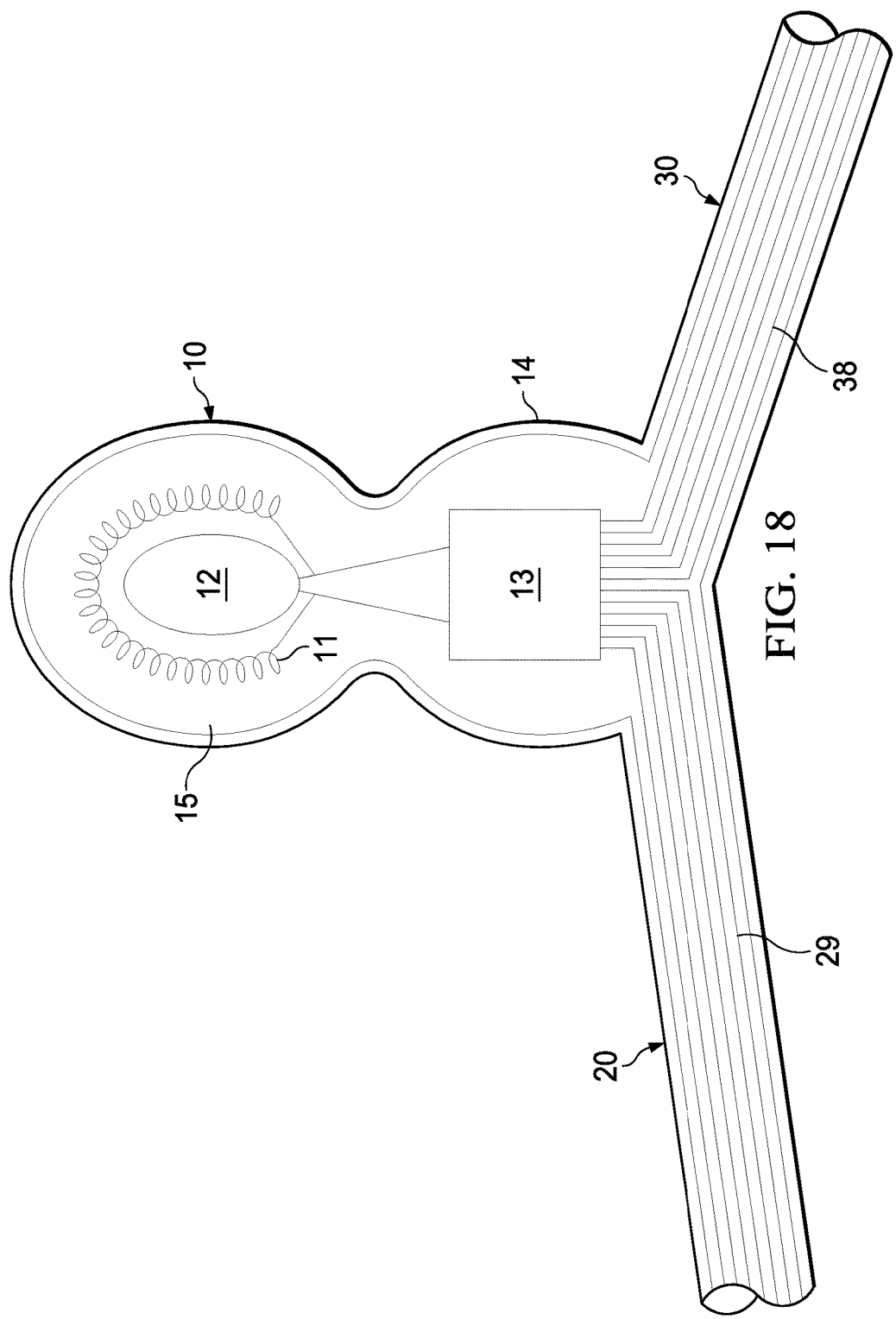
FIG. 18 depicts a side view of the internal wires exiting from the IPG's internal circuit en route to surface electrodes disposed over the two neurostimulating leads.

Referring to FIG. 16 and FIG. 18, the three primary physical and functional components of the IPG 10 include a rechargeable battery 12, an antenna (receive coil) 11, and an application specific integrated circuit (ASIC) 13, along with the necessary internal wire connections amongst these related components, as well as to the incoming lead internal wires 29, 38. These individual components may be encased in a can made of a medical-grade metal and plastic cover 14, which itself transitions over the exiting FPL 20 and OL 30.

Figure 19:
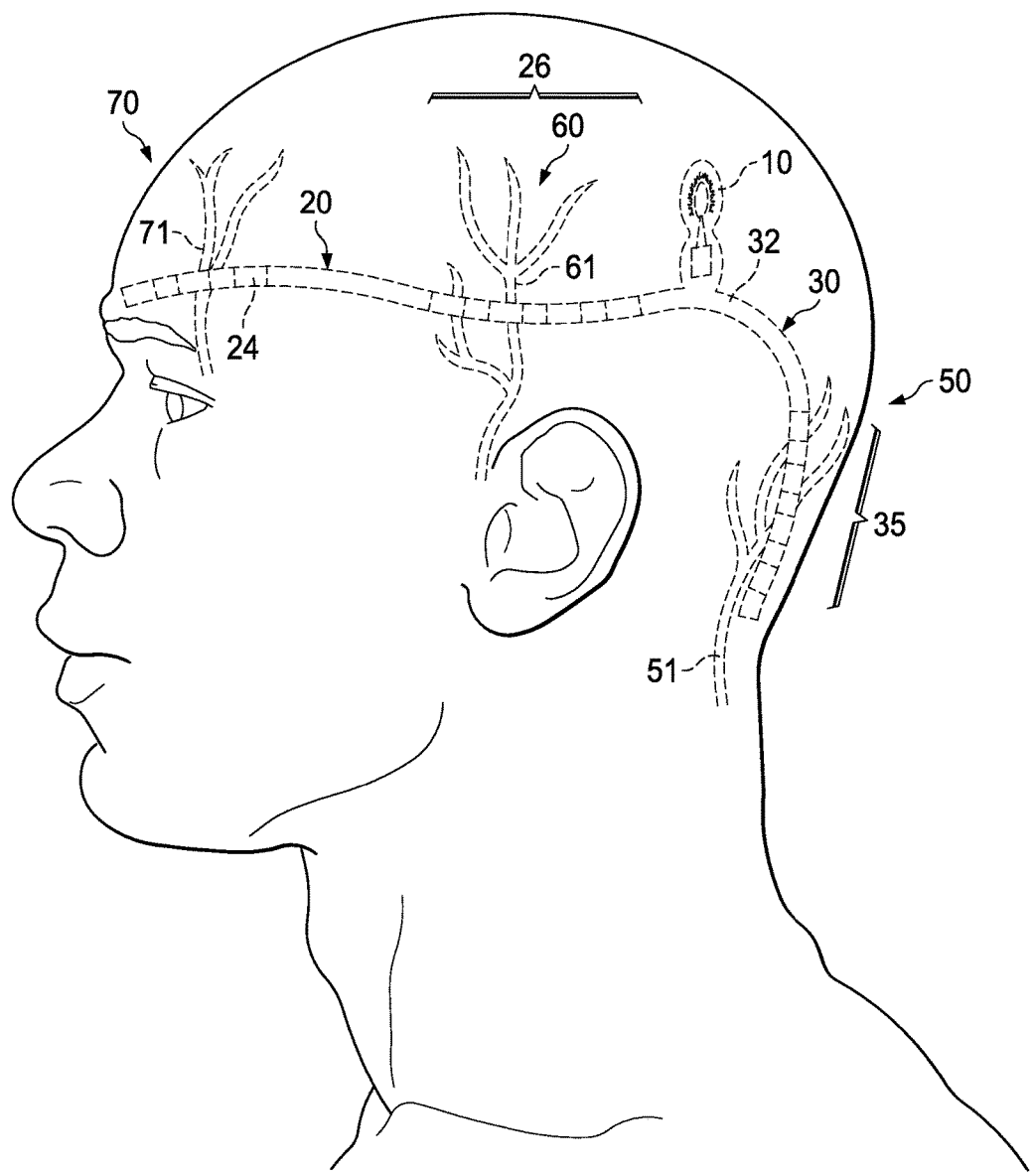
FIG. 19 depicts a side view of a head with a full head-located neurostimulator system in-situ.

FIG. 19 depicts a lateral view of the head-located, unibody neurostimulator system 40 in-situ. The unit is demonstrated in an implant position where the IPG 10 is posterior and cephalad to the pinna of the ear. The drawings demonstrate the FPL 20 passing over the parietal 60 and frontal 70 regions of the head in a manner that places the FEA 25 over the supraorbital nerve 71 and the PEA 26 over the auriculo-temporal nerve 61. The OL 30 is shown passing caudally and medially over the occipital region 50 of the head such that the OEA 35 crosses over the occipital nerve 51. Prominent here is the PEA 26, as it covers a portion of the parietal region 60 and the major associated nerves, including the auriculo-temporal nerve 61, as well as adjacent cutaneous nerves. Also depicted are the courses of the distal portion of the FPL 20 and the OL 30 as they pass over and cover the associated nerves of the frontal (supraorbital) region 70 and occipital region 50.

The overall mechanistic purpose of an implantable neurostimulation system is to generate and conduct a prescribed electrical pulse wave from an IPG 10 down a set of lead internal wires 29, 38 running a portion of the length of the lead to specified programmed set of SME 24, 34, whereby the current is then conducted by tissue and/or fluid to an adjacent, or nearby, set of one or more SME 24, 34, which in turn passes the signal proximally down the lead wire 29, 38 back to the IPG 10 and its ASIC 13, thus completing the circuit.

In certain embodiments, a body-implantable active device includes a head-located, unibody neurostimulating system comprising an IPG 10 and at least two neurostimulating leads (e.g., FPL 20 and OL 30). The system may be implanted in a manner such that the IPG 10 and two leads 20, 30 are disposed as illustrated in FIG. 19. The IPG 10 is capable of functionally connecting to and communicating with a portable programmer and an external charging system for battery recharging, such as the headset depicted in FIG. 8 and FIG. 15.

In this embodiment, the leads are constructed as described above and as depicted in the drawings. The FPL 20 is approximately 26 cm in length from its proximal end 22 to its distal end 21. The FPL 20 has a distal non-stimulating tip 23 of approximately 3 mm in length that abuts the FEA 25, which may have ten SME 24 uniformly disposed over approximately 8 cm. This is followed by an inter-array interval 27 of approximately 4 cm, then the PEA 26, which may include eight SME 24 uniformly disposed over approximately 6 cm, and finally a proximal lead segment 22a that ends at the proximal end 22, where the lead transitions to the IPG 10 and the lead internal wires 29, 38 connect to the ASIC 13.

In this embodiment, the occipital lead 30 may comprise a plastic body member 39 over which six SME 34 may be disposed uniformly over approximately a 10 cm length of the lead, and the lead terminates in approximately a 3 mm distal non-stimulating tip 33.

In this embodiment, the IPG 10 comprises the elements described above and depicted in the drawings, including an ASIC 13, a rechargeable battery 12, and an antenna coil 11, which all may be housed in a common interior 15 that may include a medical grade metal can with plastic cover 14. In this embodiment the dimensions of the IPG 10 measured along the outer surface of the plastic cover 14 may be approximately 5 cm by 3 cm by 0.5 mm.

When functioning, the electrodes of the terminal electrode array are programmed to function as anodes and cathodes, and such programming may include such parameters as pulse amplitude, frequency and pulse width. The generated electrical pulse wave then passes from a connected proximal surface metal contact, along the associated internal lead wire, and ultimately to its associated terminal surface metal electrode. The current then passes a short distance through the subcutaneous tissue to a contiguous, or nearby, electrode, whereby it passes back up the lead to its associated proximal metal contact, and then back to the pulse generator to complete the circuit. It is the generated pulse waves passing through the subcutaneous tissue between two terminal electrodes that stimulate the sensory nerves of the area. When active, the pulse generator is usually programmed to produce continuous series of pulse waves of specified frequency, amplitude, and pulse width. It is this series of pulse waves actively stimulating a patient's locally associated nerves that underpins the therapeutic effect.

While this example neurostimulation system has been described for implantation in the head and for head pain, it is capable of being implanted and used as a peripheral nerve stimulator over other regions of the head and face than those described above, and also over other peripheral nerves in the body.

Other Embodiments and Definitions

In one aspect, a system is provided for transferring power to, and communicating with, at least one body-implantable active device. In some embodiments the system includes an external power transfer system associated with an external device disposed outside of a body, operable to transfer power through a dermis layer to each body-implantable active device, and communicate data to and from each body-implantable active device, and also includes a power receiving system associated with each body-implantable active device, operable to receive power transferred from the external power transfer system, and communicate data to and from the external power transfer system.

In some embodiments the external power transfer system includes: at least one transmit coil, each corresponding to a respective body-implantable active device; a driver circuit operable to drive the at least one transmit coil with an AC signal; a forward telemetry circuit operable to modulate, responsive to a forward telemetry data input signal, a corresponding data signal within the AC signal; and a back telemetry circuit operable to generate, responsive to a data signal modulated within the AC signal, a corresponding back telemetry data output signal.

Each power receiving system respectively includes: a receive coil tuned to the resonant frequency of the corresponding transmit coil; a charge receiving circuit coupled to the receive coil, said charge receiving circuit operable in a first mode to receive power transferred from the corresponding transmit coil to the receive coil when in proximity thereto, and operable in a second mode to detune the receive coil to substantially inhibit power transfer from the corresponding transmit coil to the receive coil; a forward telemetry circuit coupled to the receive coil, being operable to generate, responsive to a modulated data signal coupled onto the receive coil, a corresponding forward telemetry data output signal; and a back telemetry circuit coupled to the receive coil, being operable to modulate, responsive to a back telemetry data input signal, a corresponding data signal onto the receive coil.

In some embodiments the external power transfer system is operable to communicate data to each power receiving system in both the first and second modes, and each power receiving system is operable to receive data communicated from the external power transfer system in both the first and second modes. In some embodiments each power receiving system is operable to communicate data to the external power transfer system in both the first and second modes, and the external power transfer system is operable to receive data communicated from each power receiving system in both the first and second modes. In some embodiments the back telemetry circuit is further operable to de-tune the receive coil in accordance with a serial bit-stream corresponding to the back telemetry data input signal, and thereby modulate the corresponding data signal onto the receive coil, and the corresponding data signal modulated onto the receive coil is communicated to the external power transfer system as a corresponding data signal modulated within the AC signal.

In some embodiments the external power transfer system includes a single transmit coil corresponding to a single body-implantable active device.

In some embodiments the driver circuit and the at least one transmit coil comprise a resonant amplifier circuit.

In some embodiments each body-implantable active device is head-locatable. In some embodiments each body-implantable active device comprises a neurostimulation pulse generator. In some embodiments the external power transfer system is disposed within a headset, and each transmit coil is co-locatable with the respective receive coil of the associated body-implantable active device.

In some embodiments the external power transfer system includes a series-connected plurality of transmit coils, each corresponding to a respective body-implantable active device, and the driver circuit is operable to drive the series-connected plurality of transmit coils with the AC signal. In some embodiments each body-implantable active device comprises a respective head-locatable neurostimulation system, and the external device disposed outside of a body comprises a headset charging and control device operable to charge and communicate with each respective head-locatable neurostimulation system. In some embodiments each body-implantable active device further comprises a battery, and a battery charging circuit coupled to the charge receiving circuit for receiving the power transferred from the external power transfer system, and providing the received power as a charging current for the battery. In some embodiments each body-implantable active device is operable in the first mode to receive power from the external power transfer system and provide the received power as the charging current for the battery, and operable in the second mode to substantially inhibit power transfer from the external power transfer system when battery charging is complete or no longer desired.

In another aspect, a system is provided for charging and communicating with at least two body-implanted active devices (BIADs), each with a battery. In some embodiments, the system includes an external charging system disposed outside of the body for transferring charging energy to the body and facilitating transmission of data to, and reception of data from, the body-implanted active devices, and also includes a charge receiving system associated with each of the body-implanted active devices for receiving energy transferred from the external charging system and facilitating transmission of data to, and reception of data from, the external charging system.

In some embodiments, the external charging system includes: a plurality of transmit coils disposed in series, each corresponding to a respective one of the body-implanted active devices; a driver circuit operable to drive the series-connected transmit coils with an AC signal; a data transmitter circuit operable to modulate a data signal within the AC signal; and a data receiver circuit operable to receive a data signal modulated within the AC signal. Each of the charge receiving systems includes: a receive coil tuned to the resonant frequency of an associated one of the transmit coils for receiving energy therefrom when in proximity thereto; a charge receiving circuit coupled to the receive coil, said charge receiving circuit operable in a first charging mode to receive energy transferred from the associated transmit coil to the receive coil, and operable in a second charging mode to detune the receive coil to inhibit transfer of energy from the associated transmit coil to the receive coil; a data receiver circuit operable to receive data from the receive coil in both the first and second modes; and a data transmitter circuit operable to transmit data to the receive coil in both the first and second modes. The external charging system is operable to transmit data to each of the associated charge receiving systems, and receive data from each of the associated charge receiving systems, in both the first and second charging modes.

In some embodiments, each of the body-implanted active devices is head-located. In some embodiments, each of the body-implanted active devices is subcutaneous within the body. In some embodiments, each of the body-implanted active devices includes an implanted pulse generator. In some embodiments, the external charging system is disposed within a headset, and each transmit coil is co-locatable with the respective receive coil of the associated body-implanted active device. In some embodiments, the external charging system includes only one driver for the two or more series-connected transmit coils. In some embodiments, the driver circuit, together with the two or more series-connected transmit coils, comprises a resonant amplifier circuit.

In some embodiments, a first one of the at least two body-implanted active devices comprises a first implanted head-located neurostimulation system; a second one of the at least two body-implanted active devices comprises a second implanted head-located neurostimulation system; and the external charging system comprises a headset charging and control device operable to charge and communicate with both the first and second implanted head-located neurostimulation systems.

In another aspect a method is provided for wirelessly charging and communicating with an implantable medical device. In some embodiments the method includes: enabling periodic excitation of a resonant inverter circuit disposed within an external control device (ECD), the resonant inverter circuit having a first primary load coil that is operatively inductively coupled with a first secondary load coil of a first resonant rectifier circuit disposed within a first implantable medical device (IMD), the resonant inverter circuit and the first resonant rectifier circuit together operable as a resonant DC-DC converter circuit at a first resonant frequency; gating the periodic excitation of the resonant inverter circuit in accordance with a forward serial data stream to be communicated from the ECD to the first IMD; rectifying, using a first half-wave rectifier circuit within the first resonant rectifier circuit, induced voltage transients of a first polarity to generate a charging voltage to power a battery charging circuit within the first IMD; and rectifying, using a second half-wave rectifier circuit within the first resonant rectifier circuit, induced voltage transients of a second polarity opposite the first polarity, to generate within the first IMD a first data signal corresponding to the forward serial data stream.

In some embodiments the gating includes: disabling the periodic excitation during each bit position of the forward serial data stream having a first digital state; and enabling the periodic excitation during each bit position of the forward serial data stream having a second digital state opposite the first digital state.

In some embodiments the forward serial data stream has a bit rate corresponding to a lower frequency than the first resonant frequency by at least a factor of 20. In some embodiments the first data signal within the first IMD corresponds to a peak value of the instantaneous per-cycle induced voltage transients of the second polarity.

In some embodiments the values of the first data signal above a first threshold level correspond to one of the first and second digital states of the forward serial data stream, and values of the first data signal below the first threshold level correspond to the other of the first and second digital states of the forward serial data stream.

In some embodiments the method further includes: de-tuning, within the first IMD, the first secondary coil together with the first rectifier circuit, to reduce the quality factor (Q) of the first resonant rectifier circuit with regard to induced transitions of the first polarity and to thereby reduce induced current coupled from the first primary coil to the first secondary coil, the de-tuning performed to communicate information from the first IMD to the ECD; and sensing, within the ECD, changes in current through the first primary coil resulting from the de-tuning of the first secondary coil by the first IMD, to thereby detect the information communicated by the first IMD.

In some embodiments the method further includes disabling, in response to receiving information communicated by the first IMD, the periodic excitation to thereby cause resonant operation of the resonant inverter circuit to decay and ultimately cease, and to consequently turn off the battery charging circuit within the first IMD.

In some embodiments the sensing comprises: generating, within the ECD, a first waveform corresponding to instantaneous per-cycle current flowing through the first primary load coil; and detecting changes in peak value of the first waveform to thereby detect the information communicated by the first IMD.

In some embodiments the de-tuning is performed to indicate the first IMD battery charging is complete.

In some embodiments: the information comprises a reverse serial data stream to be communicated from the first IMD to the ECD; the de-tuning is performed during each bit position of the reverse serial data stream having a first digital state, and the de-tuning is not performed during each bit position of the reverse serial data stream having a second digital state opposite the first digital state. In some embodiments the reverse serial data stream has a bit rate corresponding to a lower frequency than the first resonant frequency by at least a factor of 20.

In some embodiments the method further includes generating, in the ECD, a waveform corresponding to instantaneous per-cycle current flowing through the first primary load coil. In some embodiments the periodic excitation comprises pumping current into the resonant inverter circuit during a portion of each resonant cycle, beginning at a time corresponding to a predetermined percentage of peak per-cycle current flowing through the first primary load coil, and continuing for a predetermined duration.

In some embodiments the first IMD comprises an implantable head-located neurostimulation system. In some embodiments the ECD comprises a headset charging and control device for the implantable head-located neurostimulation system.

In some embodiments: the resonant inverter circuit comprises a Class E inverter circuit having an excitation coil coupled between a DC input voltage and a switch device; and the first resonant rectifier circuit comprises a first Class E rectifier circuit; and wherein the Class E inverter circuit and the first Class E rectifier circuit are together operable as an isolated Class E DC-DC converter circuit at the first resonant frequency. In some embodiments the method further includes varying the DC input voltage for the Class E inverter circuit to limit power coupled to the first IMB and to thereby increase efficiency of battery charging within the first IMB. In some embodiments the method further includes varying the DC input voltage for the Class E inverter circuit, in response to information received from the first IMB, to limit voltage drop across a voltage regulator circuit within the first IMB to thereby limit power dissipation within the first IMD.

In some embodiments: the Class E inverter circuit includes a second primary load coil in series with the first primary load coil, the second primary load coil operatively inductively coupled with a secondary load coil of a second Class E rectifier circuit disposed within a second IMD, the Class E inverter circuit and the first and second Class E rectifier circuits together are operable as isolated Class E DC-DC converter circuits at the first resonant frequency; and the method further includes: gating the periodic excitation of the Class E inverter circuit in accordance with a forward serial data stream to be transmitted from the ECD to one or both of the first IMB and second IMD; rectifying, using a first half-wave rectifier circuit within the second IMD, induced voltage transients of the first polarity to generate a charging voltage to power a battery charging circuit within the second IMD; and rectifying, using a second half-wave rectifier circuit within the second IMD, induced voltage transients of the second polarity, to generate within the second IMB a first data signal corresponding to the forward serial data stream.

In some embodiments the method further includes: de-tuning, within the first IMD, the first secondary coil together with the first rectifier circuit, to reduce the quality factor (Q) of the first resonant Class E rectifier circuit with regard to induced transitions of the first polarity and to thereby reduce induced current coupled from the first primary coil to the first secondary coil, the de-tuning performed at first times to communicate first information from the first IMB to the ECD; de-tuning, within the second IMD, the second secondary coil together with the second rectifier circuit, to reduce the quality factor (Q) of the second resonant Class E rectifier circuit with regard to induced transitions of the first polarity and to thereby reduce induced current coupled from the second primary coil to the second secondary coil, the de-tuning performed at second times to communicate second information from the second IMD to the ECD, wherein the second times may but need not overlap the first times; and sensing, within the ECD, changes in current through the series combination of the first and second primary coils resulting from either or both of the de-tuning of the first secondary coil by the first IMD and the de-tuning of the second secondary coil by the second IMD, to thereby detect either or both of the first information communicated by the first IMD and the second information communicated by the second IMD.

In some embodiments the first IMD comprises a first implantable head-located neurostimulation system; the second IMD comprises a second implantable head-located neurostimulation system; and the ECD comprises a headset charging and control device operable to charge and communicate with both the first and second implantable head-located neurostimulation systems.

While certain embodiments described herein may reference body-implanted active devices having an onboard battery, such a battery is not required, as the described charge delivery systems may be utilized to charge a battery within the body-implanted device (if present), and/or to power the body-implanted device, particularly if such body-implanted device does not include a battery.

Certain embodiments may incorporate an adjustable voltage generation circuit (e.g., a buck/boost circuit as shown in FIG. 8 and FIG. 11) that utilizes a local power supply voltage, such as a battery voltage, to generate a VBOOST voltage that is typically higher in voltage than the local power supply. However, the VBOOST voltage in certain embodiments may be higher or lower than the local power supply voltage, depending upon the battery voltage, the desired energy transfer to the body-implanted active devices, and other factors.

As used herein, "exemplary" is used interchangeably with "an example." For instance, an exemplary embodiment means an example embodiment, and such an example embodiment does not necessarily include essential features and is not necessarily preferred over another embodiment. As used herein, "coupling" includes direct and/or indirect coupling of circuit components, structural members, etc.

Certain embodiments disclosed herein may be described as including an external charging system (or external charge transfer system) for charging (or transferring charge to) one or more implantable devices. Strictly speaking, in the described embodiments using a transmit coil and a receive coil, energy is stored per cycle as a magnetic field in the transmit coil, and some of this energy is transferred per cycle by magnetic induction to the receive coil. In other words, energy is transferred over a certain duration of time from the transmit coil to the receive coil, and the rate of such energy transfer is power. However, the words "energy" and "power" are frequently used somewhat interchangeably when describing a magnetic induction circuit, since a circuit that transfers power (i.e., at a certain rate) also transfers a corresponding amount of energy over a duration of time. As such, disabling power transfer also likewise disables energy transfer when disabled for a certain period of time. Moreover, reducing power transfer also likewise reduces energy transfer over a period of time. For this reason, in context there is seldom confusion between usage of the phrases "transferred energy" and "transferred power", or between the phrases "received energy" and "received power," as it is usually clear in context whether the reference is to total transfer over a duration of time, or to an instantaneous rate of transfer.

The phrases "power transfer" or "energy transfer" may also be somewhat informally referred to as "charge transfer" because such transferred charge may be for delivering power, in the form of a current (i.e., moving electronic charge) at a certain voltage, to operate circuitry within the implantable device, in addition to (or instead of) charging a supercapacitor, battery, or other charge storage device within the implantable device. Consequently, as used herein, an external charging system may also be viewed as an external charge transfer system or an external power transfer system, and references herein to an external charging system, an external charge transfer system, and an external power transfer system may be used interchangeably with no specific distinction intended unless clear in the context of such use, even if no charge storage device is "charged" in a given embodiment. Such external charging, charge transfer, or power transfer systems may also be viewed as an external control system or device. Similarly, a charge receiving system may also be viewed as a power receiving system, and references herein to a charge receiving system and a power receiving system may be used interchangeably with no specific distinction intended unless clear in the context of such use.

Regarding terminology used herein, it will be appreciated by one skilled in the art that any of several expressions may be equally well used when describing the operation of a circuit including the various signals and nodes within the circuit. Any kind of signal, whether a logic signal or a more general analog signal, takes the physical form of a voltage level (or for some circuit technologies, a current level) of a node within the circuit. Such shorthand phrases for describing circuit operation used herein are more efficient to communicate details of circuit operation, particularly because the schematic diagrams in the figures clearly associate various signal names with the corresponding circuit blocks and nodes.

An insulated gate field effect transistor (IGFET) may be conceptualized as having a control terminal which controls the flow of current between a first current handling terminal and a second current handling terminal. Although IGFET transistors are frequently discussed as having a drain, a gate, and a source, in most such devices the drain is interchangeable with the source. This is because the layout and semiconductor processing of the transistor is frequently symmetrical (which is typically not the case for bipolar transistors). For an N-channel IGFET transistor, the current handling terminal normally residing at the higher voltage is customarily called the drain. The current handling terminal normally residing at the lower voltage is customarily called the source. A sufficient voltage on the gate (relative to the source voltage) causes a current to therefore flow from the drain to the source. The source voltage referred to in N-channel IGFET device equations merely refers to whichever drain or source terminal has the lower voltage at any given point in time. For example, the "source" of the N-channel device of a bi-directional CMOS transfer gate depends on which side of the transfer gate is at the lower voltage. To reflect this symmetry of most N-channel IGFET transistors, the control terminal may be deemed the gate, the first current handling terminal may be termed the "drain/source", and the second current handling terminal may be termed the "source/drain". Such a description is equally valid for a P-channel IGFET transistor, since the polarity between drain and source voltages, and the direction of current flow between drain and source, is not implied by such terminology. Alternatively, one current-handling terminal may arbitrarily deemed the "drain" and the other deemed the "source", with an implicit understanding that the two are not distinct, but interchangeable. It should be noted that IGFET transistors are commonly referred to as MOSFET transistors (which literally is an acronym for "Metal-Oxide-Semiconductor Field Effect Transistor"), even though the gate material may be polysilicon or some material other than metal, and the dielectric may be oxynitride, nitride, or some material other than oxide. The casual use of such historical legacy terms as MOS and MOSFET should not only be interpreted to literally specify a metal gate FET having an oxide dielectric.

Regarding power supplies, a single positive power supply voltage (e.g., a 3.0 volt power supply) used to power a circuit is frequently named the "$V_{DD}$" power supply. In an integrated circuit, transistors and other circuit elements are actually connected to a $V_{DD}$ terminal or a $V_{DD}$ node, which is then operably connected to the $V_{DD}$ power supply. The colloquial use of phrases such as "tied to $V_{DD}$" or "connected to $V_{DD}$" is understood to mean "connected to the $V_{DD}$ node", which is typically then operably connected to actually receive the $V_{DD}$ power supply voltage during use of the integrated circuit. The reference voltage for such a single power supply circuit is frequently called "$V_{SS}$." Transistors and other circuit elements are actually connected to a $V_{SS}$ terminal or a $V_{SS}$ node, which is then operably connected to the $V_{SS}$ power supply during use of the integrated circuit. Frequently the $V_{SS}$ terminal is connected to a ground reference potential, or just "ground." Generalizing somewhat, the first power supply terminal is frequently named "$V_{DD}$", and the second power supply terminal is frequently named "$V_{SS}$." Historically the nomenclature "$V_{DD}$" implied a DC voltage connected to the drain terminal of an MOS transistor and $V_{SS}$ implied a DC voltage connected to the source terminal of an MOS transistor. For example, legacy PMOS circuits used a negative $V_{DD}$ power supply, while legacy NMOS circuits used a positive $V_{DD}$ power supply. Common usage, however, frequently ignores this legacy and uses $V_{DD}$ for the more positive supply voltage and $V_{SS}$ for the more negative (or ground) supply voltage unless, of course, defined otherwise. Describing a circuit as functioning with a "$V_{DD}$ supply" and "ground" does not necessarily mean the circuit cannot function using other power supply potentials.

Other common power supply terminal names are "$V_{cc}$" (a historical term from bipolar circuits and frequently synonymous with a +5 volt power supply voltage, even when used with MOS transistors which lack collector terminals) and "GND" or just "ground."

Moreover, implementation of the disclosed devices and techniques is not limited by CMOS technology, and thus implementations can utilize NMOS, PMOS, and various bipolar or other semiconductor fabrication technologies. While the disclosed devices and techniques have been described in light of the embodiments discussed above, one skilled in the art will also recognize that certain substitutions may be easily made in the circuits without departing from the teachings of this disclosure. Also, many circuits using NMOS transistors may be implemented using PMOS transistors instead, as is well known in the art, provided the logic polarity and power supply potentials are reversed. In this vein, the transistor conductivity type (i.e., N-channel or P-channel) within a CMOS circuit may be frequently reversed while still preserving similar or analogous operation. Moreover, other combinations of output stages are possible to achieve similar functionality.

The various techniques, structures, and methods described above are contemplated to be used alone as well as in various combinations. It should be understood that the drawings and detailed description herein are to be regarded in an illustrative rather than a restrictive manner, and are not intended to be limiting to the particular forms and examples disclosed. On the contrary, included are any further modifications, changes, rearrangements, substitutions, alternatives, design choices, and embodiments apparent to those of ordinary skill in the art, without departing from the scope of the invention as defined by the claims in this application or in any application claiming priority to this application. Thus, it is intended that such claims be interpreted to embrace all such further modifications, changes, rearrangements, substitutions, alternatives, design choices, and embodiments.

What is claimed is:

1. A system for communicating between and for transferring power from an external power transfer system (EPTS) to at least one body-implantable active device (BIAD) through a dermis layer, said system comprising:
   an EPTS for being disposed external to a dermis layer of a body; and
   a BIAD for being disposed beneath the dermis layer of the body;
   the EPTS including:
   a transmit coil;
   a transmit coil driver circuit operable to drive the transmit coil with a resonant current at a resonant frequency; and
   a telemetry receiver circuit coupled to the transmit coil, operable to generate a first output signal reflective of changes in transmit coil peak resonant current corresponding to a first frequency range, and further operable to generate a second output signal reflective of changes in the transmit coil peak resonant current corresponding to a lower frequency than the first frequency range;
   the BIAD including:
   a receive coil tuned to the resonant frequency of the transmit coil and operable to inductively receive power therefrom when in proximity thereto;
   a power receiving circuit coupled to the receive coil, said power receiving circuit operable to de-tune the receive coil to substantially inhibit power transfer from the transmit coil to the receive coil, and to thereby decrease transmit coil loading and effect a corresponding change in the transmit coil peak resonant current; and a de-tune control circuit coupled to the power receiving circuit, and operable to intermittently de-tune the receive coil at a first rate corresponding to the first frequency range, and further operable to intermittently de-tune the receive coil at a second rate lower than the first frequency range.

2. The system as in claim 1 wherein:

the de-tune control circuit is responsive to a serial back telemetry transmit data stream and is operable to de-tune the receive coil during each bit position of the serial back telemetry transmit data stream having a first digital state, and to allow the receive coil to remain tuned during each bit position of the serial back telemetry transmit data stream having a second digital state opposite the first digital state; and the first output signal corresponds to a serial back telemetry receive data stream.

3. The system as in claim 2 wherein:

the back telemetry transmit data stream has a bit rate corresponding to a frequency lower than the resonant frequency by at least a factor of 20.

4. The system as in claim 1 wherein the telemetry receiver circuit comprises:

a current sensor circuit having an input coupled to the transmit coil, and operable to generate on an output thereof an AC signal representative of instantaneous transmit coil current; and a demodulator circuit having an input coupled to the output of the current sensor circuit, and operable to provide on an output thereof a signal representing a peak value of the instantaneous transmit coil current.

5. The system as in claim 4 wherein the telemetry receiver circuit further comprises:

a band-pass filter circuit having an input coupled to the demodulator circuit output, and operable to generate on an output thereof the first output signal of the telemetry receiver circuit; and a low-pass filter circuit having an input coupled to the demodulator circuit output, and operable to generate on an output thereof the second output signal of the telemetry receiver circuit.

6. The system as in claim 4 wherein the current sensor circuit comprises:

an I-to-V converter circuit operable to generate on an output thereof an AC voltage signal representative of the instantaneous transmit coil current.

7. The system as in claim 6 wherein the I-to-V converter circuit comprises:

an RC circuit having an RC time constant that substantially matches an RL time constant of the transmit coil, wherein said AC voltage signal conveyed on the I-to-V converter circuit output follows its input voltage delayed by the RC time constant, and wherein the AC voltage signal is substantially in-phase with the instantaneous transmit coil current.

8. The system as in claim 6 wherein the I-to-V converter circuit further comprises:

a ground restore circuit operable to shift the AC voltage signal to a non-negative voltage range.

9. The system as in claim 5 wherein the band-pass filter circuit comprises:

a band-pass filter/amplifier circuit having an input coupled to the input of the band-pass filter circuit, and operable to provide on a first output thereof a back telemetry received data analog signal, and further operable to provide on a second output thereof a back telemetry reference signal; and a comparator circuit having a first input coupled to the back telemetry received data analog signal output of the band-pass filter/amplifier circuit, and having a second input coupled to the back telemetry reference signal output of the band-pass filter/amplifier circuit, and operable to generate on an output thereof a back telemetry digital receive data signal which is coupled to the first output signal of the telemetry receiver circuit.

10. The system as in claim 1 wherein:

the BIAD comprises a head-locatable neurostimulation system;

the EPTS is disposed within a headset charging and control device operable to charge and communicate with the head-locatable neurostimulation system; and the transmit coil is co-locatable with the receive coil.

11. A system for communicating between and for transferring power from an external power transfer system (EPTS) to at least one body-implantable active device (BIAD) through a dermis layer, said system comprising:

an EPTS for being disposed external to a dermis layer of a body; and a BIAD for being disposed beneath the dermis layer of the body;

the EPTS including:

a transmit coil;

a transmit coil driver circuit operable to drive the transmit coil with a resonant current at a resonant frequency; and a telemetry receiver circuit coupled to the transmit coil, operable to generate a first output signal reflective of changes in transmit coil peak resonant current corresponding to a serial back telemetry receive data stream received from the BIAD, and further operable to generate a second output signal reflective of changes in the transmit coil peak resonant current that occur at a lower frequency than the serial back telemetry receive data stream and which second output signal corresponds to an indication of power being coupled to the BIAD;

the BIAD including:

a receive coil tuned to the resonant frequency of the transmit coil and operable to inductively receive power therefrom when in proximity thereto;

a power receiving circuit coupled to the receive coil, said power receiving circuit operable to de-tune the receive coil in response to a de-tune signal to substantially inhibit power transfer from the transmit coil to the receive coil, and to thereby decrease transmit coil loading and effect a corresponding change in the transmit coil peak resonant current; and a de-tune control circuit coupled to the power receiving circuit, and operable to intermittently assert the de-tune signal in accordance with a serial back telemetry transmit data stream, and intermittently assert the de-tune signal at a lower rate than the serial back telemetry transmit data stream to modulate power coupled to the BIAD.

12. The system as in claim 11 wherein:

the de-tune control circuit is operable to assert the de-tune signal during each bit position of the serial back telemetry transmit data stream having a first digital state, and to de-assert the de-tune signal during each bit position of the serial back telemetry transmit data stream having a second digital state opposite the first digital state.

13. The system as in claim 11 wherein the telemetry receiver circuit comprises:
- a current sensor circuit having an input coupled to the transmit coil, and operable to convey on an output thereof an AC signal representative of instantaneous transmit coil current;
- a demodulator circuit having an input coupled to the output of the current sensor circuit, and operable to provide on an output thereof a signal representing a peak value of the instantaneous transmit coil current;
- a band-pass filter circuit having an input coupled to the demodulator circuit output, and operable to generate on an output thereof the first output signal of the telemetry receiver circuit; and
- a low-pass filter circuit having an input coupled to the demodulator circuit output, and operable to generate on an output thereof the second output signal of the telemetry receiver circuit.

14. The system as in claim 13 wherein the current sensor circuit comprises:
- an I-to-V converter circuit having an input coupled to the transmit coil, and operable to generate on an output thereof an AC voltage signal corresponding to the instantaneous transmit coil current; and
- a ground restore circuit coupled to the I-to-V converter circuit, and operable to shift the AC voltage signal to a non-negative voltage range.

15. The system as in claim 14 wherein the I-to-V converter circuit comprises:
- an RC circuit having an input coupled to a circuit node that couples together the transmit coil driver circuit output and one terminal of the transmit coil, further having an RC time constant that substantially matches an RL time constant of the transmit coil, wherein said AC voltage signal conveyed on the I-to-V converter circuit output follows its input voltage delayed by the RC time constant, and wherein the AC voltage signal is substantially in-phase with the instantaneous transmit coil current.

16. The system as in claim 14 wherein the band-pass filter circuit comprises:
- a band-pass filter/amplifier circuit having an input coupled to the input of the band-pass filter circuit, and operable to provide on a first output thereof a back telemetry received data analog signal, and further operable to provide on a second output thereof a back telemetry reference signal; and
- a comparator circuit having a first input coupled to the back telemetry received data analog signal output of the band-pass filter/amplifier circuit, and having a second input coupled to the back telemetry reference signal output of the band-pass filter/amplifier circuit, and operable to generate on an output thereof a back telemetry digital receive data signal which is coupled to the first output signal of the telemetry receiver circuit.

17. The system as in claim 11 wherein:
- the BIAD comprises a head-locatable neurostimulation system;
- the EPTS is disposed within a headset charging and control device operable to charge and communicate with the head-locatable neurostimulation system; and
- the transmit coil is co-locatable with the receive coil.

18. The system as in claim 11 further comprising at least a second BIAD, and wherein:
- the EPTS includes a series-connected plurality of transmit coils, each corresponding to a respective BIAD;
- the transmit coil driver circuit is operable to drive the series-connected plurality of transmit coils with the resonant current at the resonant frequency; and
- the telemetry receiver circuit is coupled to the series-connected plurality of transmit coils.

19. The system as in claim 18 wherein each respective BIAD is independently operable to detune its respective receive coil, without affecting power transfer to, or back telemetry from, any other BIAD.

20. The system as in claim 18 wherein:
- each respective BIAD comprises a respective head-locatable neurostimulation system; and
- the EPTS is disposed within a headset charging and control device operable to charge and communicate with each respective head-locatable neurostimulation system.

* * * * *